United States Patent [19]

Ohno et al.

[11] Patent Number: 4,880,939
[45] Date of Patent: Nov. 14, 1989

[54] 2,5,6,7-TETRANOR-18,18,19,19-TETRADEHYDRO-4,8-INTER-M-PHENYLENE $PGI_2$ DERIVATIVES

[75] Inventors: Kiyotaka Ohno, Fujisawa; Toshiya Takahashi, Kamakura; Shintaro Nishio, Ebina, all of Japan

[73] Assignee: Toray Industries, Japan

[21] Appl. No.: 128,878

[22] Filed: Dec. 4, 1987

[30] Foreign Application Priority Data

Dec. 11, 1986 [JP] Japan ................................. 61-295367

[51] Int. Cl.[4] ................... C07D 307/77; C07D 307/93
[52] U.S. Cl. ..................................... 549/458; 546/269; 549/60
[58] Field of Search .......................................... 549/458

[56] References Cited

U.S. PATENT DOCUMENTS

| | | | |
|---|---|---|---|
| 4,301,164 | 11/1981 | Ohno et al. | 514/468 |
| 4,364,951 | 12/1982 | Skuballa et al. | 549/465 |
| 4,474,802 | 10/1984 | Ohno et al. | 549/465 |
| 4,532,236 | 7/1985 | Nickolson et al. | 549/465 |

FOREIGN PATENT DOCUMENTS 0024943 11/1981 European Pat. Off. .

Primary Examiner—Mary C. Lee
Assistant Examiner—Bernard I. Dentz
Attorney, Agent, or Firm—Austin R. Miller

[57] ABSTRACT

Disclosed herein are novel prostaglandin $I_2$ ($PGI_2$) derivatives exhibiting excellent physiological activities, said derivatives being represented by the general formula:

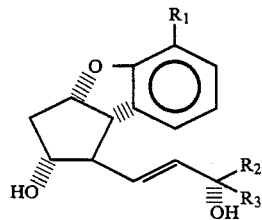

wherein $R_1$, $R_2$ and $R_3$ are as defined herein.

1 Claim, No Drawings

2,5,6,7-TETRANOR-18,18,19,19-TETRADEHYDRO-4,8-INTER-M-PHENYLENE PGI$_2$ DERIVATIVES

BACKGROUND OF THE INVENTION

1. Field of the Invention

The present invention relates to prostaglandin I$_2$ (PGI$_2$) derivatives.

2. Description of the Prior Art

Prostaglandin I$_2$ (PGI$_2$, also called prostacyclin) represented by the formula:

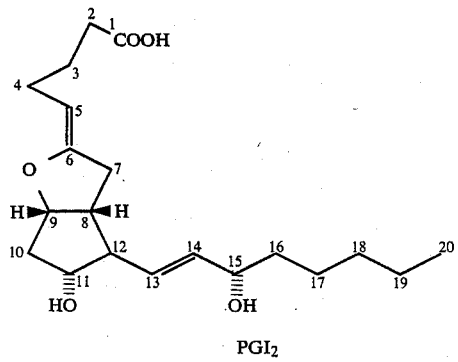

PGI$_2$ was first found by J. R. Vane et al. in 1976. PGI$_2$ is biosynthesized from arachidonic acid via endoperoxide (PGH$_2$ or PGG$_2$) in the vascular wall. It should be nloted that PGI$_2$ shows potent platelet aggregation-inhibiting and gastric acid secretion-inhibiting activities and a potent peripheral blood vessel-dilating activity: refer to C & EN, Dec. 20, 1976, page 17; and S. Moncada, R. Gryglewski, S. Bunting and J. R. Vane, Nature, 263, 633 (1976).

PGI$_2$ is extremely unstable even in neutral aqueous solutions due to its unstable exo-enol structure and readily converted into 6-oxo PGF$_{1\alpha}$ which is substantially inactive physiologically. Such instability of PGI$_2$ is a great obstacle to its use as a drug. Furthermore, PGI$_2$ is unstable in vivo as well and disadvantageously shows only short duration of physiological activities in vivo.

Many studies have been made on various derivatives for the purpose of improving the chemical stability and duration of activities in vivo of PGI$_2$.

The present inventors have also studied and solved this problem of chemical instability of PGI$_2$ by providing novel derivatives of PGI$_2$ having a cyclopenta[b]benzofuran ring in which the exo-enol structure contributing to the instability is incorporated into the phenyl ring. Thus, the present inventors have attained a series of inventions relating to such PGI$_2$ derivatives and filed a number of patent applications: refer to Japanese Patent Application Laying-open (KOKAI) Nos. 56-36477, 57-32277, 57-144276, 58-124778 and 59-134787.

However, although the problem of chemical instability could be solved by the derivatives of PGI$_2$ provided by these prior inventions, the potency of pharmacological activities and in vivo duration thereof are still unsatisfactory.

Accordingly, it is a primary object of this invention to solve such a problem.

SUMMARY OF THE INVENTION

According to this invention, there is provided a 2,5,6,7-tetranor-18,18,19,19-tetradehydro-4,8-inter-m-phenylene PGI$_2$ derivative represented by the following general formula:

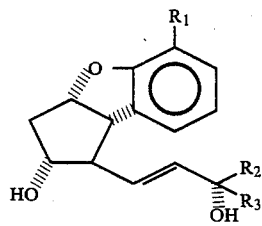

wherein:

R$_1$ is (i) —CH$_2$CH$_2$COOR$_4$, (ii) —CH$_2$CH$_2$CH$_2$OH, or (iii)

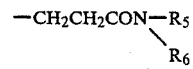

in which R$_4$ is hydrogen, or a pharmacologically acceptable cation or ester residue, and R$_5$ and R$_6$ may be same or different and are independently selected from the class consisting of hydrogen, normal alkyl groups having 1 to 12 carbon atoms, branched alkyl groups having 3 to 12 carbon atoms, cycloalkyl groups having 3 to 12 carbon atoms, cycloalkylalkylene groups having 4 to 13 carbon atoms, and phenyl group;

R$_2$ is hydrogen, methyl, ethyl or propylgroup; and

R$_3$ is —C$_t$H$_{2t}$—C≡C—R$_7$ in which C$_t$H$_{2t}$ represents a normal or branched alkylene group, t is an integer having a value of 1 to 6, and R$_7$ is a normal alkyl group having 1 to 6 carbon atoms.

DESCRIPTION OF THE INVENTION

Illustrative examples of the radical —C$_t$H$_{2t}$—C≡C—R$_7$ reprsented by R$_3$ in the above described general formula may include 2-pentynyl, 3-pentynyl, 2-hexynyl, 3-hexynyl, 4-hexynyl, 2-heptynyl, 3-heptynyl, 4-heptynyl, 5-heptynyl, 2-octynyl, 3-octynyl, 4-octynyl, 5-octynyl, 6-octynyl, 2-nonynyl, 3-nonynyl, 4-nonynyl, 5-nonynyl, 6-nonynyl, 7-nonynyl, 1-methyl-2-pentynyl, 1-methyl-3-pentynyl, 1-methyl-2-hexynyl, 1-methyl-3-hexynyl, 1-methyl-4-hexynyl, 1-methyl-2-heptynyl, 1-methyl-3-heptynyl, 1-methyl-4-heptynyl, 1-methyl-5-heptynyl, 1-methyl-2-octynyl, 1-methyl-3-octynyl, 1-methyl-4-octynyl, 1-methyl-5-octynyl, 1-methyl-6-octynyl, 1-methyl-2-nonynyl, 1-methyl-3-nonynyl, 1-methyl-4-nonynyl, 1-methyl-5-nonynyl, 1-methyl-6-nonynyl, 1,1-dimethyl-2-pentynyl, 1,1-dimethyl-3-pentynyl, 1,1-dimethyl-2-hexynyl, 1,1-dimethyl-3-hexynyl, 1,1-dimethyl-4-hexynyl, 1,1-dimethyl-2-heptynyl, 1,1-dimethyl-3-heptynyl, 1,1-dimethyl-4-heptynyl, 1,1-dimethyl-5-heptynyl, 1,1-dimethyl-2-octynyl, 1,1-dimethyl-3-octynyl, 1,1-dimethyl-4-octynyl, 1,1-dimethyl-5-octynyl, 1,1-dimethyl-2-nonynyl, 1,1-dimethyl-3-nonynyl, 1,1-dimethyl-4-nonynyl, 1,1-dimethyl-5-nonynyl, 2,2-dimethyl-3-pentynyl, 2,2-dimethyl-3-hexynyl, 2,2-dimethyl-4-hexynyl, 2,2-dimethyl-3-heptynyl, 2,2-dimethyl-4-heptynyl, etc.

Pharmacologically acceptable cations represented by R$_4$ in R$_1$ (i) of the above described general formula may include metal cations, ammonium cation, amine cations, and quaternary ammonium cations.

Especially preferred metal cations may be derived from alkali metals, for example, sodium or potassium, or alkaline earth metals, for example, magnesium or calcium. Cations derived from other metals, such as aluminum, zinc and iron, are also included within the scope of this invention.

The pharmacologically acceptable amine cations may be derived from primary, secondary or tertiary amines. Illustrative examples of suitable amines may include aliphatic, alicyclic and aromatic amines containing up to about 18 carbon atoms and heterocyclic amines, for example, methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 4-dimethylpiperazine, 2-methylpiperidine, etc.; water-soluble amines and hydrophilic moiety-containing amines, for example, mono-, di- or triethanolamines, ethyldiethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl)-diethanolamine, galactamine, N-methylglutamine, N-methylglucosamine, ephedrine, phenylephrine, epinephrine, procaine, etc.; and basic amino acids, for example, lysine, arginine, etc.

When $R_4$ in $R_1$ (i) of the above described general formula represents an ester residue, it is selected from the class consisting of:

(i) normal or branched alkyl groups having 1 to 12 carbon atoms;

(ii) —Z—$R_8$ wherein Z represents a valence bond or a normal or branched alkylene group having the formula $C_tH_{2t}$ (in which t is an integer having a value of 1 to 6), and $R_8$ is a cycloalkyl group having 3 to 8 ring carbon atoms which may optionally be substituted by one to four normal alkyl groups containing 1 to 4 carbon atoms;

(iii) —Z—Ar wherein Z is as defined above, and Ar represents a phenyl grup which may optionally be substituted by one to four substituents selected from the class consisting of alkyls, methoxy, chloro, bromo, fluoro, iodo, trifluoromethyl, nitro, cyano and phenyl;

(iv) —$(CH_2CH_2O)_n$—$CH_3$ wherein n is an integer having a value of 1 to 5;

(v) —Z—$R_9$ wherein Z is as defined above, and $R_9$ represents α-naphthyl, β-naphthyl, 2-pyridyl, 3-pyridyl, 4-pyridyl, α-furyl, β-furyl, α-thienyl, or β-thienyl;

(vi) —$C_tH_{2t}$—$COOR_{10}$ wherein $C_tH_{2t}$ and t are as defined above, and $R_{10}$ is methyl, ethyl or propyl group; or (vii)

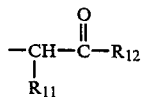

wherein $R_{11}$ is hydrogen or benzoyl group, and $R_{12}$ is phenyl, p-bromophenyl, p-chlorophenyl, p-biphenyl, p-nitrophenyl, p-benzamidophenyl, or 2-naphthyl group.

Illustrative examples of normal alkyl groups having 1 to 12 carbon atoms represented by $R_4$ may include methyl, ethyl, propyl, butyl, pentyl, hexyl, heptyl, octyl, dodecyl, etc.

Illustrative examples of branched alkyl groups having 3 to 12 carbon atoms represented by $R_4$ may include isopropyl, secbutyl, tert-butyl, iso-butyl, 2-methylpentyl, 3-methylpentyl, 4-methylpentyl, 1-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 1-methyldecanyl, 2-methylnonyl, 2-methyldecanyl, 1,1-dimethylbutyl, 2,2-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 7,7-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, etc.

Illustrative examples of the radicals —Z—$R_8$ represented by $R_4$ may include, for example, cyclopentyl, cyclohexyl, cycloheptyl, cyclooctyl, cyclopentylmethyl, cyclohexylmethyl, cycloheptylmethyl, cyclooctylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 4-methylcyclooctyl, 2-ethylcyclopentyl, 3-ethylcyclopentyl, 2-ethylcyclohexyl, 3-ethylcyclohexyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2-methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-ethylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethylcyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl, 5-(2-ethylcyclopentyl)pentyl, cyclopropyl, cyclobutyl, 2,3-dimethylcyclopropyl, 2,4-dimethylcyclobutyl, 3,3-dimethylcyclobutyl, cyclopentyldimethylmethyl, cyclohexyldimethylmethyl, cyclooctyldimethylmethyl, 2-cyclopentyl-1,1- dimethylethyl, 2-cyclohexyl-1,1-dimethylethyl, 2-cyclooctyl-1,1-dimethylethyl, 3-cyclopentyl-1,1-dimethylpropyl, 3-cyclohexyl-1,1-dimethylpropyl, 3-cyclooctyl-1,1-dimethylpropyl, 4-cyclopentyl-1,1-dimethylbutyl, 4-cyclohexyl-1,1-dimethylbutyl, 4-cyclooctyl-1,1-dimethylbutyl, 2-cyclopentyl-2,2-dimethylethyl, 2-cyclohexyl-2,2-dimethylethyl, 2-cyclooctyl-2,2-dimethylethyl, etc.

Illustrative examples of the radicals —Z—Ar represented by $R_4$ may include phenyl, p-chlorophenyl, p-bromophenyl, p-fluorophenyl, 3,4-dichlorophenyl, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethylphenyl, 2,4-dimethylphenyl, 3-chloro-4-methylphenyl, 3-fluoro-4-methylphenyl, 4- biphenyl, benzyl, p-chlorobenzyl, m-chlorobenzyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α'-dimethylbenzyl, phenethyl, p-chlorophenethyl, p-bromophenethyl, p-fluorophenethyl, m-chlorophenethyl, m-fluorophenethyl, o-chlorophenethyl, p-methylphenethyl, p-methoxyphenethyl, 3,4-dimethoxyphenethyl, p-ethylpehenthyl, α-methylphenethyl, β-methylphenethyl, α,α'-dimethylphenethyl, β,β'-dimethylphenethyl, 3-phenylpropyl, 3-(p-chlorophenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl, 5-phenylpentyl, α,α'-dimethyl-p-chlorophenethyl, α,α'-dimethyl-p-bromophenethyl, α,α'-dimethyl-p-fluorophenethyl, α,α'-dimethyl-m-chlorophenethyl, α,α'-dimethyl-m-bromophenethyl, α,α'-dimethyl-m-fluorophenethyl, α,α'-dimethyl-p-trifluoromethylphenethyl, α,α'-dimethyl-m-trifluoromethylphenethyl, α,α'-dimethyl-p-methylphenethyl, α,α'-dimethyl-p-methoxyphenethyl, α,α'-dimethyl-p-cyanophenethyl, 1,1-dimethyl-3-phenylpropyl, 1,1-dimethyl-4-phenylbutyl, etc.

Illustrative examples of the radicals —($CH_2CH_2O$)$_n$—$CH_3$ represented by $R_4$ include —$CH_2CH_2OCH_3$, —$CH_2CH_2OCH_2CH_2OCH_3$, —($CH_2CH_2O$)$_3CH_3$, —($CH_2CH_2O$)$_4CH_3$, and —($CH_2CH_2O$)$_5CH_3$.

Illustrative examples of the radicals —Z—$R_9$ represented by $R_4$ may include α-naphthyl, β-naphthyl, 2-pyridyl, 3-pyridyl, 4-pyridyl, α-furyl, β-furyl, α-thienyl, β-thienyl, α-naphthylmethyl, β-naphthylmethyl, 2-pyridylmethyl, 3-pyridylmethyl, 4-pyridylmethyl, α-furylmethyl, β-furylmethyl, α-thienylmethyl, β-thienylmethyl, 2-(α-naphthyl)ethyl, 2-(β-naphthyl)ethyl, 2-(2-pyridyl)ethyl, 2-(3-pyridyl)ethyl, 2-(4-pyridyl)ethyl, 2-(α-furyl)ethyl, 2-(β-furyl)ethyl, 2-(α-thienyl)ethyl, 2-(β-thienyl)ethyl, 3-(α-naphthyl)propyl, 3-(β-naphthyl)propyl, 3-(2-pyridyl)propyl, 3-(3-pyridyl)propyl, 3-(4-pyridyl)propyl, 3-(α-furyl)propyl, 3-(β-furyl)propyl, 3-(α-thienyl)propyl, 3-(β-thienyl)propyl, etc.

Illustrative examples of the radicals —$C_tH_{2t}COOR_{10}$ represented by $R_4$ may include methoxycarbonylmethyl, ethoxycarbonylmethyl, propoxycarbonylmethyl, 1-methoxycarbonylethyl, 1-ethoxycarbonylethyl, 1-propoxycarbonylethyl, 2-methoxycarbonylethyl, 2-ethoxycarbonylethyl, 2-propoxycarbonylethyl, 3-methoxycarbonylpropyl, 3-ethoxycarbonylpropyl, etc.

Illustrative examples of the radicals

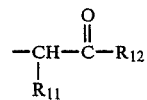

represented by $R_4$ may include phenacyl, p-bromophenacyl, p-nitrophenacyl, p-phenylphenacyl, p-benzamidophenacyl, 2-naphthoylmethyl, α-benzoylphenacyl, etc.

The compounds of the above described general formula provided according to this invention are named after the nomenclature for prostaglandin and prostacycline analogs proposed by N. A. Nelson et al.: N. A. Nelson, J. Med. Chem., 17, 911 (1974); and R. A. Johnson, D. R. Morton and N. A. Nelson, Prostaglandins, 15, 737 (1978).

Among those having the basic molecular structure of the present compounds, the most fundamental compound, which falls outside the scope of this invention, is represented by the following formula:

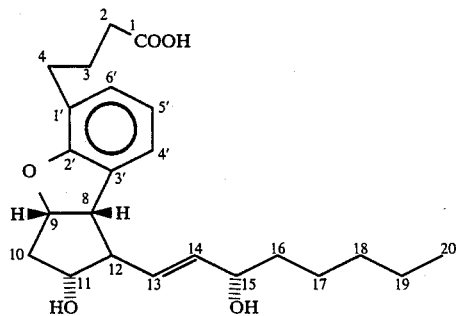

and this compound may be named as 5,6,7-trinor-4,8-inter-m-phenylene $PGI_2$ baased on the numbering of each carbon atom as shown above.

Although this naming does not reasonably accord with the nomenclature given in the aforementioned references, it will herein be applied to the $PGI_2$ derivatives according to this invention which have the specific structure involving a cyclopenta[b]benzofuran skeleton, in order to avoid complexity. According to the nomenclature of the aforementioned references, the above described fundamental compound may be named as 9-deoxy-2',9α-epoxy-5,6,7-trinor-4,8-inter-m-phenylene $PGF_{1α}$.

In the present specification, the fundamental compound will be informally called 5,6,7-trinor-4,8-inter-m-phenylene $PGI_2$ as above mentioned, but other rules for naming the present compounds will follow those given in the aforementioned references.

Incidentally, the nomenclature of the references is also informal and, according to IUPAC's formal nomenclature, these compounds may be named as having a cyclopenta[b]benzofuran ring as a substituent. The 1H-cyclopenta[b]benzofuran is represented by the formula:

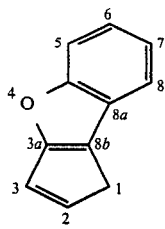

Thus, the fundamental compound described above is formally named as 1β-(3-hydroxy-1-octenyl)-2α-hydroxy-3aβH,8bβH-2,3,3a,8b-tetrahydro-5-1H-cyclopenta[b]benzofuranbutanoic acid.

The naming of some compounds according to this invention will be hereinbelow illustrated together with the molecular structure thereof. 16,16-Dimethyl-2,5,6,7-tetranor-18,18,19,19-tetradehydro-4,8-inter-m-phenylene PGI$_2$:

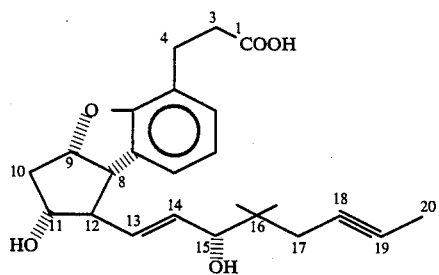

16-Methyl-20a,20b,20c-trihomo-2,5,6,7-tetranor-18,18,19,19-tetradehydro-4,8-inter-m-phenylene PGI$_2$:

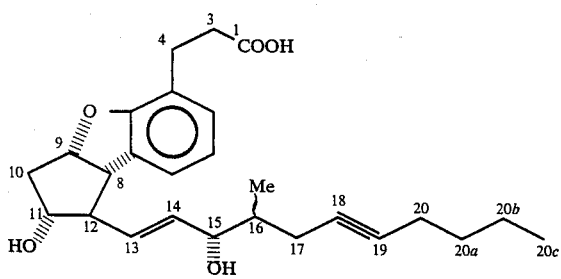

An individual compound according to this invention is herein shown by the structural formula of only one of its potential, optically active isomers. However, it should be understood that the general formula shown herein is intended to encompass all d-, l- and dl-isomers. The R,S-expression corresponding to the absolute configuration of each compound is not shown in the above described formulae.

Illustrative examples of the compounds according to this invention will be given hereinbelow:

16-methyl-2,5,6,7-tetranor-18,18,19,19-tetradehydro-4,8-inter-m-phenylene PGI$_2$;

16-methyl-20a-homo-2,5,6,7-tetranor-18,18,19,19-tetradehydro-4,8-inter-m-phenylene PGI$_2$;

16-methyl-20a,20b-dihomo-2,5,6,7-tetranor-18,18,19,19-tetradehydro-4,8-inter-m-phenylene PGI$_2$;

16-methyl-20a,20b,20c-trihomo-2,5,6,7-tetranor-18,18,19,19-tetradehydro-4,8-inter-m-phenylene PGI$_2$;

16-methyl-20a,20b,20c,20d-tetrahomo-2,5,6,7-tetranor-18,18,19,19-tetradehydro-4,8-m-phenylene PGI$_2$;

16-methyl-20a,20b,20c,20d,20e-pentahomo-2,5,6,7-tetranor-18,18,19,19-tetradehydro-4,8-inter-m-phenylene PGI$_2$;

16,16-dimethyl-2,5,6,7-tetranor-18,18,19,19-tetradehydro-4,8-inter-m-phenylene PGI$_2$;

16,16-dimethyl-20a-homo-2,5,6,7-tetranor-18,18,19,19-tetradehydro-4,8-inter-m-phenylene PGI$_2$;

16,16-dimethyl-20a,20b-dihomo-2,5,6,7-tetranor-18,18,19,19-tetradehydro-4,8-inter-m-phenylene PGI$_2$;

16,16-dimethyl-20a,20b,20c-trihomo-2,5,6,7-tetranor-18,18,19,19-tetradehydro-4,8-inter-m-phenylene PGI$_2$;

16,16-dimethyl-20a,20b,20c,20d-tetrahomo-2,5,6,7-tetranor-18,18,19,19-tetradehydro-4,8-inter-m-phenylene PGI$_2$;

16,16-dimethyl-20a,20b,20c,20d,20e-pentahomo-2,5,6,7-tetranor-18,18,19,19-tetradehydro-4,8-inter-m-phenylene PGI$_2$;

15,16-dimethyl-2,5,6,7-tetranor-18,18,19,19-tetradehydro-4,8-inter-m-phenylene PGI$_2$;

15,16-dimethyl-20a-homo-2,5,6,7-tetranor-18,18,19,19-tetradehydro-4,8-inter-m-phenylene PGI$_2$;

15,16-dimethyl-20a,20b-dihomo-2,5,6,7-tetranor-18,18,19,19-tetradehydro-4,8-inter-m-phenylene PGI$_2$;

15,16-dimethyl-20a,20b,20c-trihomo-2,5,6,7-tetranor-18,18,19,19-tetradehydro-4,8-inter-m-phenylene PGI$_2$;

15,16-dimethyl-20a,20b,20c,20d-tetrahomo-2,5,6,7-tetranor-18,18,19,19-tetradehydro-4,8-inter-m-phenylene PGI$_2$;

15,16-dimethyl-20a,20b,20c,20d,20e-pentahomo-2,5,6,7-tetranor-18,18,19,19-tetradehydro-4,8-inter-m-phenylene PGI$_2$;

15,16,16-trimethyl-2,5,6,7-tetranor-18,18,19,19-tetradehydro-4,8-inter-m-phenylene PGI$_2$;

15,16,16-trimethyl-20a-homo-2,5,6,7-tetranor-18,18,19,19-tetradehydro-4,8-inter-m-phenylene PGI$_2$;

15,16,16-trimethyl-20a,20b-dihomo-2,5,6,7-tetranor-18,18,19,19-tetradehydro-4,8-inter-m-phenylene PGI$_2$;

15,16,16-trimethyl-20a,20b,20c-trihomo-2,5,6,7-tetranor-18,18,19,19-tetradehydro-4,8-inter-m-phenylene PGI$_2$;

15,16,16-trimethyl-20a,20b,20c,20d-tetrahomo-2,5,6,7-tetranor-18,18,19,19-tetradehydro-4,8-inter-m-phenylene PGI$_2$;

15,16,16-trimethyl-20a,20b,20c,20d,20e-pentahomo-2,5,6,7-tetranor-18,18,19,19-tetradehydro-4,8-inter-m-phenylene PGI$_2$;

and methyl, ethyl, propyl, and benzyl esters thereof.

Among various compounds of this invention, those having the general formula wherein R$_1$ is —CH$_2$CH$_2$COOR$_4$, R$_4$ is hydrogen, and R$_2$ is hydrogen may be prepared by a process according to the following Reaction Scheme A. In the formulae I–IV, R represents acyl having 2 to 6 carbon atoms, or a aroyl having 7 to 13 carbon atoms.

Reaction Scheme A

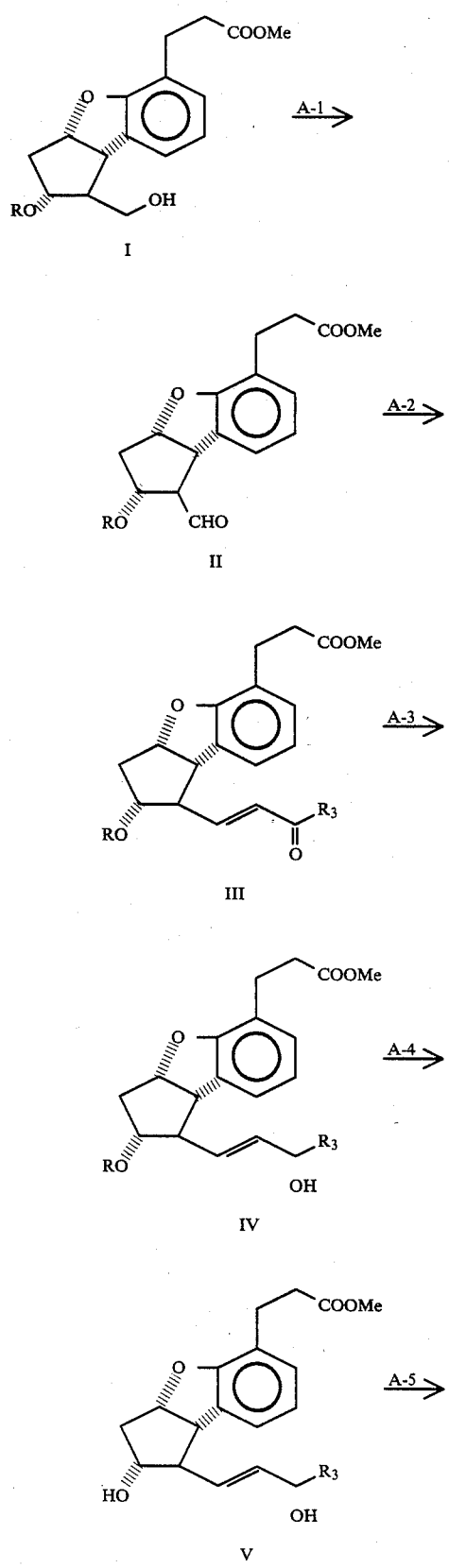

-continued
Reaction Scheme A

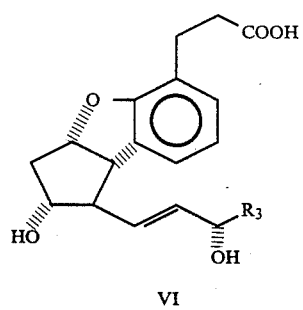

VI

Step A-1 of the Reaction Scheme A is a so-called oxidation process of an alcohol I (in which R represents an ester residue) into an aldehyde II. Various oxidizing agents may be used in the step. Preferred oxidizing agents for use herein in the oxidation of the alcohol I may include Collins' reagent, i.e., a complex of chromic anhydride and pyridine, dimethyl sulfoxide/dicyclohexylcarbodiimide, dimethylsulfide/chlorine, N-bromosuccinimide/chlorine, and the like.

Step A-2 may be effected by condensing the aldehyde II with a dimethyl phosphonate represented by the general formula:

$$(MeO)_2\overset{O}{\underset{\|}{P}}-CH_2-\overset{O}{\underset{\|}{C}}-R_3$$

wherein $R_3$ is as defined previously. Usually, the dimethyl phosphonate ester of the above formula may be reacted with a metal hydride such as sodium hydride or potassium hydride in an etheric solvent, for example, tetrahydrofuran or dimethoxyethane to form a corresponding salt, and the aldehyde II is then added to this salt. The reaction temperature may be chosen from the range of $-30°$ C. to $100°$ C. Room temperature is usually employed.

The dimethyl phosphonate esters of the above formula may be synthesized according to the following reaction formula (refer to E. J. Corey et al., J. Am. Chem. Soc., 88, 5654 (1966)):

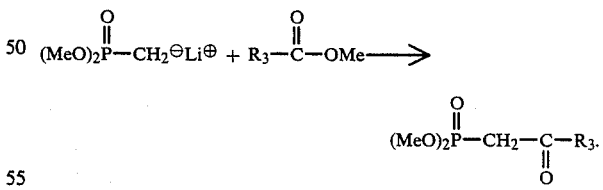

In Step A-3, an $\alpha,\beta$-unsaturated ketone III obtained in Step A-2 is converted into a corresponding allyl alcohol IV. Reducing agents which are generally used in this step should be chosen from those capable of reducing only the ketone moiety in the compound III without reducing the ester residues present therein. In general, metal hydrides, trialkoxy aluminum compounds or dialkyl aluminum compounds are preferably employed in the Step A-3. Preferred reducing agents may include, but are not limited to, zinc borohydride $Zn(BH_4)_2$; a combination of sodium borohydride with cerium trichloride; diisobutyl (2,6-dimethylphenoxy)

aluminum; triisopropoxy aluminum; and the like. Sodium borohydride/cerium trichloride may usually give preferable results with the most preferred solvent being methanol. When zinc borohydride or an organic aluminum reducing agent is used, an etheric solvent such as ether, tetrahydrofuran or dimethoxyethane may preferably be employed. The reaction temperature may be chosen from the range of −110° C. to 80° C. Temperatures between −78° C. and room temperature are usually preferred. After completion of Step A-3, the resulting compound, which is generally a mixture of a 15-α isomer IV and a corresponding 15-β isomer, may be utilized as a starting material of the subsequent reaction in Step A-4 without isolation into each isomer.

Step A-4 is a transesterification process of the R group in the compound IV with methanol. This step may easily be effected by dissolving the compound IV (or, in general, a mixture thereof with its correspoding 15-β isomer) into methanol, adding a suitable base to the resulting solution, and allowing the reaction mixture to stand at a temperature in the range of −30° C. to 100° C. Preferred bases may include anhydrous sodium carbonate, anhydrous potassium carbonate, sodium methoxide, potassium methoxide, etc. In this step, it is preferred that the base and methanol used are anhydrous in order to attain a higher yield of the compound V. The resulting compound from Step A-4 is usually a mixture of a 15-α isomer V and its corresponding 15-β isomer. Each isomer may be isolated by column chromatography. Generally, satisfactory isolation may be attained by using a mixed ethyl acetate/cyclohexane solvent as an eluent on silica gel.

Step A-5 is a hydrolysis process of the methyl ester compound V. This step may be carried out by reacting the compound V with a base in a water-containing alcoholic solvent or a water-containing etheric solvent. Alcohols may include methanol, ethanol, etc., and ethers may include dioxane, tetrahydrofuran, etc. Preferred bases used in this step may be inorganic bases, including sodium hydroxide, potassium hydroxide, sodium carbonate, and potassium carbonate. The reaction temperature may be chosen from the range of −20° C. to 150° C. Generally, room temperature is preferably used with good reaction rates being obtained.

If a 15-β isomer of the compound V usually obtained from Step A-4 is subjected to Step A-5, a 15-β isomer corresponding to the compound VI can be yielded.

The compounds I, which are used as starting materials in the Reaction Scheme A, may be prepared according to the process shown below (Reaction Scheme B). Details for the practice of the scheme B will be given in Reference Examples described hereinafter.

Reaction Scheme B

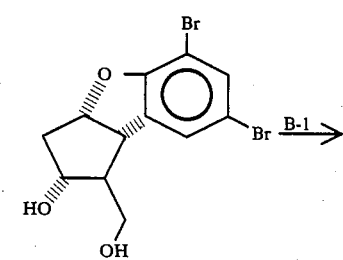

-continued
Reaction Scheme B

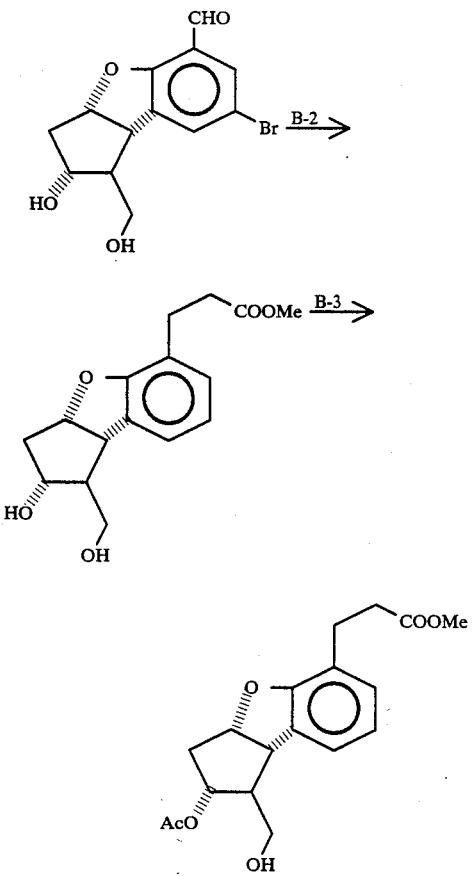

Among various compounds of this invention, those having the general formula wherein $R_1$ is also $-CH_2CH_2COOR_4$, but $R_4$ is not hydrogen or cation, that is, $R_4$ represents an ester residue, may be prepared by esterification of corresponding carboxylic acids wherein $R_4$ is hydrogen. Many known methods of esterification can be employed. Particularly preferred methods for use herein may include (i) a diazoalkane method, (ii) a method utilizing a silver or tertiary amine salt of a carboxylic acid and an active halide, and (iii) a mixed acid anhydride method.

In the first method involving the action of a diazoalkane on a carboxylic acid, a desired product can be easily obtained by contacting the diazoalkane with the carboxylic acid in an appropriate solvent. Diazoalkanes which can be used herein may include, but are not limited to, diazomethane, diazoethane, diazopropane, diazodecane, etc.

The second method may usually be performed by reacting a silver or tertiary amine salt of a carboxylic acid with an active halide in an aprotic, polar solvent such as dimethylformamide, acetonitrile, etc. Examples of active halides may include, but are not limited to, benzyl chloride, benzyl bromide, p-bromobenzyl bromide, p-methoxybenzyl bromide, p-phenylbenzyl bromide, phenacyl bromide, p-bromophenacyl bromide, p-nitrophenacyl bromide, α-benzoylphenacyl bromide, etc.

The third, mixed acid anhydride method is most widely used in many applications. Thus, most of the esterified compounds falling within the scope of this invention may be prepared by this method. In this method, a salt of a carboxylic acid is reacted with ethyl chlorocarbonate, pivaloyl chloride, or p-toluenesulfonic acid chloride to form a mixed acid anhydride. An excess amount of an alcohol represented by the formula R₄OH wherein R₄ is as defined above but does not represent hydrogen or cation is then added to the mixed acid anhydride followed by heating. Illustrative examples of alcohols employed may include, but are not limited to, methanol, ethanol, propanol, butanol, octanol, decanol, isopropanol, 2-ethylhexanol, benzyl alcohol, p-bromobenzyl alcohol, phenethyl alcohol, cyclopentyl alcohol, cyclopentylmethyl alcohol, cyclohexanol, cyclohexylmethyl alcohol, 2-methoxyethanol, 2-(2-methoxyethoxy)ethanol, methyl hydroxyacetate, ethyl lactate, methyl γ-hydroxybutyrate, 2-butyn-1-ol, 2-pentyn-1-ol, 1,3-di-O-methylglycerin, 1,3-diacetylglycerin, phenol, p-bromophenol, p-fluorophenol, m-chlorophenol, m-fluorophenol, 3,4-dichlorophenol, p-(trifluoromethyl)phenol, p-methylphenol, 3,4-dimethylphenol, p-methoxyphenol, 4-phenoxyphenol, p-benzoylaminophenol, etc.

Among the compounds of this invention, those having the general formula wherein R₁ is

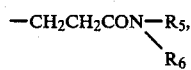

in which R₅ and R₆, same or different, are as defined previously, may be prepared by amidizing corresponding compounds falling within the scope of this invention wherein R₁ is —CH₂CH₂COOH according to the process shown in the following Reaction Scheme C:

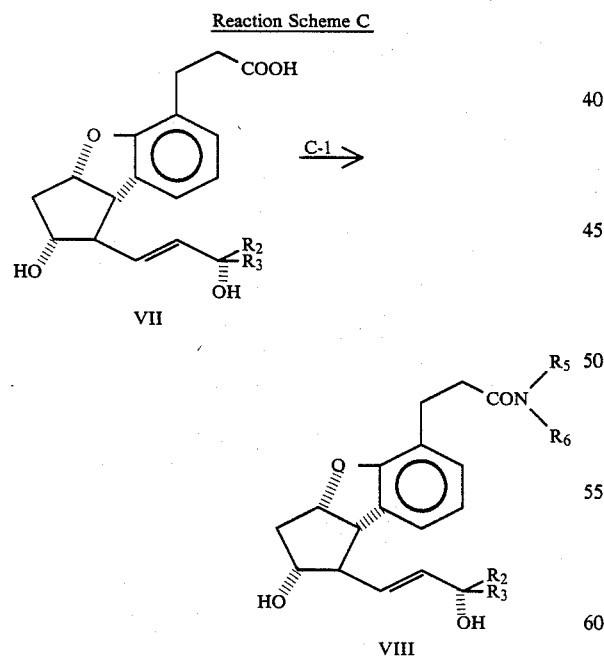

In general, Step C-1 for converting a carboxylic acid VII into its corresponding amide VIII may be effected by reacting the carboxylic acid of the general formula VII with a tertiary amine to produce a quaternary ammonium salt of the carboxylic acid; then reacting the salt with ethyl chlorocarbonate or p-toluenesulfonic acid chloride to form a mixed acid anhydride; and finally adding an amine of the formula

to the mixed acid anhydride followed by heating. Illustrative examples of the amines for use herein may include, but are not limited to, ammonia, N-methylamine, N-ethylamine, N-butylamine, N,N-dimethylamine, N,N-diethylamine, aniline, p-bromoaniline, cyclohexylamine, cyclopentylamine, N-benzylamine, phenethylamine, morpholine, piperidine, etc.

Among the compounds of this invention, those having the general formula wherein R₁ is —CH₂CH₂CH₂OH may be prepared by reducing corresponding compounds falling within the scope of this invention wherein R₁ is —CH₂CH₂COOR₄ and R₄ is an ester residue. Generally, such alcoholic compounds may be prepared from their corresponding methyl ester compounds wherein R₁ is —CH₂CH₂COOR₄ and R₄ is methyl according to the process shown in the following Reaction Scheme D:

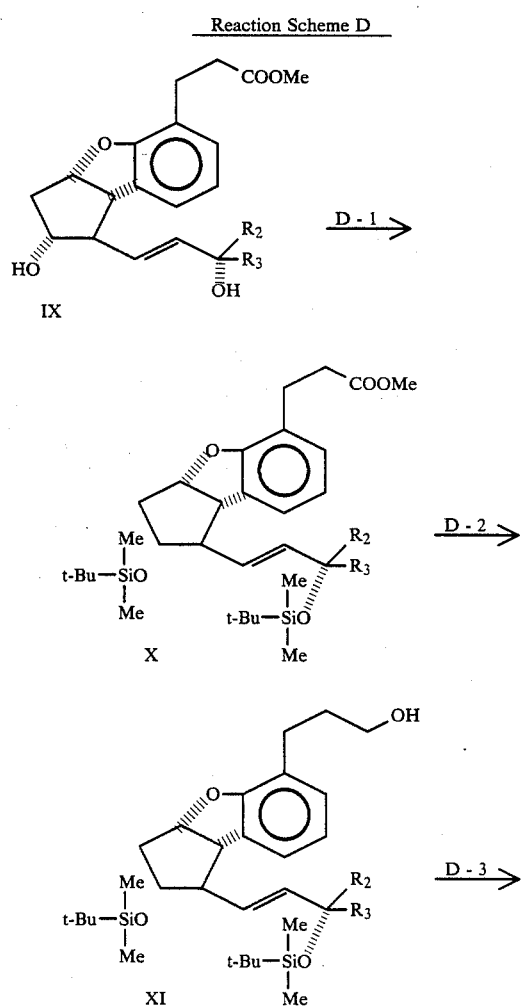

-continued
Reaction Scheme D

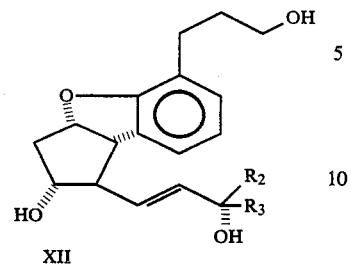

Step D-1 for substituting hydrogen atoms of free hydroxyl groups in a compound of the formula IX with dimethyl-tert-butylsilyl groups may generally be effected by adding imidazole as a catalyst to a solution of the compound IX in dimethylformamide and further adding dimethyl-tert-butylsilyl chloride thereto to thereby react them. The reaction temperature may usually be in the range of 0° to 50° C. where preferable reaction rates can be yielded.

Step D-2 for reducing the methyl ester residue present in the compound X obtained in Step D-1 may generally be carried out by contacting the compound X with either diisobutylaluminum hydride in a non-polar solvent, such as benzene or toluene, or with lithium aluminum hydride in an etheric solvent, such as tetrahydrofuran or ethyl ether. This step may usually be performed at a temperature in the range of −78° C. to 100° C. Temperatures as low as −78° C. may yield satisfactory reaction rates.

Step D-3 for deprotecting the alcohol XI may usually be effected by contacting the compound XI with tetraalkylammonium fluoride to remove the protective groups, i.e., dimethyl-tert-butylsilyl groups, from the compound XI. Any tetraalkylammonium fluoride can be employed herein. In general, tetrabutylammonium fluoride which is readily available can preferably be employed. This reaction is carried out in a solvent, preferably tetrahydrofuran, dimethoxyethane, dimethylformamide, etc.

Alternatively, the compounds of the general formula IX may be directly subjected to Step D-2 and the compounds of the general formula XII can thereby be obtained with good yields.

Among the compounds of this invention, those having the general formula wherein $R_2$ is methyl, ethyl or propyl, $R_1$ is —$CH_2CH_2COOR_4$, and $R_4$ is hydrogen may be prepared from the aforementioned compounds of the general formula III wherein R is as defined above according to the process shown in the following Reaction Scheme E:

Reaction Scheme E

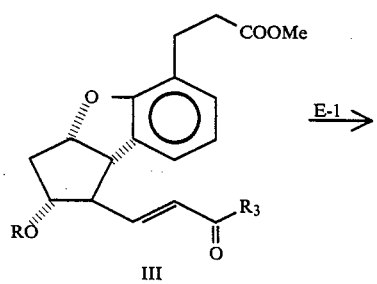

-continued
Reaction Scheme E

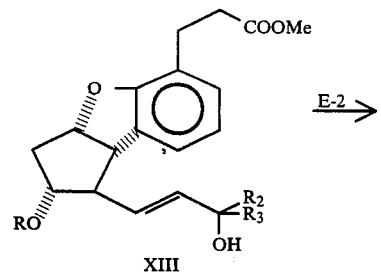

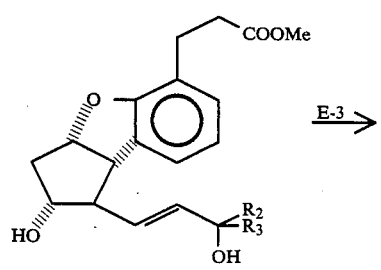

Step E-1 is an alkylating process of an unsaturated ketone of the general formul III and may generally be effected by dissolving the ketone III in an etheric solvent, such as tetrahydrofuran, ethyl ether, etc., and reacting it with alkylmagnesium halide or alkyl lithium. The reaction is preferably carried out in the presence of anhydrous cerium chloride with good yields. The reaction temperature can also be as low as −78° C. and good reaction rates can be obtained.

Step E-2 may be effected in the same manner as Step A-4 described above.

Step E-3 may be effected in the same manner as Step A-5 described above.

Among the compounds of this invention, optically active compounds of the general formula VI may be prepared by subjecting their corresponding optically active compounds of the general formula I to the process shown in Reaction Scheme A mentioned previously.

The optically active compounds of the general formula I may be produced by the following Reaction Scheme F:

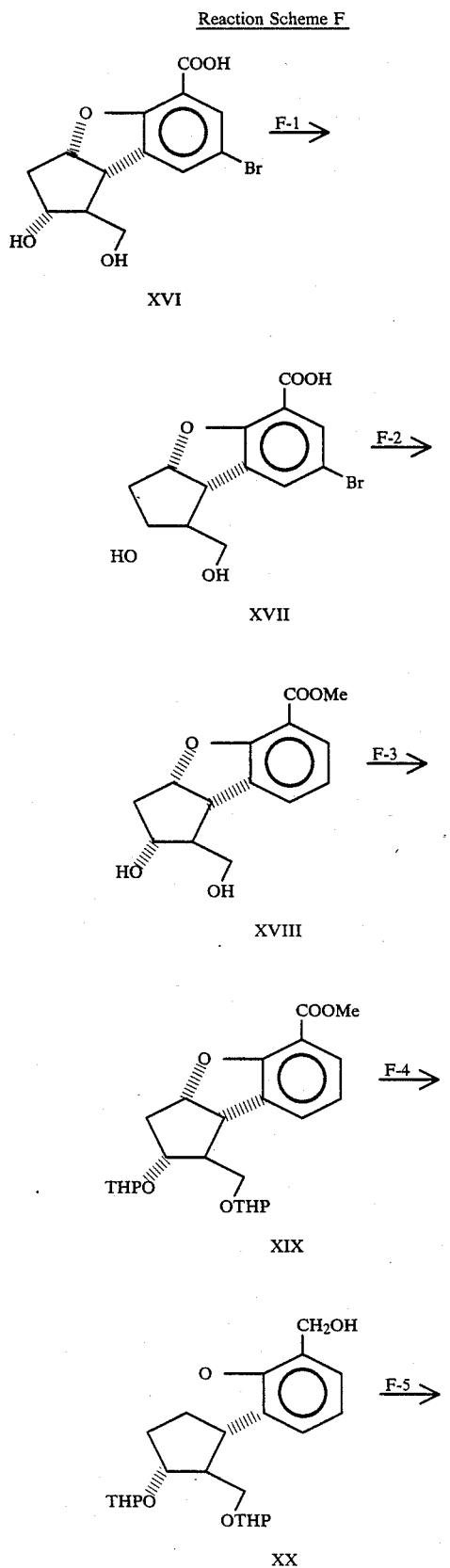
Starting materials of the general formula XVI employed in Reaction Scheme F can be prepared by a process such as disclosed in the present inventors' patent applications, including Japanese patent application laying-open (KOKAI) No. 58-124778.

Step F-1 is a process for convertin a racemic mixture XVI into each opticlly active isomer XVII by so-called racemic resolution. This process is described in Japanese patent application No. 58-34641.

Step F-2 is a process for effecting both dehalogenation and esterification of the optically active compound XVII and may generally be carried out by hydrogenation under usual conditions. More particularly, the hydrogenation may be performed by using a catalyst such as palladium-carbon, palladium-barium sulfate, Raney nickel and the like in the presence of hydrogen at normal or higher pressure up to 10 atm. After dehalogenation, heating under reflux using 300 equivalents or more of methanol in an argon atmosphere may give better reaction rates of esterification.

Step F-3 is a process for substituting the hydrogen atoms of the hyddroxyl groups in a compound of the general formula XVIII by tetrahydropyranyl (THP) groups. This step may generally be performed by reacting the compound XVIII with dihydropyran in the presence of an acid catalyst in a halogenated hydrocarbon solvent, such as dichloromethane or chloroform, or an etheric solvent, such as tetrahydrofuran or dimethoxyethane. Acid catalysts which can be used herein may include, but are not limited to, hydrochloric acid, acetic acid, p-toluenesulfonic acid, phosphoric acid, etc. The reaction can be carried out at a temperature of 0° to 50° C. Generally, room temperature may yield good reaction rates.

Step F-4 may be carried out in the same manner as Step D-2 described above.

Step F-5 is a process for oxidizing a benzyl alcohol of the general formula XX to a benzaldehyde of the general formula XXI. This step may usually be performed by reacting the alcohol XX with an excess amount of manganese dioxide in a non-polar solvent, such as n-hexane or benzene, a halogenated hydrocarbon solvent, such as dichloromethane or chloroform, or an etheric solvent, such as tetrahydrofuran or ethyl ether.

Step F-6 is a process for converting the aldehyde XXI into an $\alpha,\beta$-unsaturated ester compound of the general formula XXII in which the carbon chain has been extended by two carbon atoms by Wittig reaction. In general, this process may be carried out by reacting the compound XXI with carbomethoxymethylene triphenylphospholan in a non-polar solvent such as benzene or toluene. The reaction can be performed at a temperature in the range of 0° to 100° C. Usually, room temperature may yield preferable reaction rates.

Step F-7 may be performed in the same manner as Step F-2 described above.

In Step F-8, the tetrahydropyranyl groups of the compound XXIII obtained in Step F-7 are removed by the action of an acid catalyst to reproduce free hydroxyl groups. The reaction may be carried out by adding an appropriate amount of an acid catalyst, such as hydrochloric acid, acetic acid, p-toluenesulfonic acid or phosphoric acid, to a solution of the compound XXIII dissolved in a suitable solvent. Other acid catalyst may be employed herein. Commonly employed solvents may include water; a water-containing solvent such as acetonitrile-water, tetrahydrofuran-water or acetic acid-water, acetic acid; methanol; and ethanol.

Step F-9 may be performed in the same manner as Step B-3 mentioned above.

The compounds of this invention have potent pharmacological activities, such as platelet aggregation and adhesion-inhibiting, vasodilating, gastric acid secretion-inhibiting, gastric cytoprotective, bronchodilating, luteolytic, and uterine constricting activities.

The present compounds have potent platelet aggregation and adhesion-inhibiting, vasodilating, and lipid-, cholesterol- and neutral fat-degradation activities, and they may be useful for prophylactic and/or therapeutic treatment of such diseases as hypertension, myocardial infarction, angina pectoris, ischemic cerebral diseases (e.g., cerebral infarction), TIA, peripheral circulatory disturbance (Burger's disease, Raynaus disease, Behcet disease, thrombocytopenic purpura, arteriovenous fistula, hepatopathy, nephropathy, etc.), atherosclerosis, arteriosclerosis, diabetic platelet dysfunctions, retinal vascular obstruction, hyperlipidemia, and vibration diseases.

For these applications, the compounds of this invention may usually be administered to a subject either parenterally by intravenous, intra-arterial, intramuscular, intradermal or subcutaneous injection, or orally.

When administered orally or intrarectally, a daily dose in the range of 0.01 $\mu$g/kg to 10 mg/kg may usually be used at one to four times a day. When injected intravenously by dripping or intra-arterially, dose rates in the range of 0.1 ng/kg to 1 $\mu$g/kg per minute may cause good results. In cases of usual intravenous, intramuscular or subcutaneous injection, a daily dose in the range of 0.01 $\mu$g/kg to 10 mg/kg may be applied at one to four times a day. Every particular dose amount of the present compound should be selected from the above specified range according to the age, sex and physical conditions of a patient and to the frequency of drug administration. If administered intradermally, dose amounts may vary with different dosage forms of drugs but should be adjusted so that the daily intake of the present compound may fall within the range of from 0.001 $\mu$g to 10 mg per kg of body weight.

The compounds of this invention may be used to preserve platelets. For this application, the compound is added to a concentrated platelet suspension in an amount of 0.01 ng to 1 $\mu$g per ml of the suspension.

The compounds of this invention may be effective for the prevention of platelet aggregation and/or adhesion upon clinical use of an artificial heart and lung, kidney, liver, valve or blood vessel. For this application, the compounds may be administered orally or by injection. When orally administered, effective results may be attained with a dose of the present compound in the range of 0.01 $\mu$g/kg to 10 mg/kg. The compounds may also be effectively infused into an inlet of the circuit of an artificial organ at a rate of 0.01 ng/kg to 1 mg/kg per minute.

The compounds of this invention may also be effective for the prophylactic and/or therapeutic treatment of duodenal ulcer, gastric ulcer, chronic gastritis, and/or digestive organ disorders induced by non-steroidal antiinflammatory and/or analgesic drugs. When the present compounds are orally or intravenously administered for this indication, an appropriate dose amount should be chosen from the range of 0.01 $\mu$g/kg to 1 mg/kg per day. Adequate schedule of drug aministration is one to four times a day.

The present compounds may also be effective for amelioration of respiratory disorders associated with such diseases as asthma, bronchitis and pneumonia. For this indication, the compound of this invention may be administered orally or by inhalationn at a dose amount in the range of 0.001 μg/kg to 1 mg/kg.

In addition, the present compounds may be effective for the induction of labor and/or the relaxation and softening of uterine cervix. For this indication, the present compound may preferably be administered orally, intravaginally or by intravenous infusion. When administered orally or intravaginally, a dose amount in the range of 0.01 μg/kg to 5 mg/kg may be employed. Intravenous drip may be effected at a rate of 0.01 ng/kg to 1 μg/kg per minute.

The compounds of this invention may also be useful for the synchronization of estrous cycle in mammal, e.g., horse, cow, pig, sheep, etc. For these applications, 0.01 μg/kg to 10 mg/kg of the present compound may usually be administered orally, intravaginally or intramuscularly.

Further, the compounds of this invention may be effective for the obliteration or treatment of congestion of nasal mucosa. For these purposes, an aerosol solution of 0.1 μg/ml to 10 mg/ml of the present compound may locally be applied; or alternatively, an ointment, lotion or liniment containing 0.01 μg/ml to 1 mg/ml of the compound may be administered locally.

The compounds of this invention may also be effective for the improvement of symptoms of hepatitis or nephritis. For these indications, the compound may be orally or intravenously administered at a dose amount in the range of 0.01 μg/kg to 1 mg/kg.

In addition, the compounds of this invention may also be useful for the prevention of cancer metastasis. For this purpose, the present compound may be orally or intravenously administered one to four times a day at a daily dose of 0.01 μg/kg to 1 mg/kg. The compounds may also be administered by intravenous drip at a rate of 0.01 ng/kg to 100 μg/kg per minute.

Furthermore, the present compounds may be useful as anti-inflammatory and/or analgesic agents. For these indications, the compound may be orally or intravenously administered at a daily dose amount of 0.01 μg/kg to 1 mg/kg.

Dosage forms for oral administration are solids containing, in addition to one or more compounds of this invention, at least one suitable carrier such as starch, lactose, sucrose, glucose, microcrystalline cellulose, a clay-like vehicle, a coloring agent, a lubricant, a binder, a disintegrator, or a coating material. The present compounds can also be parenterally administered in the form of sterilized solutions which may optionally contain an amount of another solute, such as sodium chloride or glucose, sufficient to make them iso-osmotic.

Because of the excellent stability of the chemical structure, the present compounds can be formulated into a wide variety of dosage forms, such as above-mentioned oral formulations (e.g., tablets, powders, granules, etc.), various injectable solutions, suppositories, ointments, lotions, and the like.

The present invention will be illustrated by the following examples and reference examples. These examples are given by way of illustration only and should not be construed as limiting this invention.

REFERENCE EXAMPLE 1:

7-Bromo-2α-hydroxy-1β-hydroxmethyl-3aβH, 8bβH-2,3,3a,8b-tetrahydro-5-1H-cyclopenta[b]benzofurancarbaldehyde (1)

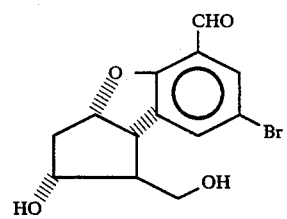

A solution of cyclohexylmagnesium chloride in THF (1.85N, 327 ml, 605 mmol) was added to a solution of 5,7-dibromo-2α-hydroxy-1β-hydroxymethyl-3aβH,8bβH-2,3,3a,8b-tetrahydro-1H-cyclopenta[b]benzofuran (100 g, 275 mmol) in anhydrous THF (900 ml) at 0° C. under argon atmosphere. The reaction mixture was then stirred at room temperature for 10 minutes. The above mentioned Grignard reagent (273 ml, 505 mmol) was further added to the reaction mixture. The mixture was then stirred at 40° C. for 2 hours. At room temperature, anhydrous DMF (150 ml) was dropwise added to the reaction mixture and stirred for 30 minutes. The resulting reaction mixture was cooled to 0° C., and ether (800 ml) and hydrochloric acid (3N, 600 ml) were added. The mixture was five times extracted with ethyl acetate. The organic layers were combined, washed with saturated aqueous sodium hydrogencarbonate solution and with brine (saturated aqueous sodium chloride solution), and dried over magnesium sulfate to concentrate. The residue was recrystallized from ethyl acetate, yielding 7-bromo-2α-hydroxy-1β-hydroxymethyl-3aβH,8bβH-2,3,3a,8b-tetrahydro-5-1H-cyclopenta[b]benzofurancarbaldehyde (52.3 g, 167 mmol). The mother liquor was again concentrated and the residue was recrystallized from ethyl acetate, yielding the above mentioned aldehyde (16.5 g, 52.7 mmol). The total yield was 80%.

Melting Point: 143°–144° C.

IR (KBr): 3440, 3050, 2960, 2890, 2740, 1680, 1595, 1580, 1440, 1385, 1325, 1220, 1200, 1100, 1070, 1045, 1010, 950, 900, 870, 830, 780, 740, 695, 600, 560, 515 cm$^{-1}$.

NMR (90 MHz, DMSO-d$_6$, δ): 1.7–2.5 (3H, m); 3.2–4.0 (4H, m); 4.5–4.9 (2H, m); 5.37 (1H, ddd, J=4.6, 7.2, 9.0 Hz); 7.5–7.7 (2H, m); 10.02 (1H, s).

MASS (EI, m/e): 314 (M+).

Elementary Analysis (C$_{13}$H$_{13}$O$_4$Br): Calcd. (%): C 49.86; H 4.19; Br 25.52, Found (%): C 49.75; H 4.30; Br 25.48.

REFERENCE EXAMPLE 2: Methyl 2α-hydroxy-1β-hydroxymethyl-3aβH,8bβH-2,3,3a,8b-tetrahydro-5-1H-cyclopenta[b]benzofuranpropionate (2)

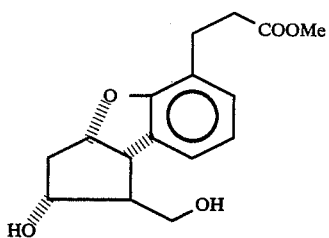

At −10° C., a solution of n-butyllithium in hexane (1.66 N, 134 ml, 223 mmol) was added to a solution of diisopropylamine (31.2 ml, 223 mmol) in anhydrous THF (400 ml) and the mixture was stirred for 30 minutes. After the reaction mixture was cooled to −78° C., anhydrous ethyl acetate (21.9 ml, 223 mol) was added and the mixture was stirred for 30 minutes. A solution of 7-bromo-2α-hydroxy-1β-hydroxmethyl-3aβH,8bβH-2,3,3a,8b-tetrahydro-5-1H-cyclopenta[b]benzofurancarbaldehyde (10g, 31.9 mmol) in anhydrous HMPA (100 ml) was dropwise added over about 5 minutes so that the reaction temperature should not exceed −60° C. After the reaction mixture was stirred for 10 minutes, ether (300 ml) and hydrochloric acid (3N, 180 ml) were added and further stirred. The mixture was three times extracted with ethyl acetate. The organic layers were combined, and washed with saturated aqueous sodium hydrogensulfite solution and with water to remove unreacted aldehyde. The mixture was then washed with saturated aqueous sodium hydrogencarbonate solution, with water and with brine, and dried to concentrate, yielding an oily material (20 g).

The oily material was dissolved in methanol (100 ml). To the resulting solution 10% palladium/carbon (4 g) was added as a catalyst, and the reaction mixture was stirred under hydrogen atmosphere for 20 hours. The reaction mixture was filtered and an aqueous solution of sodium hydrogencarbonate was added to the filtrate. After the resulting mixture was concentrated, water was added to the residue. The mixture was extracted with ethyl acetate. The organic layer was then washed with water and with brine, and dried over magnesium sulfate to concentrate. The residue was dissolved in anhydrous methanol (100 ml) and sodium methoxide (4.89N, 1.6 ml) was added. The mixture was stirred at room temperature for 3 hours. Acetic acid (0.58 ml) was then added to the reaction mixture. After concentration, the residue was dissolved in ethyl acetate. This solution was washed with saturated aqueous sodium hydrogencarbonate solution, with water and with brine, and dried to concentrate. The resulting oily material was purified by column chromatography with ethyl acetate/cyclohexane (1/1), yielding methyl 2α-hydroxy-1β-hydroxymethyl-3aβH,8bβH-2,3,3a,8b-tetrahydro-5-1H-cyclopent[b]benzofuranpropionate (6.91 g, 74% yield).

Melting Point: 88.5°–90.0° C. (recrystallized from ethyl acetate/cyclohexane).

IR (KBr): 3400, 2960, 2910, 2860, 1700, 1590, 1470, 1440. 1360, 1330, 1290; 1280, 1220, 1185, 1105, 1055, 1010, 980, 950, 915, 895, 850, 835, 805, 770, 745, 590, 450, 340 cm$^{-1}$.

NMR (400 MHz, CDCl$_3$, ε): 1.97 (1H, ddd, J=5.4, 8.3, 13.7 Hz); 2.05 (1H, dq, J=5.4, 7.8 Hz); 2.51 (1H, dt, J=6.8, 13.7 Hz); 2.5–2.7 (2H, m); 2.8–3.0 (2H, m); 3.15 (1H, broad s); 3.2 (1H, m); 3.38 (1H, dd, J=7.8, 8.6 Hz); 3.64 (3H, s); 3.65–3.7 (1H, m); 3.8–3.9 (1H, m); 4.0–4.1 (1H, m); 5.08 (1H, ddd, J=5.4, 6.8, 8.6 Hz); 6.76 (1H, dd, J=6.8, 7.3 Hz); 6.94 (1H, d, J=6.8 Hz); 7.02 (1H, d, J=7.3 Hz).

MASS (EI, m/e): 292 (M+).

Elementary Analysis (C$_{16}$H$_{20}$O$_5$): Calcd. (%): C 65.74; H 6.90, Found (%): C 65.71; H 6.90.

REFERENCE EXAMPLE 3: Methyl 2α-acetoxy-1β-hydroxymethyl-3aβH,8bβH-2,3,3a,8b-tetrahydro-5-1H-cyclopenta[b]benzofuranpropionate (3)

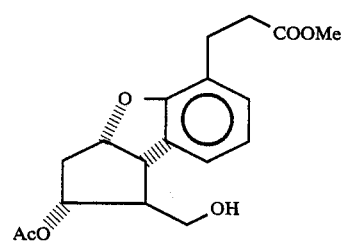

To a solution of methyl 2α-hydroxy-1β-hydroxymethyl-3aβH,8bβH-2,3,3a,8b-tetrahydro-5-1H-cyclopenta[b]benzofuranpropionate (46 g, 158 mmol) in anhydrous THF (600 ml), there were added anhydrous triethylamine (88 ml, 632 mmol) and trityl chloride (88 g, 316 mmol). The mixture was heated under reflux for 6 hours. Anhydrous pyridine (165 ml, 2.05 mol) and acetic anhydride (193 ml, 2.05 mol) were added to the reaction mixture and the resulting mixture was stirred at room temperature for 48 hours. The reaction mixture was cooled to 0° C. and methanol/hydrochloric acid (5.5 N, 500 ml) was added. The mixture was then stirred at room temperature for 8 hours. Subsequently, the reaction mixture was cooled to 0° C., and sodium hydrogencarbonate (280 g) was added to adjust the pH to approximately 6. After concentration, ethyl acetate (800 ml) was added to the residue, and the mixture was filtered. The filtrate was washed with 6N hydrochloric acid, with water and with brine, and dried over magnesium sulfate to concentrate. The residue was purified by column chromatography using silica gel (1 kg) with ethyl acetate/cyclohexane (1/3), yielding methyl 2α-acetoxy-1β-hyddroxymethyl-3aβH,8bβH-2,3,3a,8b-tetrahydro-5-1H-cyclopenta[b]benzofuranpropionate (43.2 g, 82% yield).

Melting Point: 56°–57° C. (recrystallized from ether/hexane).

IR (KBr): 3530, 3480, 3050, 2950, 2875, 1720, 1600, 1455, 1375, 1330, 1245, 1200, 1170, 1080, 1060, 1010, 980, 940, 850, 790, 760, 740, 650, 610, 530, 390, 325 cm$^{-1}$.

NMR (400 MHz, CDCl$_3$, δ): 1.83 (3H, s); 2.1–2.3 (3H, m); 2.55 (1H, dt, J=6.3, 14.2 Hz); 2.6–2.8 (2H, m); 2.8–3.0 (2H, m); 3.6–3.8 (3H, m); 3.67 (3H, s); 5.07 (1H, q, J=6.3 Hz); 5.20 (1H, ddd, J=3.4, 6.3, 8.3 Hz); 6.77 (1H, t, J=7.3 Hz); 6.96 (1H, d, J=7.3 Hz); 7.05 (1H, d, J=7.3 Hz).

MASS (EI, m/e): 334 (M+).

Elementary Analysis (C$_{18}$H$_{22}$O$_6$): Calcd. (%): C 64.65; H 6.63, Found (%): C 64.62; H 6.62.

REFERENCE EXAMPLE 4: Ethyl 2,2-dimethyl-4-hexynoate (4)

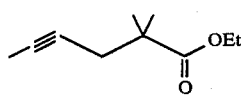

Under argon atmosphere, a solution of n-butyllithium in hexane (1.64 N, 26 ml, 0.043 mol) was dropwise added to a solution of anhydrous diisopropylamine (4.3 g, 0.043 mol) in anhydrous THF (35 ml) with stirring at −20° C., and the mixture was further stirred for 30 minutes. To the reaction mixture, there were added dropwise at −20° C. a solution of ethyl 2-methyl-4-hexynoate (5.4 g, 0.035 mol) in anhydrous THF (15 ml) and anhydrous HMPA (2.25 ml, 0.013 mol). The reaction mixture was stirred at room temperature for 40 minutes. Then, it was cooled to −30° C., and a solution of methyl iodide (6.05 g, 0.043 mol) in anhydrous THF (5 ml) was dropwise added. The reaction mixture was warmed to room temperature and stirred for one hour. Acetic acid (2.5 ml, 0.043 mol) was added to the mixture. After concentration, water (50 ml) was added to the residue and the mixture was extracted with ethyl acetate (100 ml×2). The organic layers were combined, washed with water (30 ml) and with brine (20 ml), and dried over anhydrous sodium sulfate to concentrate. Vacuum distillation of the residue (b.p.=65°−68° C. at 10 mmHg) gave ethyl, 2,2-dimethyl-4-hexynoate (3.7 g, 0.022 mol, 62% yield). The above described structure of this product was confirmed by the following data.

IR (Liquid Film): 2980, 2925, 2870, 2230, 1715, 1465, 1380, 1360, 1310, 1300, 1250, 1190, 1130, 1025, 980, 945, 910, 860, 770, 740 cm$^{-1}$.

NMR (90 MHz, CDCl$_3$, δ): 1.1–1.4 (9H, m); 1.77 (3H, t, J=2.5 Hz); 2.36 (2H, q, J=2.5 Hz); 4.14 (2H, q, J=7.1 Hz).

MASS (EI. m/e): 168 (M+).

REFERENCE EXAMPLE 5: Dimethyl 3,3-dimethyl-2-oxo-5-heptynylphosphonate (5)

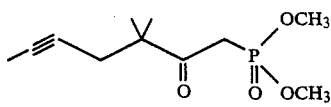

Under argon atmosphere, a solution of n-butyllithium in hexane (1.64 N, 33 ml, 0.054 mol) was slowly added dropwise to a solution of dimethyl methylphosphonate (6.82 g, 0.055 mol) in anhydrous THF (100 ml) with stirring at −78° C., and the mixture was further stirred for 30 minutes. To the reaction mixture, there was added dropwise a solution of ethyl 2,2-dimethyl-4-hexynoate (3.7 g, 0.022 mol) in anhydrous THF (15 ml). The reaction mixture was stirred at −78° C. for 30 minutes and then at room temperature for one hour. Acetic acid (3.1 ml, 0.054 mol) and water (10 ml) were added to the reaction mixture. After concentration, water (20 ml) was added to the residue and the mixture was extracted with ethyl acetate (100 ml×2). The organic layers were combined, washed with water (20 ml) and with brine (20 ml), and dried over anhydrous sodium sulfate to concentrate. Vacuum distillation of the residue (b.p.=108°−110° C. at 0.15 mmHg) gave di-methyl 3,3-dimethyl-2-oxo-5-heptynylphosphonate (5.04 g, 0.020 mol, 93% yield). The structure was confirmed by the following data.

IR (Liquid Film): 3450, 2950, 2905, 2850, 2220, 1700, 1455, 1375, 1355, 1240, 1175, 1020, 860, 835, 800, 710 cm$^{-1}$.

NMR (90 MHz, CDCl$_3$, δ): 1.23 (6H, m); 1.77 (3H, t, J=2.5 Hz); 3.24 (2H, d, J=21.3 Hz); 2.34 (2H, q, J=2.6 Hz); 3.80 (6H, d, J=11.2 Hz).

MASS (EI, m/e): 246 (M+).

REFERENCE EXAMPLE 6: 2-Pentyne-1-ol (6)

A piece of lithium and a piece of ferric nitrate were added to liquid ammonia (500 ml) and the reaction mixture was stirred until the blue color thereof disappeared. Further, lithium (8 g, 1.16 mol) was slowly added and the mixture was stirred for one hour. 2-Propyne-1-ol (16.3 g, 0.29 mol) was added to the reaction mixture followed by further stirring for 30 minutes. Then, ethyl bromide (37.6 g, 0.35 mol) was added and the resulting mixture was stirred for 20 minutes. Excess ammonium chloride was added to the reaction mixture and remaining liquid ammonia was then distilled out. Water (100 ml) was added to the residue and the mixture was filtered. The filtrate was extracted with ether (150 ml×7). The organic layers were combined, washed with brine (150 ml), and dried over anhydrous sodium sulfate. After ether was distilled out under normal pressure, vacuum distillation of the residue (b.p.=62°−65° C. at 20 mmHg) gave 2-pentyne-1-ol (14.1 g, 0.17 mol, 57.9% yield). The structure was confimed by the following data.

IR (Liquid Film): 3300, 2970, 2930, 2875, 2295, 2225, 1450, 1415, 1315, 1225, 1130, 1060, 1005, 945, 780, 730 cm$^{-1}$.

NMR (90 MHz, CDCl$_3$, δ): 1.12 (3H, t, J=7.4 Hz); 1.8–2.4 (3H, m); 4.22 (2H, t, J=2.7 Hz).

MASS (EI, m/e): 84 (M+).

REFERENCE EXAMPLE 7: 1-Bromo-2-pentyne (7)

Under argon atmosphere, pyridine (1.2 ml) and phosphorus tribromide (16.2 g, 0.06 mol) were added to a solution of 2-pentyne-1-ol (14 g, 0.17 mol) in anhydrous ether (60 ml) with stirring at −30° C., and the mixture was stirred for 2 hours. The reaction mixture was further stirred at room temperature for an additional one hour, washed with brine (110 ml), and dried over anhydrous magnesium sulfate. After ether was distilled out at normal pressure, vacuum distillation of the residue (b.p.=80°−83° C. at 80 mmHg) gave 1-bromo-2-pentyne (12.8 g, 0.087 mol, 52.3% yield). The structure was confirmed by the following data.

IR (Liquid Film): 2980, 2940, 2880, 2850, 2320, 2240, 1445, 1420, 1370, 1315, 1205, 1150, 1055, 950, 860, 710, 610 cm$^{-1}$.

NMR (90 MHz, CDCl$_3$, δ): 1.14 (3H, t, J=7.5 Hz); 2.26 (2H, tq, J=2.3, 7.5 Hz); 3.92 (2H, t, J=2.3 Hz).

MASS (EI, m/e): 146 (M+).

REFERENCE EXAMPLE 8: Ethyl 2-methyl-4-heptynoate (8)

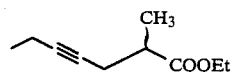

Under argon atmosphere, 60% dispersion of sodium hydride (4.6 g, 0.114 mol) in mineral oil was suspended in anhydrous THF (200 ml), and a solution of diethyl methylmalonate (20.0 g, 0.114 mol) in anhydrous THF (20 ml) was dropwise added over one hour with stirring at room temperature. To this reaction mixture, there was added dropwise a solution of 1-bromo-2-pentyne (14.0 g, 0.095 mol) in anhydrous THF (15 ml) at room temperature over 20 minutes. Water (30 ml) was added to the reaction mixture and 3N hydrochloric acid was then added to neutralize. After concentration, the residue was extracted with ethyl acetate (200 ml×2). The organic layer were combined, washed with water (50 ml) and with brine (30 ml), and dried over anhydrous sodium sulfate to concentrate, yielding crude ethyl 2-carboethoxy-2-methyl-4-heptynoate (26.0 g).

To a solution of the crude material in ethanol (200 ml), there was added an aqueous sodium hydroxide solution (0.994 N, 169 ml, 0.168 mol) with stirring under ice-cooling. The reaction mixture was further stirred at room temperature for 14 hours. Water (30 ml) was added to the mixture followed by concentration. Hydrochloric acid (6N) was added to neutralize under ice-cooling. The mixture was then extracted with ethyl acetate (100 ml×3). The organic layers were combined, washed with brine (50 ml), and dried over anhydrous sodium sulfate to concentrate, yielding crude 2-carboethoxy-2-methyl-4-heptynoic acid (22.1 g).

The crude product was heated at 180° C. for 2 hours and then dissolved in ether (100 ml). An excess solution of diazomethane in ether was added. After concentration, vacuum distillation of the residue (b.p.=118°–125° C. at 56 mmHg) gave ethyl 2-methyl-4-heptynoate (12.21 g, 0.073 mol, 76% yield) which contained 10% of methyl 2-methyl-4-heptynoate.

IR (Liquid Film): 2975, 2940, 2880, 2850, 1730, 1450, 1365, 1340, 1310, 1275, 1240, 1170, 1110, 1040, 1010, 920, 8550, 780 cm$^{-1}$.

NMR (90 MHz, CDCl$_3$, δ): 1.10 (3H, t, J=7.2 Hz); 1.22 (3H,d, J=7.3 Hz); 1.27 (3H, t, J=6.2 Hz); 1.9–2.8 (5H, m); 4.15 (2H, q, J=7.2 Hz).

MASS (EI, m/e): 168 (M+).

REFERENCE EXAMPLE 9: Dimethyl 3-methyl-2-oxo-5octynylphosphonate (9)

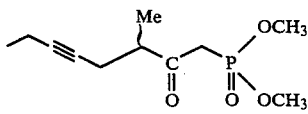

Under argon atmosphere, a solution of n-butyllithium in hexane (1.71 N, 43 ml, 0.074 mol) was dropwise added to a solution of dimethyl methylphosphonate (7.91 ml, 0.074 mol) in anhydrous THF (150 ml) with stirring at −78° C., and the mixture was further stirred for 30 minutes. Then, a solution of ethyl 2-methyl-4-heptynoate (5.0 g, 0.03 mol) in anhydrous THF (5 ml) was dropwise added to the reaction mixture and the whole mixture was stirred for 30 minutes. The reaction mixture was further stirred at room temperature for 30 minutes. Then, acetic acid (4.5 ml) and water (10 ml) were added under ice-cooling. After concentration, water (20 ml) was added to the residue and the mixture was extracted with ethyl acetate (50 ml×2). The organic layers were combined, washed with water (20 ml) and with brine (20 ml), and dried over anhydrous sodium sulfate to concentrate. Vacuum distillation of the residue (b.p.=118°–121° C. at 0.35 mmHg) gave dimethyl -methyl-2-oxo-5-octynylphosphonate (6.55 g, 0.027 mol, 88% yield). The structure was confirmed by the following data.

IR (Liquid Film): 3450, 2960, 2850, 1700, 1450, 1390, 1370, 1350, 1310, 1250, 1170, 1030, 870, 830, 805, 720 cm$^{-1}$.

NMR (90 MHz, CDCl$_3$, δ): 1.1 (3H, t, J=7.4 Hz); 1.19 (3H, d, J=6.8 Hz); 1.9–2.5 (4H, m); 2.7–3.1 (1H, m); 3.0–3.4 (2H, m); 3.79 (6H, d, J=11.2 Hz).

MASS (EI, m/e): 246 (M+).

REFERENCE EXAMPLE 10: 2-Hexyne-1-ol (10)

Under nitrogen atmosphere, a piece of lithium and a piece of ferric nitrate were added to liquid ammonia (500 ml) with stirring. After the disappearance of the blue color was observed, lithium (8.0 g, 1.16 mol) was slowly added. The reaction mixture was stirred for one hour. To the reaction mixture 2-propyne-1-ol (16.3 g, 0.29 mol) was added, and the whole mixture was stirred for 30 minutes. Propyl bromide (42.8 g, 0.348 mol) was then added and the mixture was stirred for 20 minutes. An excess amount of ammonium chloride was then added to the reaction mixture. After liquid ammonia was distilled out, water (200 ml) was added to the residue and the mixture was filtered. The filtrate was extracted with ether (150 ml×6). The ether layers were combined, washed with brine (150 ml), and dried over anhydrous magnesium sulfate. Ether was distilled out at normal pressure. The residue was subjected to vacuum distillation (b.p.=80°–85° C. at 20 mmHg), yielding 2-hexyne-1-ol (24.1 g, 0.246 mol, 84.8% yield). The structure of this product was confirmed by the following data.

IR (Liquid Film): 3320, 2960, 2930, 2870, 2280, 2230, 1455, 1430, 1375, 1355, 1335, 1275, 1225, 1135, 1070, 1035, 1010, 885 cm$^{-1}$.

NMR (90 MHz, CDCl$_3$, δ): 0.976 (3H, t, J=7.0 Hz); 1.3–1.8 (2H, m); 1.86 (1H, s); 2.0–2.4 (2H, m); 4.25 (2H, m).

MASS (EI, m/e): 98 (M+).

REFERENCE EXAMPLE 11: 1-Bromo-2-hexyne (11)

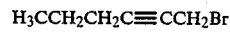

Under argon atmosphere, pyridine (1.8 ml, 0.022 mol) was added to a solution of 2-hexyne-1-ol (24 g, 0.245 mol) in anhydrous ether (70 ml) with stirring at −30° C., and phosphorus tribromide (23.8 g, 0.088 mol) was then added dropwise. The mixture was further stirred at −30° C. for 2 hours, and then at room temperature for one hour. To the reaction mixture brine (160 ml) was added, and the mixture was extracted with ether. After the ether layer was dried over anhydrous magnesium sulfate, ether was distilled out at normal atmospheric pressure. Vacuum distillation of the residue (b.p.=92°-100° C. at 75 mmHg) gave 1-bromo-2-hexyne (26.6 g, 0.175 mol, 71.4% yield) as a colorless, transparent liquid. The structure of this product was confirmed by the following data.

IR (Liquid Film): 2960, 2930, 2870, 2830, 2300, 2220, 1450, 1420, 1370, 1330, 1270, 1200, 1145, 1090, 1070, 1025, 880, 860 cm$^{-1}$.

NMR (90 MHz, CDCl$_3$, δ): 0.981 (3H, t, J=7.2 Hz); 1.3–1.8 (2H, m); 2.0–2.4 (2H, m); 3.93 (2H, t, J=2.3 Hz).

MASS (EI, m/e): 160 (M$^+$).

REFERENCE EXAMPLE 12: Ethyl 2-methyl-4-octynoate (12)

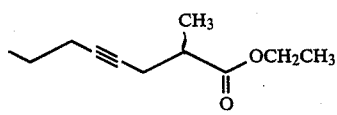

Under argon atmosphere, 60% dispersion of sodium hydride (4.88 g, 0.122 mol) in mineral oil was suspended in anhydrous THF (200 ml) and a solution of diethyl methylmalonate (21.4 g, 0.122 mol) in anhydrous THF (20 ml) was dropwise added at room temperature over one hour. To this reaction mixture, there was dropwise added a solution of 1-bromo-2-hexyne (18.0 g, 0.188 mol) in anhydrous THF (20 ml) at room temperature. Water (50 ml) was added to the reaction mixture and 1N hydrochloric acid was added to neutralize. After concentration, water (50 ml) was added to the residue and the resulting mixture was extracted with ethyl acetate (200 ml×2). Ethyl acetate layers were combined, washed with water (50 ml) and with brine (50 ml), and dried over anhydrous sodium sulfate to concentrate, yielding an oily material (30.5 g).

To a solution of this oily material in ethanol (200 ml), an aqueous sodium hydroxide solution (1N, 180 ml, 0.18 mmol) was added with stirring under ice-cooling. The mixture was then stirred at room temperature for 6 hours. This reaction mixture was neutralized with 6N hydrochloric acid and concentrated. After water (100 ml) was added, the resulting mixture was extracted with ethyl acetate (200 ml×2). Ethyl acetate layers were combined, washed with water (50 ml) and with brine (50 ml), and dried over anhydrous sodium sulfate to concentrate.

The resultant residue was heated at 180° C. for 2 hours and dissolved in ether (100 ml). To this solution, an excess amount of a solution of diazomethane in ether was added with stirring under ice-cooling. After concentration, the residue was subjected to vacuum distillation (b.p.=115°-121° C. at 35 mmHg), yielding ethyl 2-methyl-4-octynoate (16.9 g, 0.093 mol, 77.4% yield) which contained 13% of methyl 2-methyl-4-octynoate. The above described structure of the desired product was confirmed by the following data.

IR (Liquid Film): 2970, 2930, 1735, 1455, 1375, 1340, 1275, 1250, 1180, 1050, 1020, 860 cm$^{-1}$.

NMR (90 MHz, CDCl$_3$, δ): 0.96 (3H, t, J=7.4 Hz); 1.26 (3H, t, J=7.2 Hz); 1.24 (3H, d, J=6.6 Hz); 1.1–1.8 (2H, m); 1.9–2.3 (2H, m); 2.3–2.8 (3H, m); 4.15 (2H, q, J=7.2 Hz).

MASS (EI, m/e): 182 (M$^+$).

REFERENCE EXAMPLE 13: Dimethyl 3-methyl-2-oxo-5-nonanylphosphonate (13)

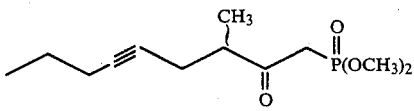

Under argon atmosphere, a solution of n-butyllithium in hexane (1.58N, 41.8 ml, 0.066 mol) was dropwise added to a solution of dimethyl methylphosphonate (8.2 g, 0.066 mol) in anhydrous THF (120 ml) with stirring at −78° C., and the mixture was further stirred for 30 minutes. To the mixture there was dropwise added a solution of ethyl 2-methyl-4-octynoate (5.0 g, 0.0275 mol) containing 13% of methyl 2-methyl-4-octynoate in anhydrous THF (10 ml), and the whole mixture was stirred for 30 minutes. At 0° C., acetic acid (4 ml) and water (20 ml) were added to the reaction mixture followed by concentration. After water (30 ml) was added to the residue, the mixture was extracted with ethyl acetate (50 ml×2). Ethyl acetate layers were combined, washed with water (20 ml) and with brine (20 ml), and dried over anhydrous sodium sulfate to concentrate. The residue was subjected to vacuum distillation (b.p.=127°-130° C. at 0.22 mmHg), yielding dimethyl 3-methyl-2-oxo-5-nonanylphosphonate (6.82 g, 0.026 mol, 95.4% yield) as a colorless, transparent oil. The structure of this product was confirmed by the following data.

IR (Liquid Film): 3450, 2950, 2920, 2870, 1710, 1450, 1390, 1370, 1350, 1330, 1260, 1180, 1020, 870, 825, 810, 730, 680 cm$^{-1}$.

NMR (90 MHz, CDCl$_3$, δ): 0.96 (3H, t, J=7.2 Hz); 1.20 (3H, d, J=6.8 Hz); 1.3–1.7 (2H, m); 1.9–2.2 (2H, m); 2.2–2.5 (2H, m); 2.7–3.1 (1H, m); 3.20 (2H, d, J=22.2 Hz); 3.79 (6H, d, J=11.2 Hz).

MASS (EI, m/e): 260 (M$^+$).

REFERENCE EXAMPLE 14: 2-Heptyne-1-ol (14)

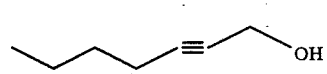

Under argon atmosphere, a small amount of lithium pieces was added to liquid ammonia (350 ml). The color of the liquid became dark blue. This color gradually faded upon addition of a catalytic amount of ferric nitrate nonahydrate. Lithium pieces (4.56 g, 657 mmol) were added over 30 minutes and the resulting mixture was further stirred for one hour. Then, propargyl alcohol (14.73 g, 263 mmol) was added and the mixture was stirred for 30 minutes. After n-butyl bromide (30 g, 219 mmol) was also added, the reaction mixture was stirred for 10 minutes. The reaction mixture was allowed to stand overnight at room temperature to remove out liquid ammonia. To the reaction mixture, there were added water-containing ether (50 ml) and water (200 ml). The mixture was extracted with ether (200 ml, 100 ml×2). The organic layers were combined, washed with water (400 ml) and with brine (400 ml), and dried over anhydrous magnesium sulfate (50 g) to concentrate. The residue was distilled (b.p.=55°-58° C. at 0.18 mmHg), yielding a colorless oil, 2-heptyne-1-ol (17.6373 g, 61% yield). The above described structure of this product was confirmed by the following data.

IR (Liquid Film): 3325, 2950, 2920, 2860, 2275, 2220, 1460, 1430, 1380, 1359, 1325, 1300, 1248, 1226, 1135, 1103, 1023, 1010, 925, 880 cm$^{-1}$.

NMR (100 MHz, CDCl$_3$, δ): 0.72–1.08 (3H, m); 1.08–1.69 (4H, m); 2.03–2.37 (2H, m); 2.09 (1H, broad s); 4.24 (2H, t, J=2.2 Hz).

MASS (EI, m/e): 112 (M+).

REFERENCE EXAMPLE 15: 1-Bromo-2-heptyne (15)

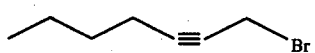

Under argon atmosphere, anhydrous pyridine (1.28 ml, 15.9 mmol) was added to a solution of 2-heptyne-1-ol (17.4373 g, 159 mmol) in anhydrous ether (100 ml). Subsequently, phosphorus tribromide (7.45 ml, 79.3 mmol) was dropwise added at −30° C. to 35° C. and the resulting mixture was stirred for one hour. Then, the reaction mixture was further stirred at room temperature for 30 minutes. Brine (100 ml) was then added to the reaction mixture. After the mixture was extracted with ether (50 ml×4), the organic layers were combined, washed with saturated aqueous sodium hydrogencarbonate solution (150 ml), with water (150 ml) and with brine (150 ml), and dried over anhydrous magnesium sulfate (50 g) to concentrate. The residue was distilled (b.p.=41°–43° C. at 0.18 mmHg), yielding a colorless oil, 1-bromo-2-heptyne (12.4487 g, 47% yield). The structure of this product was confirmed by the following data.

IR (Liquid Film): 2950, 2925, 2870, 2310, 2225, 1450, 1424, 1375, 1322, 1300, 1250, 1203, 1147, 1100, 959, 927, 882, 862, 702, 608 cm$^{-1}$.

NMR (100 MHz, CDCl$_3$, δ): 0.73–1.02 (3H, m); 1.08–1.69 (4H, m); 2.05–2.39 (2H, m); 3.93 (2H, t, J=2.2 Hz).

MASS (EI, m/e): 174 (M+).

REFERENCE EXAMPLE 16: Ethyl 2-methyl-4-nonynoate (16)

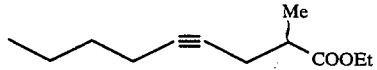

Under argon atmosphere, 60% dispersion of sodium hydride (4.036 g, 101 mmol) in mineral oil was suspended in anhydrous THF (90 ml). A solution of diethyl methylmalonate (18.59 g, 108 mmol) in anhydrous THF (15 ml) was added to the suspension at room temperature, and the mixture was stirred for 20 minutes. The reaction mixture was cooled with ice, and a solution of 1-bromo-2-heptyne (12.6121 g, 72.1 mmol) in anhydrous THF (10 ml) was added. The reaction mixture was then stirred at room temperature for 30 minutes. Hydrochloric acid (3N, 40 ml) was added. After concentration, water (40 ml) was added to the residue and the resulting mixture was extracted with ethyl acetate (40 ml×3). The organic layers were combined, washed with saturated aqueous sodium hydrogencarbonate solution (100 ml), with water (100 ml) and with brine (100 ml), and dried over anhydrous magnesium sulfate (40 g) to concentrate, yielding an oily material (27.83 g).

To a solution of this oily material in ethanol (200 ml), there was added an aqueous sodium hydroxide solution (1N, 170 ml, 170 mmol), and the mixture was stirred under argon atmosphere at room temperature for 46 hours and a half. Hydrochloric acid (3N, 140 ml) was added to the reaction mixture. After concentration, the residue was extracted with ethyl acetate (100 ml, 70 ml×2). The organic layers were combined, washed with water (150 ml×2) and with brine (150 ml), and dried over anhydrous magnesium sulfate (60 g) to concentrate, yielding an oily product (21.6118 g).

This oily product was heated under argon atmosphere at 180°–190° C. for 2 hours and diluted with ether (20 ml). The product was esterified with diazomethane under ice-cooling. Concentration of the esterified product yielded an oil (14.3957 g). Distillation of the oil (b.p.=65°–70° C. at 0.18 mmHg) gave a colorless oil, ethyl 2-methyl-4-nonynoate (13.641 g, 90% yield). The ratio of the ethyl ester to methyl ester in the final product was 25:1 according to GLC on 3% OV-17 with column temperature of 60° C. and inlet temperature of 180° C. The structure of the ethyl ester was confirmed by the following data. (NMR and MASS data are shown only for the ethyl ester.)

IR (Liquid Film): 2950, 2925, 2870, 1735, 1455, 1380, 1350, 1283, 1180, 1110, 1050, 1020, 960, 930, 889, 860, 790, 755 cm$^{-1}$.

NMR (100 MHz, CDCl$_3$, δ): 0.76–1.05 (3H, m); 1.11–1.69 (4H, m); 1.24 (3H, d, J=6.6 Hz); 1.26 (3H, t, J=7.03 Hz); 1.87–2.79 (5H, m); 4.14 (2H, q, J=7.03 Hz).

MASS (EI, m/e): 196 (M+).

REFERENCE EXAMPLE 17: Dimethyl 3-methyl-2-oxo-5-decynylphosphonate (17)

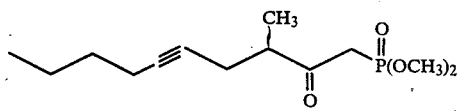

Under argon atmosphere, a solution of n-butyllithium in hexane (1.71N, 29.8 ml, 0.051 mol) was dropwise added to a solution of dimethyl methylphosphonate (6.32 g, 0.051 mol) in anhydrous THF (120 ml) with stirring at −78° C., and the mixture was stirred for 30 minutes. At −78° C., a solution of ethyl 2-methyl-4-nonynoate (4.0 g, 0.02 mol) in anhydrous THF (10 ml) was dropwise added, and the mixture was stirred for 30 minutes. Acetic acid (3.1 ml) and water (20 ml) were then added to the reaction mixture at 0° C. After concentration, water (20 ml) was added to the residue and the resulting mixture was extracted with ethyl acetate (50 ml×2). The ethyl acetate layers were combined, washed with water (20 ml) and with brine (20 ml), and dried over anhydrous sodium sulfate to concentrate. Vacuum distillation of the residue (b.p.=128°–130° C. at 0.16 mmHg) gave dimethyl 3-methyl-2-oxo-5-decynylphosphonate as a colorless, transparent oil (4.75 g, 0.0173 mol, 85% yield). The structure of this product was confirmed by the following data.

IR (Liquid Film): 3470, 2950, 2920, 2860, 1705, 1450, 1395, 1370, 1350, 1320, 1250, 1180, 1070, 870, 830, 805, 730, 680 cm$^{-1}$.

NMR (90 MHz, CDCl$_3$, δ): 0.7–1.1 (3H, m); 1.19 (3H, d, J=7.0 Hz); 1.2–1.7 (4H, m); 1.9–2.3 (2H, m); 2.3–2.5 (2H, m); 2.7–3.1 (1H, m); 3.20 (2H, dd, J=1.8, 22.2 Hz); 3.79 (6H, d, J=11.2 Hz).

MASS (EI, m/e): 274 (M+).

REFERENCE EXAMPLE 18: Ethyl 2,2-dimethyl-4-nonynoate (18)

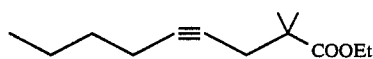

Under argon atmosphere, n-butyllithium (1.71N, 23.43 ml, 40.07 mmol) was added to a solution of diisopropylamine (5.62 ml, 40.07 mmol) in anhydrous THF (50 ml) at −20° C., and the mixture was stirred for 20 minutes. Subsequently, to this reaction mixture, a solution of ethyl 2-methyl-4-nonynoate (7.0122 g, 33.39 mmol) in anhydrous THF (10 ml) and then HMPA (6.97 ml, 40.07 mmol) were added, and the resulting mixture was stirred at room temperature for 30 minutes. Methyl iodide (2.08 ml, 33.39 mmol) was added at −20° C. and the mixture was stirred for 10 minutes. Hydrochloric acid (6N, 9 ml) and water (50 ml) were added to the reaction mixture followed by extraction with ethyl acetate (50 ml×3). The organic layers were combined, washed with saturated aqueous sodium hydrogencarbonate solution (150 ml), with water (150 ml) and with brine (150 ml), and dried over anhydrous magnesium sulfate (50 g) to concentrate, yielding an oily material (8.2783 g). Distillation of this oily material (b.p.=69°−75° C. at 0.18 mmHg) gave a colorless oil, ethyl 2,2-dimethyl-4-nonynoate (6.9706 g, 93% yield). The structure of this product was confirmed by the following data. (NMR and MASS data are shown only for the ethyl ester.)

IR (Liquid Film): 2970, 2930, 2880, 1730, 1468, 1384, 1365, 1318, 1300, 1250, 1200, 1130, 1030, 986, 865, 768, 745 cm$^{-1}$.

NMR (100 MHz, CDCl$_3$, δ): 0.72–1.02 (3H, m); 1.08–1.60 (4H, m); 1.24 (6H, s); 1.24 (3H, t, J=7.03 Hz); 1.97–2.29 (2H, m); 2.38 (2H, t, J=2.20 Hz); 4.13 (2H, q, J=7.03 Hz).

MASS (EI, m/e): 210 (M+).

REFERENCE EXAMPLE 19: Dimethyl 3,3-dimethyl-2-oxo-5-decynylphosphonate (19)

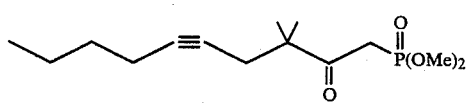

Under argon atmosphere, n-butyllithium (1.71 N, 42.1 ml, 72.0 mmol) was added to a solution of dimethyl methylphosphonate (8.12 ml, 75.0 mmol) in anhydrous THF (250 ml) at −78° C., and the mixture was stirred for 20 minutes. Subsequently, a solution of ethyl 2,2-dimethyl-4-nonynoate (6.7100 g, 30.00 mmol) in anhydrous THF (10 ml) was added and the resulting mixture was stirred for 30 minutes. Acetic acid (5 ml) was then added to the reaction mixture. After concentration, water (50 ml) was added to the residue followed by extraction with ethyl acetate (40 ml×3). The organic layers were combined, washed with brine (100 ml×2), and dried over anhydrous magnesium sulfate (40 g) to concentrate, yielding an oily material (9.7247 g). After distillation of the oily material (b.p.=150°–151° C. at 0.2 mmHg), there was obtained dimethyl 3,3-dimethyl-2-oxo-5-decynylphosphonate, as a colorless oil (6.9088 g, 76% yield). The structure of this product was confirmed by the following data.

IR (Liquid Film): 3450, 2951, 2930, 2860, 1701, 1459, 1382, 1362, 1318, 1232, 1183, 1028, 867, 842, 805, 722 cm$^{-1}$.

NMR (100 MHz, CDCl$_3$, δ): 0.74–1.08 (3H, m); 1.23 (6H, s); 1.13–1.65 (4H, m); 1.92–2.26 (2H, m); 2.36 (2H, t, J=2.20 Hz); 3.24 (2H, d, J=21.33 Hz); 3.80 (6H, d, J=11.22 Hz).

MASS (EI, m/e): 288 (M+).

REFERENCE EXAMPLE 20: 2-Octyne-1-ol (20)

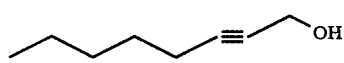

Under argon atmosphere, a small amount of lithium pieces was added to liquid ammonia (250 ml). The reaction mixture became dark blue in color. A catalytic amount of ferric nitrate nonahydrate was added and the mixture was stirred until the dark blue color disappeared. Lithium pieces (2.75 g, 396 mmol) were further added and the reaction mixture was stirred for one hour. Subsequently, propargyl alcohol (8.16 g, 146 mmol) was added and the mixture was stirred for 30 minutes. Then, n-pentyl bromide (20 g, 132 mmol) was added, and the mixture was stirred for 10 minutes and allowed to stand overnight at room temperature. Water-containing ether (50 ml) and water (200 ml) were added and the resulting mixture was extracted with ether (200 ml, 100 ml, 50 ml×3). The organic layers were combined, washed with water (400 ml) and with brine (400 ml), dried over anhydrous sodium sulfate (50 g) to concentrate. The residue was distilled (b.p.=58°–61° C. at 0.3 mmHg), yielding a colorless oil, 2-octyne-1-ol (9.5758 g, 52% yield). The above described structure of this product was confirmed by the following data.

IR (Liquid Film): 3400, 2910, 2850, 2278, 2216, 1447, 1423, 1374, 1323, 1223, 1131, 1102, 1060, 1000, 718 cm$^{-1}$.

NMR (100 MHz, CDCl$_3$, δ): 0.70–1.05 (3H, m); 1.09–1.23 (6H, m); 1.67 (1H, broad s); 1.97–2.39 (2H, m); 4.25 (2H, t, J=2.2 Hz).

MASS (CI, m/e): 144 (M+ +18).

REFERENCE EXAMPLE 21: 1-Bromo-2-octyne (21)

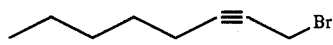

Under argon atmosphere, anhydrous pyridine (0.4 ml, 4.9 mmol) was added to a solution of 2-octyne-1-ol (9.4658 g, 75 mmol) in anhydrous ether (50 ml). To the mixture, there was dropwise added phosphorus tribromide (2.35 ml, 25.0 mmol) at −30° C. to −35° C., and the resulting reaction mixture was stirred for one hour. The mixture was then stirred at room temperature for one hour. Brine (100 ml) was added to the reaction mixture followed by extraction with ether (50 ml×4). The organic layers were combined, washed with saturated aqueous sodium hydrogencarbonate solution (150 ml), with water (150 ml) and with brine (150 ml), and dried over anhydrous sodium sulfate (40 g) to concentrate. The residue was distilled (b.p.=53°–58° C. at 0.39 mmHg), yielding a colorless oil, 1-bromo-2-octyne (9.1493 g, 63% yield). The structure was confirmed by the following data.

IR (Liquid Film): 2949, 2850, 2300, 2220, 1458, 1427, 1379, 1325, 1302, 1283, 1210, 1150, 1105, 1085, 1015, 978, 904, 859, 775, 720, 700 cm$^{-1}$.

NMR (100 MHz, CDCl$_3$, δ): 0.70–1.07 (3H, m); 1.07–1.63 (6H, m); 2.02–2.41 (2H, m); 3.93 (2H, t, J=2.2 Hz).

MASS (CI, m/e): 189 (M$^+$+1).

REFERENCE EXAMPLE 22: Ethyl 2-methyl-4-decynoate (22)

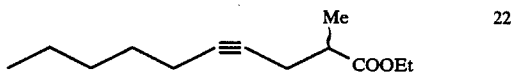

Under argon atmosphere, 60% dispersion of sodium hydride (2.67 g, 66.75 mmol) in mineral oil was suspended in anhydrous THF (90 ml). At room temperature, a solution of diethyl methylmalonate (12.3 ml, 71.52 mmol) in anhydrous THF (15 ml) was added to the suspension and the reaction mixture was stirred for 20 minutes. The reaction mixture was cooled with ice and a solution of 1-bromo-2-octyne (9.011 g, 47.68 mmol) in anhydrous THF (10 ml) was added. The reaction mixture was stirred at room temperature for 30 minutes and hydrochloric acid (3N, 35 ml) was added. After concentration, water (50 ml) was added to the residue and the mixture was extracted with ethyl acetate (40 ml×3). The organic layers were combined, washed with saturated aqueous sodium hydrogencarbonate solution (100 ml), with water (100 ml) and with brine (100 ml), and dried over anhydrous magnesium sulfate (30 g) to concentrate, yielding an oily material (18.3276 g).

To a solution of the oily material in ethanol (170 ml), there was added an aqueous sodium hydroxide solution (1N, 110 ml, 110 mmol), and the mixture was stirred under argon atmosphere at room temperature for 18 hours. Further, an aqueous sodium hydroxide solution (1N, 20 ml) was added and the mixture was stirred at 40°–45° C. for 4 hours and 15 minutes. Hydrochloric acid (3N, 80 ml) was added to the reaction mixture followed by concentration. The residue was extracted with ethyl acetate (70 ml, 50 ml×2). The organic layers were combined, washed with water (150 ml×2) and with brine (150 ml), and dried over anhydrous sodium sulfate (50 g) to concentrate, yielding an oily product (13.8793 g).

This oily product was heated under argon atmosphere at 180° C. for one hour. The reaction mixture was diluted with ether (10 ml). Under ice-cooling, esterification with diazomethane and concentration were effected to yield an oil (9.1324 g). The oil was distilled (b.p.=94°–95° C. at 0.18 mmHg), affording a colorless oil, ether 2-methyl-4-decynoate (8.6349 g, 81% yield). The ratio of the ether ester to its corresponding methyl ester in this colorless oil was 15:1 in GLC using 3% Or-17 column (1 m) with column temperature of 60° C. and inlet temperature of 180° C. The structure of this product was confirmed by the following data. (NMR and MASS data are shown only for the ethyl ester.)

IR (Liquid Film): 2925, 2870, 1735, 1458, 1374, 1350, 1305, 1250, 1228, 1173, 1110, 1050, 1024, 858 cm$^{-1}$.

NMR (100 MHz, CDCl$_3$, δ): 0.71–1.02 (3H, m); 1.02–1.71 (6H, m); 1.23 (3H, d, J=6.38 Hz); 1.26 (3H, t, J=7.03 Hz); 1.86–2.79 (5H, m); 4.14 (2H, q, J=7.03 Hz.

MASS (EI, m/e): 210 (M$^+$).

REFERENCE EXAMPLE 23: Ethyl 2,2-dimethyl-4-decynoate (23)

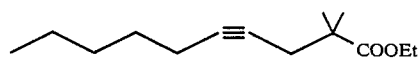

Under argon atmosphere at −20° C., n-butyllithium (1.67 N, 27.3 ml, 45.6 mmol) was added to a solution of diisopropylamine (6.4 ml, 45.6 mmol) in anhydrous THF (70 ml) and the resulting mixture was stirred for 20 minutes. To this reaction mixture, a solution of ethyl 2-methyl-4-decynoate (8.5121 g, 38.0 mmol) in anhydrous THF (10 ml) and HMPA (7.93 ml, 45.6 mmol) were added and the whole mixture was stirred at room temperature for 30 minutes. The mixture was cooled to −20° C. and methyl iodide (2.37 ml, 38.0 mmol) was added followed by stirring for 10 minutes. Hydrochloric acid (6N, 12 ml) and water (50 ml) were added to the reaction mixture. The resulting mixture was extracted with ethyl acetate (50 ml×3). The organic layers were combined, washed with saturated aqueous sodium hydrogencarbonate solution (150 ml), with water (150 ml) and with brine (150 ml), and dried over anhydrous magnesium sulfate (50 g) to concentrate, yielding an oily material (9.2804 g). This material was distilled (b.p.=80°–84° C. at 0.12 mmHg), affording a colorless oil, ethyl 2,2-dimethyl-4-decynoate (7.9839 g, 88% yield). The structure was confirmed by the following data. (NMR and MASS data are shown only for the ethyl ester.)

IR (Liquid Film): 2951, 2925, 2853, 1725, 1462, 1383, 1362, 1319, 1300, 1258, 1199, 1130, 1026, 975, 906, 860, 768, 740 cm$^{-1}$.

NMR (100 MHz, CDCl$_3$, δ): 0.73–1.01 (3H, m); 1.05–1.73 (6H, m); 1.24 (6H, s); 1.24 (3H, t, J=7.03 Hz); 1.93–2.24 (2H, m); 2.38 (2H, t, J=2.2 Hz); 4.14 (2H, q, J=7.03 Hz).

MASS (EI, m/e): 224 (M$^+$).

REFERENCE EXAMPLE 24: Dimethyl 3,3-dimethyl-2-oxo-5-undecynylphosphonate (24)

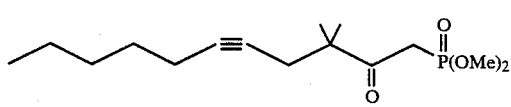

Under argon atmosphere at −78° C., n-butyllithium (1.71 N, 40.8 ml, 69.92 mmol) was added to a solution of dimethyl methylphosphonate (8.24 ml, 76.12 mmol) in anhydrous THF (250 ml) and the mixture was stirred for 20 minutes. To this reaction mixture, there was added a solution of ethyl 2,2-dimethyl-4-decynoate (7.2468 g, 30.4 mmol) in anhydrous THF (10 ml), and the whole mixture was stirred for 30 minutes. Acetic acid (2.2 ml) was added to the mixture followed by concentration. Water (40 ml) was added to the residue and the mixture was extracted with ethyl acetate (40 ml×3). The organic layers were combined, washed with brine (100 ml×2), and dried over anhydrous magnesium sulfate (40 g) to concentrate, yielding an oily material (9.8282 g). This oily material was distilled (b.p.=153° C. at 0.18 mmHg), affording a colorless oil, dimethyl 3,3-dimethyl-2-oxo-5-undecynylphosphonate (7.0663 g, 75% yield). The structure was confirmed by the following data.

IR (Liquid Film): 3450, 2949, 2920, 2850, 1701, 1460, 1380, 1362, 1250, 1180, 1028, 870, 860, 804, 772 cm$^{-1}$.

NMR (100 MHz, CDCl$_3$, δ): 0.70–1.01 (3H, m); 1.01–1.65 (6H, m); 1.23 (6H, s); 1.90–2.26 (2H, m); 2.36 (2H, t, J=2.2 Hz); 3.23 (2H, d, J=21.33 Hz); 3.80 (6H, d, J=11.0 Hz).

MASS (EI, m/e): 302 (M+).

REFERENCE EXAMPLES 25:
d-7-Bromo-2α-hydroxy-1β-hydroxymethyl-3aβH,8bβH-2,3,3a,8b-tetrahydro-5-1H-cyclopenta[b]benzofurancarboxylic acid (25)

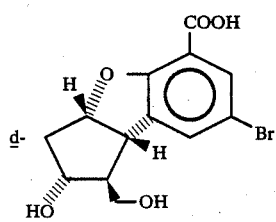

dl-7-Bromo-2α-hydroxy-1β-hydroxymethyl-3aβH,8bβH-2,3,3a,8b-tetrahydro-5-1H-cyclopenta[b]benzofurancarboxylic acid (32.5 g, 99 mmol) and d-cis-N-benzyl-2-hydroxymethylcyclohexylamine (21.7 g, 99 mmol) were dissolved with heating in ethanol (70 ml). The resulting solution was cooled to room temperature and a seed crystal of d-carboxylic acid d-amine salt was inoculated and allowed to stand for three days. The obtained crystal was recrystallized from ethanol (70 ml) and then from 50% aqueous methanol (10 ml), yielding d-7-bromo-2α-hydroxy-1β-hydroxymethyl-3aβH,8bβH-2,3,3a,8b-tetrahydro-5-1H-cyclopenta[b]benzofurancarboxylic acid d-cis-N-benzyl-2-hydroxymethylcyclohexylamine salt (5.30 g, 9.8% yield). This crystal was suspended in distilled water (40 ml) and sulfuric acid (6N, 6 ml) was added to the suspension followed by stirring for 30 minutes. The precipitated d-carboxylic acid was filtered, washed with acetone (10 ml), and dried to yield d-7-bromo-2α-hydroxy-1β-hydroxymethyl-3aβH,8bβH-2,3,3a,8b-tetrahydro-5-1H-cyclopenta[b]benzofurancarboxylic acid (3.00 g, 9.3% yield). The optical purity was 99% or more as determined by converting the carboxylic acid into its methyl ester by means of diazomethane followed by subjecting the methyl ester to liquid chromatography using YMC-peak A-ko3 of 4.6 mm in diameter and 250 mm in length as a column, n-hexane/ethanol/methyl chloride (85/10/5) as an eluent with a flow rate of 1 ml/min., and an oven at room temperature.

Optical Rotation $[\alpha]_D^{20} = +15.2°$ (c=0.92, methanol).

Melting Point: 115.5°–116.5° C.

IR (KBr): 3640, 3500, 3400–2500, 3110, 2980, 2850, 1695, 1650, 1605, 1450, 1390, 1370, 1350, 1335, 1305, 1300, 1260, 1240, 1220, 1170, 1120, 1075, 1020, 995, 950, 915, 885, 870, 840, 795, 790, 690, 655, 620, 560, 525 cm$^{-1}$.

NMR (400 MHz, CDCl$_3$-DMSO-d$_6$, δ): 2.02–2.10 (2H, m); 2.50–2.57 (1H, m); 2.80–3.20 (3H, broad s); 3.60 (1H, t, J=7.8 Hz); 3.66 (1H, dd, J=5.4, 10.5 Hz); 3.78 (1H, dd, J=5.4, 10.4 Hz); 4.01 (1H, q, J=6.5 Hz); 5.31 (1H, ddd, J=5.4, 7.8, 9.3 Hz); 7.52 (1H, m); 7.81 (1H, d, J=2.4 Hz).

MASS (EI, m/e): 328, 330 (M+).

HR (High Resolution) MASS: Calcd. (C$_{13}$H$_{13}$O$_5$Br, M+): 327.9909. Found (M+): 327.9928.

REFERENCE EXAMPLE 26: Methyl d-2α-hydroxy-1β-hydroxymethyl-3aβH,8bβH-2,3,3a,8b-tetrahydro-5-1H-cyclopenta[b]benzofurancarboxylate (26)

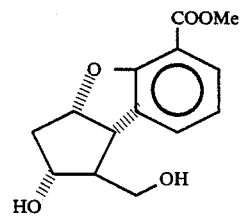

To a solution of d-7-bromo-2α-hydroxy-1β-hydroxymethyl-3aβH,8bβH-2,3,3a,8b-tetrahydro-5-1H-cyclopenta[b]benzofurancarboxylic acid (29.18 g, 88.4 mmol) in methanol (1.5 liter), there was added 10% palladium/active carbon (3 g) and the mixture was stirred under hydrogen atmosphere at room temperature for 2 hours. Then, the reaction mixture was refluxed under argon atmosphere for 3 hours followed by filtration. The filtrate was concentrated and water (200 ml) was added to the residue. The mixture was extracted with chloroform (300 ml×3). The organic layers were combined, washed with brine (100 ml), and dried over anhydrous magnesium sulfate to concentrate, yielding a crude crystal (22.3 g). The crude crystal was recrystallized from ether acetate affording a prism crystal, methyl d-2α-hydroxy-1β-hydroxymethyl-3aβH,8bβH-2,3,3a,8b-tetrahydro-1H-cyclopenta[b]benzofurancarboxylate (20.87 g, 79.1 mmol, 89.4% yield). The above described structure of this product was confirmed by the following data.

Optical Rotation $[\alpha]_D^{20} = +109.6°$ C. (c=1.028, methanol).

Melting Point: 154°–155° C.

IR (KBr): 3280, 3170, 3030, 2990, 2950, 2900, 1720, 1605, 1445, 1430, 1370, 1355, 1315, 1275, 1250, 1220, 1190, 1170, 1140, 1105, 1075, 1065, 1055, 1040, 1015, 995, 965, 905, 880, 855, 840, 765, 710, 625 cm$^{-1}$.

NMR (400 MHz, CDCl$_3$-DMSO-d$_6$, δ): 2.01–2.08 (2H, m); 2.67–2.63 (1H, m); 3.54 (1H, t, J=8.3 Hz); 3.78 (2H, t, J=5.4 Hz); 3.88 (3H, s); 4.05 (1H, d, J=4.9 Hz); 4.01–4.08 (1H, m); 4.14 (1H, t, J=5.3 Hz); 5.26 (1H, ddd, J=5.3, 8.3, 9.3 Hz); 6.86 (1H, t, J=7.3 Hz); 7.41 (1H, m); 7.70 (1H, dd, J=1.0, 7.3 Hz).

MASS (EI, m/e): 264 (M+).

HR MASS Calcd. (C$_{14}$H$_{16}$O$_5$, M+): 264.0962. Found (M+): 264.0980.

REFERENCE EXAMPLE 27: Methyl d-2α-hydroxy-1β-hydroxymethyl-3aβH,8bβH-2,3,3a,8b-tetrahydro-5-1H-cyclopenta[b]benzofuran-propionate (27)

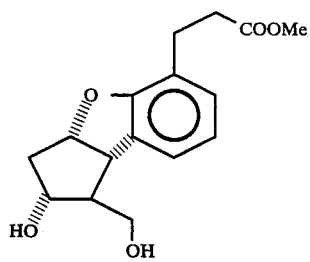

27

To a solution of methyl d-2α-hydroxy-1β-hydroxymethyl-3aβH,8bβH-2,3,3a,8b-tetrahydro-5-1H-cyclopenta[b]benzofurancarboxylate (47.20 g, 187.30 mmol) in anhydrous THF (250 ml), there were added dihydropyran (47.60 ml, 515.80 mmol) and a solution of p-toluenesulfonic acid in THF (150 ml), which was prepared by dissolving p-touenesulfonic acid (3.636 g) in THF (180 ml) and drying over Molecular Sieve 4A 1/16, under ice-cooling. The reaction mixture was stirred at room temperature for 3 hours. Sodium hydrogencarbonate (20 g) was added to the reaction mixture. After the mixture was stirred at room temperature for 10 minutes, it was subjected to suction filtration by means of Celite. The filtrate was concentrated. Water (200 ml) was added to the residue and the mixture was extracted with ethyl acetate (200 ml×2). The organic layers were combined, washed with brine (300 ml), and dried over anhydrous sodium sulfate (80 g) to concentrate, yielding an oily material (114.58 g).

Separately, under argon atmosphere, lithium aluminum hydride (5.331 g, 140.47 mmol) was added to anhydrous THF (250 ml) and the mixture was stirred. To this mixture there was dropwise added a solution of the above obtained oily material (114.58 g), in anhydrous THF (150 ml) under ice-cooling. The whole mixture was further stirred for 15 minutes while ice-cooling. To this reaction mixture, there were added ethyl acetate (100 ml) and saturated aqueous sodium sulfate solution (15 ml) under ice-cooling. The mixture was subjected to suction filtration with Celite and the filtrate was concentrated to yield an oily product (91.2 g).

This oily product (91.2 g) was dissolved in dichloromethane (350 ml) and active manganese dioxide (350 g) was added to the solution under ice-cooling. The mixture was stirred overnight at room temperature. The reaction mixture was filtered by suction with Celite and the filtrate was concentrated to yield an oil (81.21 g).

This oil (81.21 g) was dissolved in benzene (1,000 ml) and carbomethoxymethylenetriphenylphospholan (93.8 g, 280.95 mmol) was added. The mixture was stirred at room temperature for 2 days. The reaction mixture was concentrated and the residue was purified by silica gel column chromatography using ethyl acetate/cyclohexane (1/4) to yield an oily material (82.58 g).

To a solution of this oily material (82.58 g) in methanol (400 ml) there was added palladium/carbon (10 g) and the mixture was stirred overnight under hydrogen atmosphere at room temperature. The reaction mixture was filtered by suction with Celite and the filtrate was concentrated to yield an oil (79.14 g).

To a solution of this oil (79.14 g) in methanol (400 ml), there was added p-toluenesulfonic acid (2.4 g) under ice-cooling. The whole mixture was then stirred overnight at room temperature. Sodium hydrogencarbonate (20 g) was added to the reaction mixture followed by stirring at room temperature for 20 minutes. The mixture was subjected to suction filtration using Celite and the filtrate was concentrated. Water (100 ml) was added to the residue and the mixture was extracted with ethyl acetate (100 ml×2). The organic layers were combined, washed with brine (100 ml), and dried over anhydrous sodium sulfate (30 g) to concentrate. The residue was recrystallized from ethyl acetate/cyclohexane (6/1) to afford a colorless needle-like crystal, methyl d-2α-hydroxy-1β-hydroxymethyl-3aβH,8bβH-2,3,3a,8b-tetrahydro-5-1H-cyclopenta[b]benzofuran-propionate (32.51 g, 111.34 mmol, 59.4% yield). The structure of this product was confirmed by the following data.

Melting Point: 110°-110.5° C.

$[\alpha]_D^{20}$: =30.52 (c=0.868, MeOH).

IR (KBr): 3400, 2950, 2905, 2855, 1700, 1591, 1456, 1442, 1359, 1321, 1293, 1279, 1243, 1213, 1181, 1155, 1102, 1059, 1010, 968, 950, 919, 899, 843, 833, 802, 766, 742, 620, 580, 542, 521, 500, 433 cm$^{-1}$.

NMR (400 MHz, CDCl$_3$, δ): 1.8-1.9 (1H, broad s); 2.01-2.08 (1H, m); 2.12-2.20 (1H, m); 2.2-2.3 (1H, broad s); 2.55-2.72 (3H, m); 2.84-2.97 (2H, m); 3.39-3.45 (1H, m); 3.66 (3H, s); 3.76-3.83 (1H, m); 3.94-4.00 (1H, m); 4.10-4.18 (1H, m); 5.10-5.19 (1H, m); 6.79 (1H, t, J=7.32 Hz); 6.79 (1H, d, J=7.32 Hz); 7.04 (1H, d, J=7.32 Hz).

MASS (EI, m/e): 292 (M+).

REFERENCE EXAMPLE 28: 16-Methyl-15-oxo-2,5,6,7-tetranor-18,18,19,19-tetradehydro-4,8-inter-m-phenylene PGI$_2$ methyl ester, 11-acetate (28)

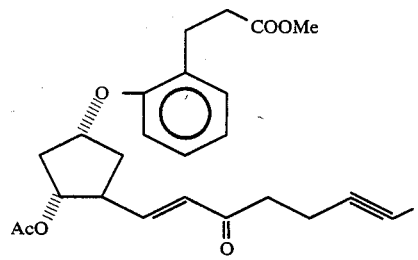

28

Under argon atmosphere, anhydrous pyridine (0.24 ml, 3.00 mmol), anhydrous DMSO (6 ml), trifluoroacetic acid (0.18 ml, 2.28 mmol) and DCC (1.25 g, 6.00 mmol) were added to a solution of methyl 2α-acetoxy-1β-hydroxymethyl-3aβH, 8bβH-2,3,3a,8b-tetrahydro-5-1H-cyclopenta[b]benzofuranpropionate (1.0037 g, 3.00 mmol) and the mixture was stirred at room temperature for 2 hours. After calcium carbonate (1.48 g, 14.82 mmol) was added, the reaction mixture was stirred for 20 minutes.

Separately, 60% dispersion of sodium hydride (216 mg, 5.4 mmol) in mineral oil was suspended in anhydrous THF (30 ml) and a solution of dimethyl 3-methyl-2-oxo-5-heptynylphosphonate (1.39 g, 6.00 mmol) in anhydrous THF (5 ml) was added to the suspension, followed by stirring the reaction mixture under argon atmosphere at room temperature for 30 minutes. To this reaction mixture, there was added the supernatant of another reaction mixture prepared separately above by a syringe under ice-cooling. The residue of said another reaction mixture was washed with anhydrous THF (10 ml, 5 ml×2) and the supernatant of the washings was also added to the above reaction mixture.

The reaction mixture was stirred at room temperature for 30 minutes and saturated aqueous ammonium chloride solution (60 ml) was added. The mixture was extracted with ethyl acetate (40 ml×3). The organic layers were combined, washed with water (100 ml) and with brine (100 ml), and dried over anhydrous magnesium sulfate (30 g) to concentrate. The residue was purified by silica gel column chromatography using ethyl acetate/cyclohexane (¼) as an eluent, yielding a colorless oily product, 16-methyl-15-oxo-2,5,6,7-tetranor-18,18,19,19-tetradehydro-4,8-inter-m-phenylene PGI$_2$ methyl ester, 11-acetate (1.1856 g, 2.71 mmmol, 90% yield). The above described structure of this product was confirmed by the following data.

IR (Liquid Film): 2925, 1735, 1688, 1663, 1622, 1598, 1444, 1370, 1319, 1295, 1239, 1195, 1170, 1163, 981, 949, 850, 746 cm$^{-1}$.

NMR (100 MHz, CDCl$_3$, δ): 1.21 (3H, d, J=7.04 Hz); 1.61–1.86 (3H, m); 1.77 (3H, s); 1.96–2.11 (10H, broad m); 3.67 (3H, s); 3.56–3.83 (1H, m); 5.00 (1H, q, J=5.73 Hz); 5.11–5.40 (1H, m); 6.26 (1H, d, J=14.73 Hz); 6.64–7.11 (4H, m).

MASS (EI, m/e): 438 (M+).

REFERENCE EXAMPLE 29:
16-Methyl-15-oxo-20a-homo-2,5,6,7-tetranor-18,18,19,19-tetradehydro-4,8-inter-m-phenylene PGI$_2$ methyl ester, 11-acetate (29)

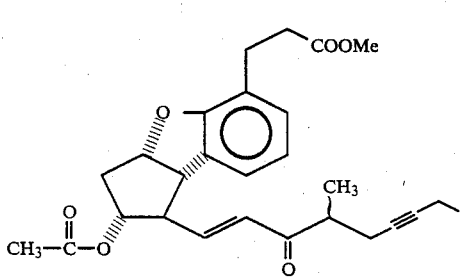

Under argon atmosphere, anhydrous pyridine (0.073 ml, 0.906 mmol), anhydrous trifluoroacetic acid (0.068 ml, 0.88 mmol), anhydrous DMSO (2.11 ml, 29.7 mmol) and DCC (0.92 g, 4.45 mmol) were added to a solution of methyl 2α-acetoxy-1β-hydoxymethyl-3aβH,8bβH-2,3,3a,8b-tetrahydro-5-1H-cyclopenta[b]benzofuran-propionate (1.0 g, 2.99 mmol) in anhydrous THF (6 ml) while stirring and ice-cooling. The reaction mixture was stirred at room temperature for 3 hours.

Separately, a solution of dimethyl 3-methyl-2-oxo-5-octynylphosphonate (1.11 g, 4.5 mmol) in anhydrous THF (5 ml) was dropwise added to a suspension of 60% mineral oil dispersion of sodium hydride (0.18 g, 4.5 mmol) in anhydrous THF (8 ml) under argon atmosphere with ice-cooling and the mixture was stirred for 30 minutes. To this reaction mixture, there was added another reaction mixture prepared separately above while stirring under ice-cooling.

The reaction mixture was then stirred at room temperature for 30 minutes. Acetic acid was added to this mixture to neutralize, followed by filtration. After concentration of the filtrate, water (20 ml) was added to the residue and the mixture was extracted with ethyl acetate (60 ml×2). Ethyl acetate layers were combined, washed with water (20 ml) and with brine (20 ml), and dried over anhydrous sodium sulfate to concentrate. The residue was purified by silica gel column chromatography using ethyl acetate/cyclohexane (1/5) as an eluent to remove bi-products and remaining Wordsworth reagent. The resulting crude product was further purified by Merck Lobar silica gel column using ethyl acetate/cyclohexane (1/4) to afford pure 16-methyl-15-oxo-20a-homo-2,5,6,7-tetranor-18,18,19,19-tetradehydro-4,8-inter-m-phenylene PGI$_2$ methyl ester, 11-acetate (1.14 g, 2.52 mmol, 84.2% yield). The structure of this product was confirmed by the following data.

IR (Liquid Film): 2920, 2850, 1730, 1685, 1660, 1620, 1590, 1540, 1440, 1360, 1230, 1185, 1060, 1020, 970, 885, 840, 740 cm$^{-1}$.

NMR (400 MHz, CDCl$_3$, δ): 1.11 (3H, t, J=7.3 Hz); 1.22 (3H, d, J=7.3 Hz); 1.77, 1.78 (3H, s); 2.1–2.2 (3H, m); 2.25–2.35 (1H, m); 2.4–2.5 (1H, m); 2.6–2.7 (3H, m); 2.85–3.0 (4H, m); 3.68 (3H, s); 3.65–3.75 (1H, m); 4.95–5.05 (1H, m); 5.2–5.3 (1H, m); 6.28–6.30 (1H, dd, J=1.0, 15.6 Hz); 6.77 (1H, t, J=7.5 Hz); 6.83 (1H, dd, J=8.3, 15.6 Hz); 6.96–7.05 (2H, m).

MASS (EI, m/e): 452 (M+).

REFERENCE EXAMPLE 30:
16-Methyl-15-oxo-20a,20b-dihomo-2,5,6,7-tetranor-18,18,19,19-tetradehydro-4,8-inter-m-phenylene PGI$_2$ methyl ester, 11-acetate (30)

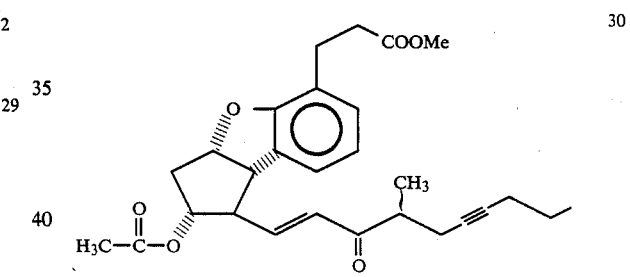

Under argon atomsphere, anhydrous pyridine (0.073 ml, 0.906 mmol), anhydrous trifluoroacetic acid (0.068 ml, 0.88 mmol), anhydrous DMSO (2.11 ml, 29.7 mmol) and D.C.C. (0.92 g, 4.45 mmol) were added to a solution of methyl 2α-acetoxy-1β-hydroxymethyl-3aβH,8bβH-2,3,3a,8b-tetrahydro-5-1H-cyclopenta[b]benzofuran-propionate (1.0 g, 2.99 mmol) in anhydrous THF (6 ml) while stirring and ice-cooling. The reaction mixture was stirred at room temperature for 3 hours.

Separately, while ice-cooling under argon atmosphere, a solution of dimethyl 3-methyl-2-oxo-5-nonanylphosphonate (1.17 g, 4.49 mmol) in anhydrous THF (5 ml) was dropwise added to a suspension of 60% mineral oil dispersion of sodium hydride (0.18 g, 4.5 mmol) in anhydrous THF (8 ml) and the mixture was stirred for 30 minutes. To this reaction mixture, there was added another reaction mixture prepared separately above while stirring and ice-cooling. The reaction mixture was stirred for 30 minutes.

The reaction mixture was neutralized with acetic acid followed by filtration. After concentration of the filtrate, water (20 ml) was added to the residue and the mixture was extracted with ethyl acetate (50 ml×2). The ethyl acetate layers were combined, washed with water (20 ml) and with brine (20 ml), and dried over anhydrous magnesium sulfate to concentrate. The residue was subjected to silica gel column chromatography using ethyl acetate/cyclohexane (1/5) as an eluent to remove bi-products and remaining Wordsworth reagent. The resulting crude product was further purified by Merck Lobar column using silica gel and ethyl acetate/cyclohexane (¼) to afford an oily product, 16-methyl-15-oxo-20a,20b-dihomo-2,5,6,7-tetranor-18,18,19,19-tetradehydro-4,8-inter-m-phenylene PGI$_2$ methyl ester, 11-acetate (1.04 g, 2.23 mmol, 74.5% yield). The structure was confirmed by the following data.

IR (Liquid Film): 2960, 2930, 1730, 1960, 1665, 1620, 1595, 1450, 1360, 1240, 1190, 1060, 980, 840, 545 cm$^{-1}$.

NMR (400 MHz, CDCl$_3$, δ): 0.956, 0.959 (3H, t, J=7.3 Hz); 1.22 (3H, d, J=7.3 Hz); 1.49 (2H, m); 1.77, 1.78 (3H, s); 2.0–3.0 (12H, m); 3.67 (3H, s); 3.6–3.8 (1H, m); 4.9–5.1 (1H, m); 5.2–5.3 (1H, m); 6.29, 6.30 (1H, dd, J=0.98, 15.6 Hz); 6.97 (1H, t, J=7.7 Hz); 6.99 (1H, d, J=7.7 Hz).

MASS (EI, m/e): 466 (M+).

REFERENCE EXAMPLE 31:
16-Methyl-15-oxo-20a,20b,20c-trihomo-2,5,6,7-tetranor-18,18,19,19-tetrahydro-4,8-inter-m-phenylene PGI$_2$ methyl ester, 11-acetate (31)

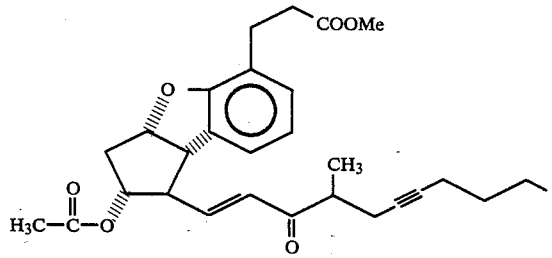

Under argon atmosphere, anhydrous pyridine (0.073 ml, 0.906 mmol), anhydrous trifluoroacetic acid (0.068 ml, 0.88 mmol), anhydrous DMSO (2.11 ml, 29.7 mmol) and D.C.C. (0.92 g, 4.45 mmol) were added to a solution of methyl 2α-acetoxy-1β-hydroxymethyl-3aβH,8bβH-2,3,3a8b-tetrahydro-5-1H-cyclopenta[b]benzofuranpropionate (1.0 g, 2.99 mmol) in anhydrous THF (6 ml) while stirring and ice-cooling. The reaction mixture was stirred at room temperature for 3 hours.

Separately, while ice-cooling under argon atmosphere, a solution of dimethyl 3-methyl-2-oxo-5-decynylphosphonate (1.23 g, 4.5 mmol) in anhydrous THF (5 ml) was dropwise added to a suspension of 60% mineral oil dispersion of sodium hydride (0.18 g, 4.5 mmol) in anhydrous THF (8 ml) and the mixture was stirred for 30 minutes. To this reaction mixture stirred under ice-cooling, there was added the above reaction mixture prepared separately. The whole mixture was stirred at room temperature for 30 minutes.

Acetic acid was added to the reaction mixture to neutralize followed by filtration. After concentration of the filtrate, water (20 ml) was added to the residue and the mixture was extracted with ethyl acetate (60 ml×2). Ethyl acetate layers were combined, washed with water (20 ml) and with brine (20 ml), and dried over anhydrous magnesium sulfate to concentrate. The residue was roughly purified by column chromatography using silica gel (50 gel) and ethyl acetate/cyclohexane (1/8) as an eluent to separate biproducts and remaining Wordsworth agent. The product was further purified by Merck Lobar silica gel column using ethyl acetate/cyclohexane (1/4) as an eluent to afford an oily product, 16-methyl-15-oxo-20a,20b,20c-trihomo-2,5,6,7-tetranor-18,18,19,19-tetradehydro-4,8-inter-m-phenylene PGI$_2$ methyl ester, 11-acetate (1.13 g, 2.35 mmol, 78.6% yield). The structure of this product was confirmed by the following data.

IR (Liquid Film): 2950, 2930, 2875, 1735, 1690, 1670, 1625, 1595, 1450, 1370, 1320, 1295, 1240, 1190, 1170, 1065, 1010, 980, 950, 890, 845, 750 cm$^{-1}$.

NMR (400 MHz, CDCl$_3$, δ): 0.93 (3H, t, J=6.8 Hz); 1.22 (3H, d, J=6.8 Hz); 1.3–1.5 (4H, m); 1.77 (3H, s); 2.1–2.2 (3H, m); 2.25–2.35 (1H, m); 2.4–2.5 (1H, m); 2.6–2.7 (3H, m); 2.85–3.0 (4H, m); 3.68 (3H, s); 3.6–3.7 (1H, m); 5.2–5.3 (1H, m); 6.28, 6.30 (1H, dd, J=1.0, 15.6 Hz); 6.77 (1H, t, J=7.3 Hz); 6.818, 6.822 (1H, dd, J=8.3, 15.6 Hz); 6.9–7.0 (2H, m).

MASS (EI, m/e): 480 (M+).

REFERENCE EXAMPLE 32:
16,16-Dimethyl-15-oxo-2,5,6,7-tetranor-18,18,19,19-tetradehydro-4,8-inter-m-phenylene PGI$_2$ methyl ester, 11-acetate (32)

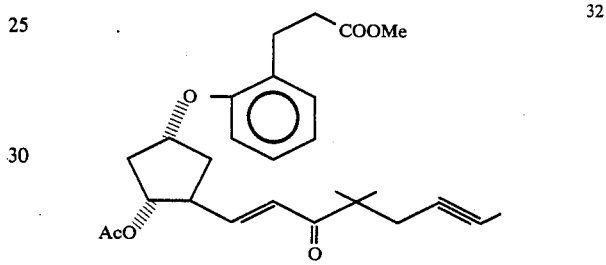

Under argon atmosphere, anhydrous pyridine (0.22 ml, 2.7 mmol), anhydrous DMSO (5 ml), trifluoroacetic acid (0.16 ml, 2.1 mmol) and D.C.C. (1.123 g, 5.4 mmol) were added to a solution of methyl 2α-acetoxy-1β-hydroxymethyl-3aβH,8bβH-2,3,3a,8b-tetrahydro-5-1H-cyclopenta[b]benzofuranpropionate (900.1 mg, 2.7 mmol) in anhydrous THF (15 ml) and the resulting mixture was stirred at room temperature for one hour. After calcium carbonate (1.33 g, 13.3 mmol) was added, the reaction mixture was stirred for 20 minutes and allowed to stand.

Separately, a solution of dimethyl 3,3-dimethyl-2-oxo-5-heptynylphosphonate (797.04 mg, 3.24 mmol) in anhydrous THF (5 ml) was added to a suspension of 60% mineral oil dispersion of sodium hydride (129.6 mg, 3.24 mmol) in anhydrous THF (20 ml) and the mixture was stirred under argon atmosphere at room temperature for 30 minutes. To this reaction mixture, the supernatant of another reaction mixture prepared separately above was added by a syringe under ice-cooling. The residue of said another reaction mixture was washed with anhydrous THF (10 ml, 5 ml×2) and the resulting supernatant was also added to the above said reaction mixture.

The whole reaction mixture was stirred at room temperature for 20 minutes and saturated aqueous ammonium chloride solution (50 ml) was added to the mixture, followed by extraction with ethyl acetate (40 ml×3). The organic layers were combined, washed with water (100 ml) and with brine (100 ml), and dried over anhydrous sodium sulfate (30 g) to concentrate. The residue was purified by silica gel column chromatography using ethyl acetate/cyclohexane (1/3) afford a colorless oil, 16,16-dimethyl-15-oxo-2,5,6,7-tetranor-18,18,19,19-tetradehydro-4,8-inter-m-phenylene PGI₂ methyl ester, 11-acetate (810 mg, 1.79 mmol, 66% yield). The above described structure of this product was confirmed by the following data.

IR (Liquid Film): 2915, 2855, 1730, 1685, 1624, 1598, 1510, 1442, 1361, 1321, 1290, 1230 1190, 1050, 1000, 975, 940, 863, 845, 740 cm⁻¹.

NMR (100 MHz, CDCl₃, δ): 1.22 (6H, s); 1.77 (3H, s); 1.72–1.80 (3H, m); 1.90–3.09 (9H, m); 3.67 (3H, s); 3.67 (1H, m); 4.99 (1H, q, J=5.55 Hz); 5.05–5.43 (1H, m); 6.60 (1H, d, J=15.17 Hz); 6.68–7.06 (4H, m).

MASS (EI, m/e): 452 (M+).

REFERENCE EXAMPLE 33:
16,16-Dimethyl-15-oxo-20a-homo-2,5,6,7-tetranor-18,18,19,19-tetradehydro-4,8-inter-m-phenylene PGI₂ methyl ester, 11-acetate (33)

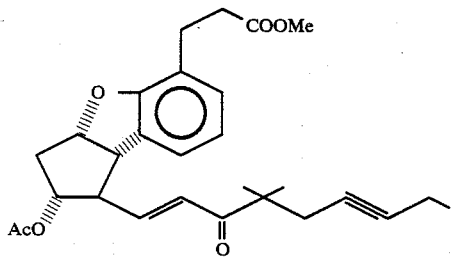

Under argon atmosphere, anhydrous pyridine (0.24 ml, 3.00 mmol), anhydrous DMSO (5 ml), trifluoroacetic aicd (0.18 ml, 2.28 mmol) and D.C.C. (1.25 g, 6.00 mmol) were added to a solution of methyl 2α-acetoxy-1β-hydroxymethyl-3aβH,8bβH-2,3,3a,8b-tetrahydro-5-1H-cyclopenta[b]benzofuranpropionate (1.0056 g, 3.00 mmol) in anhydrous THF (10 ml) and the mixture was stirred at room temperature for 2 hours. After calcium carbonate (1.48 g, 14.82 mmol) was added, the mixture was stirred for 20 minutes and allowed to stand.

Separately, 60% dispersion of sodium hydride (168 mg, 4.2 mmol) in mineral oil was suspended in anhydrous THF (20 ml) and a solution of dimethyl 3,3-dimethyl-2-oxo-5-octynylphosphonate (1.17 g, 4.5 mmol) in anhydrous THF (5 ml) was added. The mixture was stirred under argon atmosphere at room temperature for 30 minutes. To this reaction mixture, there was added the supernatant of the another reaction mixture prepared separately above by a syringe under ice-cooling. The residue of said another reaction mixture was washed with anhydrous THF (10 ml×2, 5 ml) and the resulting supernatant thereof was also added.

The whole reaction mixture was stirred at room temperature for 30 minutes. Saturated aqueous ammonium chloride solution (50 ml) was added and the resulting mixture was extracted with ethyl acetate (30 ml×3). The organic layers were combined, washed with water (100 ml) and with brine (100 ml), and dried over anhydrous sodium sulfate (25 g) to concentrate. The residue was purified by silica gel column chromatography using ethyl acetate/cyclohexane (1/4) to afford a colorless oily product, 16,16-dimethyl-15-oxo-20a-homo-2,5,6,7-tetranor-18,18,19,19-tetradehydro-4,8-inter-m-phenylene PGI₂ methyl ester, 11-acetate (1.147 g, 2.46 mmol, 82% yield). The structure was confirmed by the following data.

IR (Liquid Film): 2957, 2920, 1730, 1685, 1623, 1598, 1446, 1364, 1322, 1296, 1230, 1190, 1063, 1005, 980, 946, 865, 846, 779, 745 cm⁻¹.

NMR (400 MHz, CDCl₃, δ): 1.10 (3H, t, J=7.32 Hz); 1.23 (6H, s); 1.78 (3H, s); 2.11–2.19 (3H, m); 2.37–2.43 (2H, m); 2.59–2.73 (3H, m); 2.86–3.01 (3H, m); 3.67 (3H, s); 3.63–3.74 (1H, m); 4.99 (1H, q, J=5.86 Hz); 5.23–5.29 (1H, m); 6.61 (1H, d, J=15.14 Hz); 6.77 (1H, t, J=7.33 Hz); 6.85 (1H, dd, J=15.14, 8.55 Hz); 6.99 (2H, d, J=7.33 Hz).

MASS (EI, m/e): 466 (M+).

REFERENCE EXAMPLE 34:
16,16-Dimethyl-15-oxo-20a,20b,20c-trihomo-2,5,6,7-tetranor-18,18,19,19-tetradehydro-4,8-inter-m-phenylene PGI₂ methyl ester, 11-acetate (34)

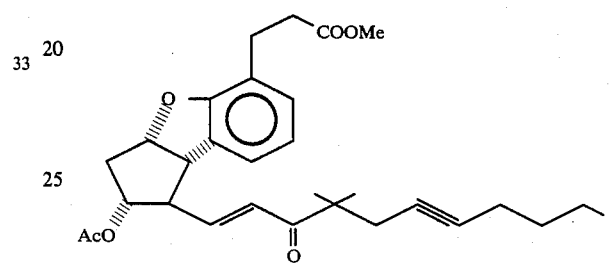

Under argon atmosphere, anhydrous pyridine (0.27 ml, 3.35 mmol), anhydrous DMSO (5 ml), trifluoroacetic acid (0.08 ml, 1.01 mmol) and DCC (1.40 g, 6.71 mmol) were added to a solution of methyl 2α-acetoxy-1β-hydroxymethyl-3aβH,8bβH-2,3,3a,8b-tetrahydro-5-1H-cyclopenta[b]benzofuranpropionate (1.1201 g, 3.35 mmol) in anhydrous THF (15 ml) and the resulting mixture was stirred at room temperature for 3 hours. After calcium carbonate (657 mg, 6.06 mmol) was added, the reaction mixture was stirred for 20 minutes and allowed to stand.

Separately, 60% dispersion of sodium hydride (201.2 mg, 5.03 mmol) in mineral oil was suspended in anhydrous THF (20 ml) and a solution of dimethyl 3,3-dimethyl-2-oxo-5-decynylphosphonate (1.52 g, 5.03 mmol) in anhydrous THF (5 ml) was added. The resulting mixture was stirred under argon atmosphere at room temperature for 30 minutes. To this reaction mixture, there was added the supernatant of another reaction mixture prepared above separately by a syringe under ice-cooling. The residue of the another reaction mixture was washed with anhydrous THF (10 ml, 5 ml33 2) and the resulting supernatant was also added to the reaction mixture described above.

The whole reaction mixture was stirred at room temperature for 30 minutes. After saturated aqueous ammonium chloride solution (60 ml) was added, the mixture was extracted with ethyl acetate (50 ml×3). The organic layers were combined, washed with water (150 ml) and with brine (150 ml), and dried over anhydrous sodium sulfate (30 g) to concentrate. The residue was purified by silica gel column chromatography using ethyl acetate/cyclohexane (1/5) to afford a colorless oily product, 16,16-dimethyl-15-oxo-20a,20b,20c-trihomo-2,5,6,7-tetranor-18,18,19,19-tetradehydro-4,8-inter-m-phenylene PGI₂ methyl ester, 11-acetate (1.4109 g, 2.86 mmol, 85% yield). The structure of this product was confirmed by the following data.

IR (Liquid Film): 2950, 2924, 2850, 1740, 1692, 1620, 1595, 1455, 1365, 1325, 1300, 1240, 1195, 1172, 1151, 1060, 1004, 960, 947, 868, 845, 742, cm$^{+1}$.

NMR (400 MHz, CDCl$_3$, δ): 0.89 (3H, t, J=7.15 Hz); 1.23 (6H, s); 1.32–1.49 (4H, m); 1.78 (3H, s); 2.09–2.18 (3H, m); 2.33–2.44 (2H, m); 2.57–2.71 (3H, m); 2.85–2.99 (3H, m); 3.67 (3H, s); 3.63–3.71 (1H, m); 4.99 (1H, q, J=5.86 Hz); 5.23–5.29 (1H, m); 6.61 (1H, d, J=15.39 Hz); 6.77 (1H, t, J=7.33 Hz); 6.85 (1H, dd, J=15.39, 8.43 Hz); 6.99 (2H, d, J=7.33 Hz).

MASS (EI, m/e): 494 (M+).

REFERENCE EXAMPLE 35:
16,16-Dimethyl-15-oxo-20a,20b,20c,20d-tetrahomo-2,5,6,7-tetranor-18,18,19,19-tetradehydro-4,8-inter-m-phenylene PGI$_2$ methyl ester, 11-acetate (35)

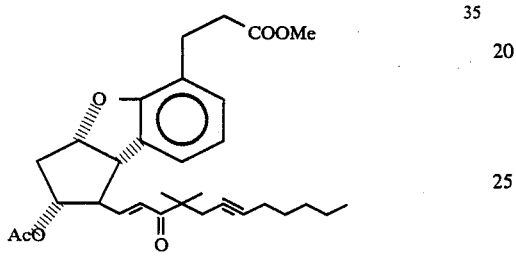

Under argon atmosphere, anhydrous pyridine (0.27 ml, 3.32 mmol), anhydrous DMSO (5 ml), trifluoroacetic acid (0.13 ml, 1.66 mmol) and D.C.C. (1.384 g, 6.44 mmol) were added to a solution of methyl 2α-acetoxy-1β-hydroxymethyl-3aβH,8bβH-2,3,3a,8b-tetrahydro-5-1H-cyclopenta[b]benzofuranpropionate (1.1084 g, 3.32 mmol) in anhydrous THF (20 ml), and the resulting mixture was stirred at room temperature for one hour. After calcium carbonate (1.088 g, 10.8 mmol) was added, the reaction mixture was stirred for 20 minutes and allowed to stand.

Separately, 60% dispersion of sodium hydride (239.0 mg, 5.98 mmol) in mineral oil was suspended in anhydrous THF (30 ml) and a solution of dimethyl 3,3-dimethyl-2-oxo-5-undecynylphosphonate (2.0224 g, 6.64 mmol) in anhydrous THF (5 ml) was added to the suspension. The mixture was stirred under argon atmosphere at room temperature for 30 minutes. To this reaction mixture, the supernatant of another reaction mixture prepared above separately was added by a syringe under ice-cooling. The residue of the another reaction mixture was washed with anhydrous THF (10 ml, 5 ml ×2) and the resuling supernatant was also added to the above said reaction mixture.

The whole reaction mixture was stirred at room temperature for 30 minutes. After saturated aqueous ammonium chloride solution (60 ml) was added, the mixture was extracted with ethyl acetate (50 ml×3). The organic layers were combined, washed with water (150 ml) and with brine (150 ml), and dried over anhydrous magnesium sulfate (40 g) to concentrate. The residue was purified by silica gel column chromatography using ethyl acetate/cyclohexane (1/5) to afford a colorless oily product, 16,16-dimethyl-15-oxo-20a,20b,20c,20d-tetrahomo-2,5,6,7-tetranor-18,18,19,19-tetradehydro-4,8-inter-m-phenylene PGI$_2$ methyl ester, 11-acetate (1.5275 g, 3.01 mmol, 91% yield). The structure of this product was confirmed by the following data.

IR (Liquid Film): 2950, 2925, 2854, 1735, 1685, 1620, 1595, 1446, 1362, 1325, 1300, 1240, 1198, 1175, 1062, 1003, 960, 945, 891, 864, 845, 744 cm$^{-1}$.

NMR (400 MHz, CDCl$_3$, δ): 0.87–0.90 (3H, m); 1.22 (6H, s); 1.25–1.42 (4H, m); 1.42–1.53 (2H, m); 1.77 (3H, s); 2.08–2.20 (3H, m); 2.38–2.42 (2H, broad s); 2.59–2.72 (3H, m); 2.86–3.01 (3H, m); 3.67 (3H, s); 3.66–3.74 (1H, m); 4.97–5.03 (1H, m); 5.22–5.31 (1H, m); 6.61 (1H, d, J=15.63 Hz); 6.77 (1H, t, J=7.33 Hz); 6.84 (1H, dd, J=15.63, 8.55 Hz); 6.99 (2H, d, J=7.33 Hz).

MASS (EI, m/e): 508 (M+).

EXAMPLE 1:
16-Methyl-2,5,6,7-tetranor-18,18,19,19-tetradehydro-4,8-inter-m-phenylene PGI$_2$ methyl ester (36) and its 15-epimer (37)

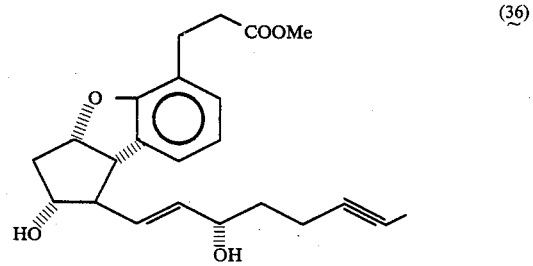

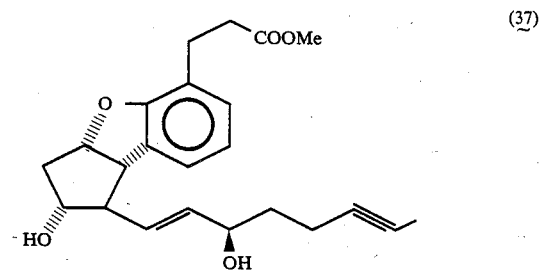

While stirring and ice-cooling, sodium borohydride (133 mg, 3.16 mmol) was added to a solution of 16-methyl-15-oxo-2,5,6,7-tetranor-18,18,19,19-tetradehydro-4,8-inter-m-phenylene PGI$_2$ methyl ester, 11-acetate (1.1552 g, 2.64 mmol) and cerium trichloride heptahydrate (1.48 g, 3.96 mmol) in methanol (20 ml), and the mixture was stirred for 10 minutes. A saturated aqueous sodium hydrogencarbonate solution (15 ml) was added to the mixture followed by extraction with ethyl acetate (15 ml×3). The organic layers were combined, washed with water (50 ml) and with brine (50 ml), and dried over anhydrous magnesium sulfate (20 g) to concentrate, yielding an oily material (1.1612 g).

This oily material was azeotropically distilled with benzene (10 ml×2). To a solution of the resulting residue in absolute methanol (11 ml) there was added sodium methoxide (4.89 N, 0.13 ml, 0.66 mmol), and the mixture was stirred under argon atmosphere at room temperature for 1.5 hours. Acetic acid (0.1 ml) was added to the reaction mixture followed by concentration. After water (20 ml) was added to the residue, the mixture was extracted with ethyl acetate (20 ml×3). The organic layers were combined, washed with water (50 ml) and with brine (50 ml), and dried over anhydrous magnesium sulfate (20 g) to concentrate, yielding an oily product (1.0275 g).

This oily product was subjected to silica gel column chromatography using ethyl acetate/cyclohexane (6/1)

to resolve into each isomer. First, 16-methyl-15-epi-2,5,6,7-tetranor-18,18,19,19-tetradehydro-4,8-inter-m-phenylene PGI₂ methyl ester was eluted as a less polar fraction (446.8 mg, 1.12 mmol, 42% yield). Subsequently, 16-methyl-2,5,6,7-tetranor-18,18,19,19-tetradehydro-4,8-inter-m-phenylene PGI₂ methyl ester was eluted as a more polar fraction (426.3 mg, 1.07 mmol, 41% yield). These products were assigned the corresponding structures described above by the following data.

16-Methyl-2,5,6,7-tetranor-18,18,19,19-tetradehydro-4,8-inter-m-phenylene PGI₂ methyl ester IR (Liquid Film): 3380, 2948, 2905, 1728, 1592, 1442, 1366, 1335, 1295, 1247, 1187, 1065, 1030, 999, 965, 884, 875, 833, 761, 742 cm⁻¹

NMR (400MHz, CDCl₃, δ): 0.90–1.11 (3H, m); 1.60–1.89 (3H, m); 1.89–3.09 (10H, broad m); 2.27 (2H, broad s); 3.44 (1H, t, J=8.95 Hz); 3.66 (3H, s); 3.74–4.26 (2H, m); 4.98–5.22 (1H, m); 5.55–5.73 (2H, m); 6.61–7.10 (3H, m).

MASS (EI, m/e): 398 (M+).

16-Methyl-15-epi-2,5,6,7-tetranor-18,18,19,19-tetradehydro-4,8-inter-m-phenylene PGI₂ methyl ester IR (KBr): 3275, 2950, 2910, 1738, 1595, 1443, 1343, 1301, 1275, 1222, 1204, 1161, 1100, 1063, 1045, 1010, 960, 922, 888, 862, 840, 780, 765, 743, 620 cm⁻¹.

NMR (400 MHz, CDCl₃, δ): 1.01 (3H, d, J=6.81 Hz); 1.70–1.89 (3H, m); 1.74 (2H, broad s); 1.90–3.05 (10H, broad m); 3.38–3.61 (1H, m); 3.66 (3H, s); 3.81–4.32 (2H, m); 4.97–5.32 (1H, m); 5.61–5.79 (2H, m); 6.65–7.09 (3H, m).

MASS (EI, m/e): 398 (M+).

EXAMPLE 2:
16(R)-Methyl-2,5,6,7-tetranor-18,18,19,19-tetradehydro-4,8-inter-m-phenylene PGI₂ (38) and 16(S)-methyl-2,5,6,7-tetranor-18,18,19,19-tetradehydro-4,8-inter-m-phenylene PGI₂ (39)

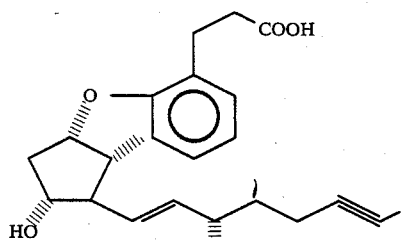
(38)

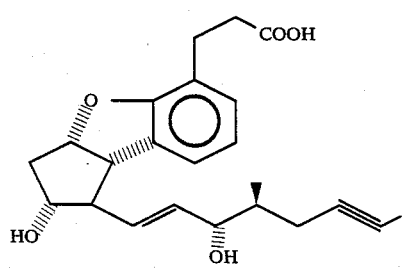
(39)

To a solution of 16-methyl-2,5,6,7-tetranor-18,18,19,19-tetradehydro-4,8-inter-m-phenylene PGI₂ methyl ester (371.2 mg, 0.93 mmol) in methanol (10 ml), there was added an aqueous sodium hydroxide solution (1N, 4.66 ml, 4.66 mmol), and the resulting mixture was stirred at room temperature for 1.5 hours. After hydrochloric acid (1N, 4.8 ml) was added to the reaction mixture, water (20 ml) was also added to the mixture followed by extraction with ethyl acetate (20 ml×3). The organic layers were combined, washed with water (50 ml) and with brine (50 ml), and dried over anhydrous magnesium sulfate (20 g) to concentrate, yielding quantitatively 16-methyl-2,5,6,7-tetranor-18,18,19,19-tetradehydro-4,8-inter-m-phenylene PGI₂ (356.9 mg, 0.93 mmol). The ratio of 16(S)- to 16(R)-isomer thereof was determined by high performance liquid chromatography using methanol/water/acetic acid (55/45/0.1) to be 1.3:1. These isomers were separated by the high performance liquid chromatography using S-343 type column and methanol/water/acetic acid (55/45/0.1) as an eluent. These isomers were assigned the corresponding structures described above by the following data.

16(S)-Methyl-2,5,6,7-tetranor-18,18,19,19-tetradehydro-4,8-inter-m-phenylene PGI₂

Melting Point: 137°–138° C., recrystallized from methanol/cyclohexane (2/5).

IR (KBr): 3460, 3350, 2950, 2902, 1690, 1599, 1450, 1408, 1328, 1290, 1247, 1223, 1184, 1145, 1082, 1064, 1033, 1015, 962, 943, 860, 782, 743 cm⁻¹.

NMR (400 MHz, CDCl₃, δ): 1.02 (3H, d, J=6.84 Hz); 1.79 (3H, t, J=2.44 Hz); 1.93–2.04 (1H, m); 2.07–2.18 (1H, m); 2.22–2.33 (1H, m); 2.39–2.45 (1H, m); 2.59–2.78 (3H, m); 2.82–2.98 (2H, m); 3.43 (1H, t, J=8.30 Hz); 3.89–3.95 (1H, m); 4.13–4.18 (1H, m); 3.5–4.5 (3H, broad s); 5.08–5.17 (1H, m); 5.55–5.75 (2H, m); 6.76 (1H, t, J=7.33 Hz); 6.94–7.03 (2H, m).

MASS (EI, m/e): 384 (M+).

HR MASS: Calcd. (C₂₃H₂₈O₅, M+); 384.1936. Found (M+); 384.1945.

16(R)-Methyl-2,5,6,7-tetranor-18,18,19,19-tetradehydro-4,8-inter-m-phenylene PGI₂

Melting Point: 135°–136° C., recrystallized from ethyl acetate/cyclohexane (⅓).

IR (KBr): 3340, 2955, 2920, 1705, 1595, 1448, 1420, 1370, 1295, 1265, 1245, 1202, 1158, 1071, 1022, 985, 970, 860, 790, 744 cm⁻¹.

NMR (400 MHz, CDCl₃, δ): 0.99 (3H, d, J=6.35 Hz); 1.80 (3H, broad s); 1.71–1.80 (1H, m); 1.93–2.05 (1H, m); 2.22–2.30 (2H, m); 2.40–2.49 (1H, m); 2.58–2.76 (3H, m); 2.82–3.01 (2H, m); 3.44 (1H, t, J=8.55 Hz); 1.9–3.8 (3H, broad s); 3.90–3.97 (1H, m); 4.02–4.08 (1H, m); 5.09–5.17 (1H, m); 5.55–5.72 (2H, m); 6.73–6.81 (1H, m); 6.91–7.01 (2H, m)

MASS (EI, m/e): 384 (M+).

HR MASS: Calcd. (C₂₃H₂₈O₅, M+); 384.1936. Found (M+); 384.1914.

EXAMPLE 3:
16-Methyl-20a-homo-2,5,6,7-tetranor-18,18,19,19-tetradehydro-4,8-inter-m-phenylene PGI$_2$ methyl ester (40) and its 15-epimer (41)

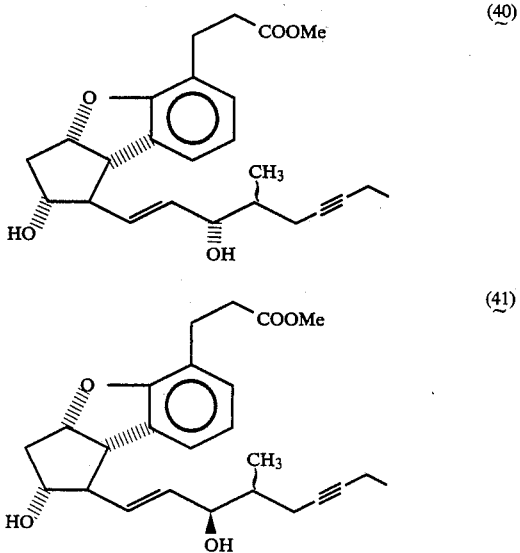

While stirring and ice-cooling, sodium borohydride (0.138 g, 3.39 mmol) was slowly added to a solution of 16-methyl-15-oxo-20a-homo-2,5,6,7-tetranor-18,18,19,19-tetradehydro-4,8-inter-m-phenylene PGI$_2$ methyl ester, 11-acetate (1.1 g, 2.43 mmol) and cerium trichloride heptahydrate (0.91 g, 2.43 mmol) in methanol (50 ml), and the resulting mixture was stirred for 10 minutes. To this reaction mixture there was added a saturated aqueous sodium hydrogencarbonate solution (20 ml). After concentration, water (30 ml) and ethyl acetate (100 ml) were added to the residue. The mixture was filtered and the resulting precipitate was washed with ethyl acetate (30 ml×3). The ethyl acetate layers were combined, washed with water (30 ml) and with brine (30 ml), and dried over anhydrous sodium sulfate to concentrate, yielding an oily material (1.05 g).

To a solution of this oily material in methanol (25 ml), there was added a solution of sodium methoxide in methanol (5.22N, 0.111 ml, 0.58 mmol) while stirring under argon atmosphere, and the resulting mixture was stirred at room temperature for 3 hours. Acetic acid was added to the reaction mixture to neutralize. After concentration, water (20 ml) was added to the residue followed by extraction with ethyl acetate (50 ml×2). The ethyl acetate layers were combined, washed with water (20 ml) and with brine (20 ml), and dried over anhydrous sodium sulfate to concentrate.

the resulting residue was subjected to Merck Lobar silica gel column using ethyl acetate/cyclohexane (2/1) to resolve into each isomer. There were obtained, as a less polar fraction, 16-methyl-15-epi-20a-homo-2,5,6,7-tetranor-18,18,19,19-tetradehydro-4,8-inter-m-phenylene PGI$_2$ methyl ester (402 mg, 0.976 mmol, 42.2% yield); and as a more polar fraction, 16-methyl-20a-homo-2,5,6,7-tetranor-18,18,19,19-tetradehydro-4,8-inter-m-phenylene PGI$_2$ methyl ester (394 mg, 0.956 mmol, 41.4% yield). These products were assigned the corresponding structures described above based on the following data.

16-Methyl-20a-homo-2,5,6,7-tetranor-18,18,19,19-tetradehydro-4,8-inter-m-phenylene PGI$_2$ methyl ester IR (Liquid Film): 3380, 2960, 2930, 1730, 1590, 1440, 1360, 1250, 1185, 1060, 1030, 990, 960, 880, 850, 740 cm$^{-1}$.

NMR (400 MHz, CDCl$_3$, δ): 0.99, 1.03 (3H, d, J=6.8 Hz); 1.12, 1.13 (3H, t, J=7.8 Hz); 1.8–1.85 (1H, m); 1.9–2.0 (1H, m); 2.1–2.3 (4H, m); 2.35–2.45 (1H, m); 2.55–3.0 (7H, m); 3.42, 3.43 (1H, t, J=8.8 Hz); 3.66 (3H, s); 3.85–3.95 (1H, m); 4.04, 4.16 (1H, t, J=6.7 Hz); 5.05–5.15 (1H, m); 5.57, 5.60 (1H, dd, J=6.7, 15.1 Hz); 5.67, 5.68 (1H, dd, J=8.9, 15.1 Hz); 6.755, 6.763 (1H, t, J=7.5 Hz); 6.9–7.0 (2H, m).

MASS (EI, m/e): 412 (M+)

HR MASS: Calcd. (C$_{25}$H$_{32}$O$_5$, M+); 412.2250. Found (M+); 412.2263.

16-Methyl-15-epi-20a-homo-2,5,6,7-tetranor-18,18,19,19-tetradehydro-4,8-inter-m-phenylene PGI$_2$ methyl ester Melting Point: 95.2°–95.9° C., recrystallized from ethyl acetate/n-hexane (2/1).

IR (KBr): 3450, 2960, 2925, 2860, 1740, 1690, 1595, 1450, 1310, 1280, 1260, 1250, 1190, 1145, 1100, 1070, 1035, 990, 960, 860, 745 cm$^{-1}$.

NMR (400 MHz, CDCl$_3$, δ): 1.011, 1.015 (3H, d, J=6.8 Hz); 1.129, 1.131 (3H, t, J=7.3 Hz); 1.8–1.9 (2H, m); 1.95–2.05 (2H, m); 2.15–2.35 (4H, m); 2.45–2.55 (1H, m); 2.6–2.7 (3H, m); 2.85–2.95 (2H, m); 3.45–3.55 (1H, m); 3.66 (3H, s); 3.9–4.0 (1H, m); 4.05–4.15 (1H, m); 4.25–4.3 (1H, m); 5.1–5.2 (1H, m); 5.66, 5.67 (1H, dd, J=8.1, 15.4 Hz); 6.77 (1H, t, J=7.3 Hz); 6.98 (1H, d, J=7.3 Hz); 7.01 (1H, d, J=7.3 Hz).

MASS (EI, m/e): 412 (M+).

Elementary Analysis (C$_{25}$H$_{32}$O$_5$): Calcd. (%): C 72.79; H 7.82, Found (%): C 72.83; H 7.88.

EXAMPLE 4:
16-Methyl-20a-homo-2,5,6,7-tetranor-18,18,19,19-tetradehydro-4,8-inter-m-phenylene PGI$_2$ (42)

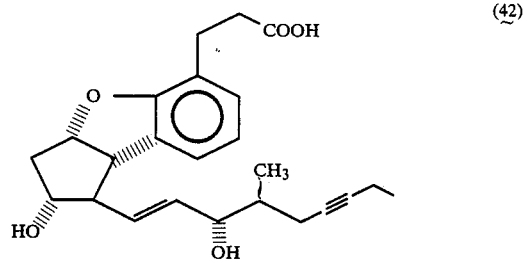

An aqueous sodium hydroxide solution (1N, 5.8 ml, 5.8 mmol) was added to a solution of 16-methyl-20a-homo-2,5,6,7-tetranor-18,18,19,19-tetradehydro-4,8-inter-m-phenylene PGI$_2$ methyl ester (296 mg, 0.72 mmol) in methanol (20 ml ) while stirring and ice-cooling. The resulting mixture was stirred at room temperature for 5 hours followed by concentration. After water (20 ml) was added, 1N hydrochloric acid was used to neutralize the reaction mixture under ice-cooling. The mixture was extracted with ethyl acetate (50 ml×2). Ethyl acetate layers were combined, washed with water (20 ml) and with brine (20 ml), and dried over anhydrous sodium sulfate to concentrate. The residue was recrystallized from a mixture of ethyl acetate (1.5 ml)

and n-hexane (0.5 ml), yielding a white crystal, 16-methyl-20a-homo-2,5,6,7-tetranor-18,18,19,19-tetradehydro-4,8-inter-m-phenylene PGI$_2$ (231 mg, 0.58 mmol, 80.6% yield). This product was assigned the above described structure based on the following data.

Melting Point: 124.2°–125.3° C., recrystallized from ethyl acetate/n-hexane (3/1).

IR (KBr): 3400, 2970, 2930, 1700, 1595, 1455, 1370, 1340, 1315, 1300, 1260, 1195, 1150, 1065, 1015, 985, 960, 915, 850, 820, 800, 780, 740 cm$^{-1}$.

NMR (400 MHz, CDCl$_3$, δ): 0.98, 1.03 (3H, d, J=6.8 Hz); 1.12, 1.13 (3H, t, J=7.3 Hz); 1.7–1.85 (1H, m); 1.95–2.05 (1H, m); 2.1–2.3 (4H, m); 2.35–2.45 (1H, m); 2.6–2.75 (3H, m); 2.8–3.0 (2H, m); 3.41, 3.42 (1H, t, J=8.8 Hz); 3.85–3.95 (1H, m); 4.03, 4.14 (1H, t, J=6.8 Hz); 5.05–5.15 (1H, m); 5.54, 5.57 (1H, dd, J=6.8, 15.4 Hz); 5.64, 5.66 (1H, dd, J=8.5, 15.4 Hz); 4.2–6.0 (2H, m); 6.75, 6.76 (1H, t, J=7.5 Hz); 6.9–7.0 (2H, m).

MASS (EI, m/e): 398 (M+).

Elementary Analysis (C$_{24}$H$_{30}$O$_5$): Calcd. (%): C 72.33; H 7.59, Found (%): C 72.27; H 7.67.

EXAMPLE 5:
16-Methyl-15-epi-20a-homo-2,5,6,7-tetranor-18,18,19,19-tetradehydro-4,8-inter-m-phenylene PGI$_2$ (43)

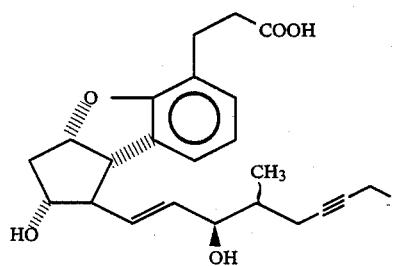

An aqueous sodium hydroxide solution (0.986N, 6.1 ml, 6.0 mmol) was added to a solution of 16-methyl-15-epi-20a-homo-2,5,6,7-tetranor-18,18,19,19-tetradehydro-4,8-inter-m-phenylene PGI$_2$ methyl ester (308 mg, 0.75 mmol) in methanol (25 ml) while stirring and ice-cooling. The reaction mixture was stirred at room temperature for 5 hours. After concentration, water (20 ml) was added to the reaction mixture followed by neutralization with 1N hydrochloric acid. The mixture was extracted with ethyl acetate (50 ml×2). Ethyl acetate layers were combined, washed with water (20 ml) and with brine (20 ml), and dried over anhydrous sodium sulfate to concentrate. The residue was recrystallized from a mixture of ethyl acetate (1.0 ml) and n-hexane (0.5 ml), yielding a white crystal, 16-methyl-15-epi-20a-homo-2,5,6,7-tetranor-18,18,19,19-tetradehydro-4,8-inter-m-phenylene PGI$_2$ (260 mg, 0.65 mmol, 87.1% yield). This product was assigned the above described structure based on the following data.

Melting Point: 107.5°–109.0° C., recrystallized from ethy acetate/n-hexane (2/1).

IR (KBr): 3370, 2970, 2925, 1725, 1705, 1650, 1595, 1475, 1450, 1380, 1340, 1320, 1255, 1220, 1185, 1140, 1090, 1060, 1030, 970, 860, 835, 750 cm$^{-1}$. NMR (400 MHZ, CDCl$_3$, δ): 1.009, 1.014 (3H, d, J=6.8 Hz); 1.13 (3H, t, J=7.3 Hz); 1.75–1.9 (1H, m); 1.95–2.05 (1H, m); 2.15–2.3 (4H, m); 2.45–2.55 (1H, m); 2.6–2.8 (3H, m); 2.85–3.0 (2H, m); 3.45–3.55 (1H, m); 3.9–4.0 (1H, m); 4.11, 4.26 (1H, t, J=5.4 Hz); 5.1–5.2 (1H, m); 5.65, 5.66 (1H, dd, J=7.8, 15.6 Hz); 6.77 (1H, t, J=7.5 Hz); 6.99 (1H, d, J=7.5 Hz); 7.02 (1H, d, J=7.5 Hz).

MASS (EI, m/e): 398 (M+).

Elementary Analysis (C$_{24}$H$_{30}$O$_5$): Calcd. (%): C 72.33; H 7.59. Found (%): C 72.27; H 7.64.

EXAMPLE 6:
16-Methyl-20a,20b-dihomo-2,5,6,7-tetranor-18,18,19,19-tetradehydro-4,8-inter-m-phenylene PGI$_2$ methyl ester (44) and its 15-epimer (45)

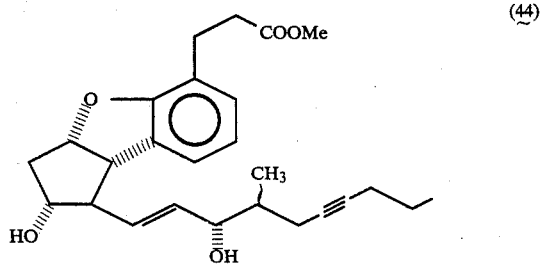

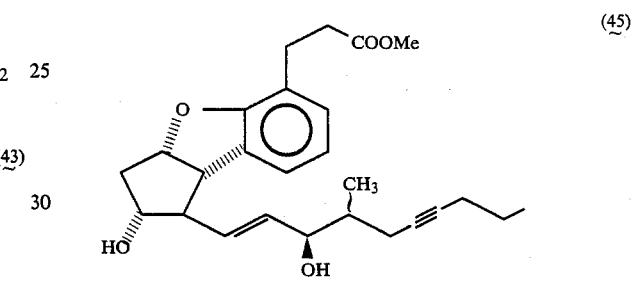

Sodium borohydride (127 mg, 3.35 mmol) was added to a solution of 16-methyl-15-oxo-20a,20b-dihomo-2,5,6,7-tetranor-18,18,19,19-tetradehydro-4,8-inter-m-phenylene PGI$_2$ methyl ester, 11-acetate (1.04 g, 2.23 mmol) and cerium trichloride heptahydrate (835 mg, 2.23 mmmol) in methanol (50 ml) while stirring and ice-cooling, and the resulting mixture was further stirred for 10 minutes. A saturated aqueous sodium hydrogencarbonate solution (20 ml) was added to the reaction mixture. After concentration, water (30 ml) and ethyl acetate (100 ml) were added to the residue followed by filtration. The resulting precipitate was washed with ethyl acetate (30 ml×3). Ethyl acetate layers were combined, washed with water (30 ml) and with brine (30 ml), and dried over anhydrous magnesium sulfate to concentrate, yielding an oily material (1.01 g).

To a solution of this oily material in absolute methanol under argon atmosphere, there was added a solution of sodium methoxide in methanol (5.22N, 0.103 ml, 0.54 mmol), and the resulting mixture was stirred at room temperature for 3 hours. Acetic acid was added to neutralize the reaction mixture followed by concentration. Water (20 ml) was added to the residue and the mixture was extracted with ethyl acetate (50 ml×2). Ethyl acetate layers were combined, washed with water (20 ml) and with brine (20 ml), and dried over anhydrous sodium sulfate to concentrate.

The resulting residue was subjected to Merck Lobar silica gel column using ethyl acetate/n-hexane (2/1) to resolve into each isomer. First, 16-methyl-15-epi-20a,20b-dihomo-2,5,6,7-tetranor-18,18,19,19-tetradehydro-4,8-inter-m-phenylene PGI$_2$ methyl ester was eluted as a less polar fraction (419 mg, 0.984 mmol, 45.5% yield). Subsequently, 16-methyl-20a,20b-dihomo-2,5,6,7-tetranor-18,18,19,19-tetradehydro-4,8-inter-m-phenylene PGI₂ methyl ester was eluted as a more polar fraction (422 mg, 0.991 mmol, 45.9% yield). These products were assigned the corresponding structures described above based on the following data.

16-Methyl-20a,20b-dihomo-2,5,6,7-tetranor-18,18,19,19-tetradehydro-4,8-inter-m-phenylene PGI₂ methyl ester IR (Liquid Film): 3350, 2950, 1725, 1590, 1440, 1360, 1180, 1060, 1025, 1010, 960, 880, 850, 830, 740 cm⁻¹.

NMR (400 MHz, CDCl₃, δ): 0.978, 0.986 (3H, t, J=7.3 Hz); 1.03 (3H, d, J=6.8 Hz); 1.4–1.6 (2H, m); 1.7–1.9 (1H, m); 1.95–2.5 (12H, m); 2.8–3.0 (2H, m); 3.46 (1H, t, J=8.5 Hz); 3.66 (3H, s); 3.8–4.25 (6H, m); 5.0–5.2 (1H, m); 5.5–5.8 (2H, m); 6.76, 6.77 (1H, t, J=7.6 Hz); 6.9–7.1 (2H, m)

MASS (EI, m/e): 426 (M+).

HR MASS: Calcd. (C₂₆H₃₄O₅, M+); 426.2406, Found (M+); 426.2406.

16-Methyl-15-epi-20a,20b-dihomo-2,5,6,7-tetranor-18,18,19,19-tetradehydro-4,8-inter-m-phenylene PGI₂ methyl ester Melting Point: 102.6°–105.8° C., recrystallized from ethyl acetate/n-hexane (2/1).

IR (KBr): 3300, 2950, 1720, 1440, 1365, 1295, 1245, 1185, 1170, 1090, 1060, 1040, 1005, 955, 880, 855, 780, 760, 740 cm⁻¹.

NMR (400 MHz, CDCl₃, δ): 0.978, 0.982 (3H, t, J=7.3 Hz); 1.02 (3H, d, J=6.8 Hz); 1.4–1.6 (2H, m); 1.7–1.9 (2H, m); 1.9–2.1 (2H, m); 2.1–2.4 (3H, m); 2.4–2.7 (4H, m); 2.8–3.0 (2H, m); 3.4–3.6 (1H, m); 3.66 (3H, s); 3.9–4.3 (2H, m); 5.1–5.2 (1H, m); 5.6–5.8 (2H, m); 6.77 (1H, t, J=7.5 Hz); 6.98 (1H, d, J=7.5 Hz); 7.01 (1H, d, J=7.5 Hz).

MASS (EI, m/e): 426 (M+)

Elementary Analysis (C₂₆H₃₄O₅): Calcd. (%): C 73.21; H 8.04, Found (%): C 73.35; H 8.02.

EXAMPLE 7:
16-Methyl-20a,20b-dihomo-2,5,6,7-tetranor-18,18,19,19-tetradehydro-4,8-inter-m phenylene PGI₂
(46)

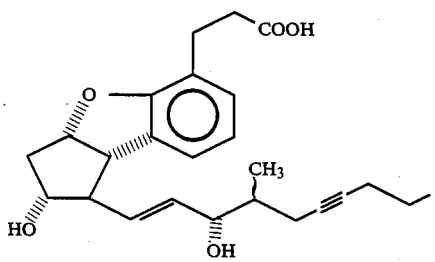

An aqueous sodium hydroxide solution (1N, 5.4 ml, 5.4 mmol) was added to a solution of 16-methyl-20a,20b-dihomo-2,5,6,7-tetranor-18,18,19,19,-tetradehydro-4,8-inter-m-phenylene PGI₂ methyl ester (312 mg, 0.732 mmol) in methanol (25 ml) while stirring and ice-cooling. The resulting mixture was stirred at room temperature for 5 hours. Hydrochloric acid (1N) was added to neutralize the reaction mixture followed by concentration. Water (20 ml) was added to the residue and the resulting mixture was extracted with ethyl acetate (50 ml×2). Ethyl acetate layers were combined, washed with water (20 ml) and with brine (20 ml), and dried over anhydrous sodium sulfate to concentrate. The resulting residue was recrystallized from a mixture of ethyl acetate (1 ml) and n-hexane (0.5 ml), yielding a white crystal, 16-methyl-20a,20b-dihomo-2,5,6,7-tetranor-18,18,19,19-tetradehydro-4,8-inter-m-phenylene PGI₂ (204 mg, 0.495 mmol, 67.6% yield). This product was assigned the above described structure based on the following data.

Melting Point: 104.8°–107.4° C., recrystallized from ethyl acetate/n-hexane (2/1).

IR (Liquid Film): 3350, 2950, 1700, 1585, 1440, 1180, 1060, 960, 880, 850, 830, 760 cm⁻¹.

NMR (400 MHz, CDCl₃, δ): 0.978, 0.986 (3H, t, J=7.3 Hz); 1.04 (3H, d, J=6.8 Hz); 1.4–1.6 (2H, m); 1.7–1.85 (1H, m); 1.9–2.05 (1H, m); 2.1–2.5 (5H, m); 2.55–2.75 (3H, m); 2.8–3.0 (2H, m); 3.43 (1H, t, J=8.5 Hz); 3.85–4.2 (2H, m); 5.05–5.02 (1H, m); 5.5–5.8 (2H, m); 6.76, 6.77 (1H, t, J=7.6 Hz); 6.9–7.1 (2H, m).

MASS (EI, m/e): 412 (M+).

Elementary Analysis (C₂₅H₃₂O₅): Calcd. (%): C 72.79; H 7.82, Found (%): C 72.89; H 7.67.

EXAMPLE 8:
16-Methyl-15-epi-20a,20b-dihomo-2,5,6,7-tetranor-18,18,19,19-tetradehydro-4,8-inter-m-phenylene PGI₂
(47)

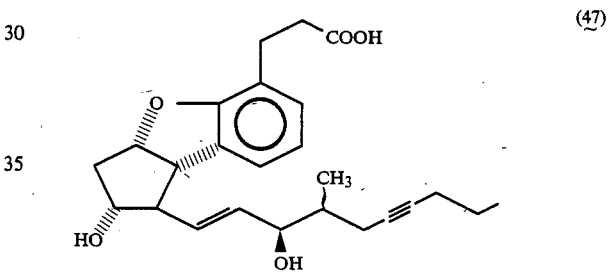

An aqueous sodium hydroxide solution (1N, 7.5 ml, 7.5 mmol) was added to a solution of 16-methyl-15-epi-20a,20b-dihomo-2,5,6,7-tetranor-18,18,19,19-tetradehydro-4,8-inter-m-phenylene PGI₂ methyl ester (322 mg, 0.76 mmol) in methanol (25 ml) while ice-cooling and stirring. The resulting mixture was further stirred at room temperature for 5 hours. The reaction mixture was neutralized by 1N hydrochloric acid. After concentration, water (20 ml) was added to the residue, followed by extraction with ethyl acetate (50 ml×2). The organic layers were combined, washed with water(20 ml) and with brine (20 ml), and dried over anhydrous sodium sulfate to concentrate. The residue was recrystallized from a mixture of ethyl acetate (1 ml) and n-hexane (0.5 ml), yielding a white crystal, 16-methyl-15-epi-20a,20b-dihomo-2,5,6,7-tetranor-18,18,19,19-tetradehydro-4,8-inter-m-phenylene PGI₂ (275 mg, 0.667 mmol, 91.2% yield). This product was assigned the above described structure based on the following data.

Melting Point: 111.0°–114.8° C., recrystallized from ethyl acetate/n-hexane (2/1).

IR (KBr): 3300, 2960, 2925, 1700, 1590, 1445, 1400, 1370, 1330, 1280, 1250, 1210, 1180, 1140, 1090, 1060, 1005, 960, 880, 865, 830, 780, 760, 735 cm⁻¹.

NMR (400 MHz, CDCl₃, δ): 0.978, 0.982 (3H, t, J=7.3 Hz); 1.01, 1.02 (3H, d, J=6.8 Hz); 1.4–1.6 (2H, m); 1.7–1.9 (1H, m); 1.95–2.4 (5H, m); 2.45–2.75 (4H, m); 2.8–3.0 (2H, m); 3.4–3.6 (1H, m); 3.9–4.3 (2H, m);

5.1–5.2 (1H, m); 5.6–5.8 (2H, m); 6.77 (1H, t, J=7.6 Hz); 6.99, 7.02 (2H, d, J=7.6 Hz).

MASS (EI, m/e): 412 (M+).

Elementary Analysis ($C_{25}H_{32}O_5$): Calcd. (%): C 72.79; H 7.82, Found (%): C 72.81; H 7.80.

EXAMPLE 9:

16-Methyl-20a,20b,20c-trihomo-2,5,6,7-tetranor-18,18,19,19-tetradehydro-4,8-inter-m-phenylene $PGI_2$ methyl ester (48) and its 15-epimer (49)

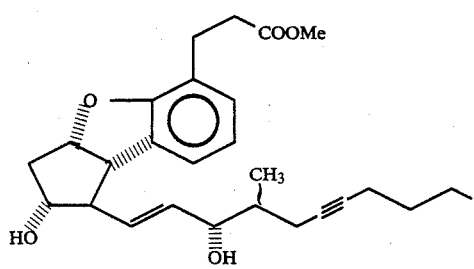
(48)

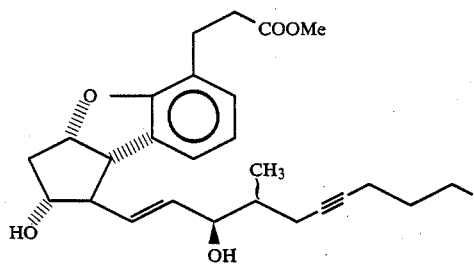
(49)

Sodium borohydride (124 mg, 305 mmol) was added to a solution of 16-methyl-15-oxo-20a,20b,20c-trihomo-2,5,6,7-tetranor-18,18,19,19-tetradehydro-4,8-inter-m-phenylene $PGI_2$ methyl ester, 11-acetate (1.07 g, 2.23 mmol) and cerium trichloride heptahydrate (835 mg, 2.23 mmol) in methanol (50 ml) while stirring and ice-cooling, and the resulting mixture was further stirred for 10 minutes. A saturated aqueous sodium hydrogencarbonate solution (20 ml) was added to the reaction mixture followed by concentration. Water (30 ml) and ethyl acetate (100 ml) were added to the residue. After the mixture was filtered, the resulting precipitate was washed with ethyl acetate (30 ml×3). The ethyl acetate layers were combined, washed with water (30 ml) and with brine (30 ml), and dried over anhydrous sodium sulfate to concentrate, yielding an oily material (1.04 g).

To a solution of this oily material in absolute methanol (25 ml), there was added a solution of sodium methoxide in methanol (5.22N, 0.103 ml, 0.504 mmol) while stirring under argon atmosphere, and the mixture was stirred at room temperature for 3 hours. Acetic acid was added to the reaction mixture to neutralize. After concentration, water (20 ml) was added to the residue followed by extraction with ethyl acetate (50 ml×2). The ethyl acetate layers were combined, washed with water (20 ml) and with brine (20 ml), and dried over anhydrous sodium sulfate to concentrate.

The residue was subjected to Merck Lobar silica gel column using ethyl acetate/cyclohexane (2/1) to resolve into each isomer. There were obtained a less polar fraction, 16-methyl-15-epi-20a,20b,20c-trihomo-2,5,6,7-tetranor-18,18,19,19-tetradehydro-4,8-inter-m-phenylene $PGI_2$ methyl ester (450 mg, 1.02 mmol, 47.2% yield); and a more polar fraction, 16-methyl-20a,20b,20c-trihomo-2,5,6,7-tetranor-18,18,19,19-tetradehydro-4,8-inter-m-phenylene $PGI_2$ methyl ester (437 mg, 0.993 mmol, 46% yield). These products were assigned the corresponding structures described above based on the following data.

16-Methyl-20a,20b,20c-trihomo-2,5,6,7-tetranor-18,18,19,19 -tetradehydro-4,8-inter-m-phenylene $PGI_2$ methyl ester IR (Liquid Film): 3470, 2960, 2930, 2870, 1730, 1595, 1450, 1370, 1340, 1295, 1250, 1190, 1150, 1065, 1030, 1000, 965, 885, 855, 830, 745 cm$^{-1}$.

NMR (400 MHz, CDCl$_3$, δ): 0.908, 0.915 (3H, t, J=7.3 Hz); 0.99, 1.03 (3H, d, J=6.8 Hz); 1.35–1.55 (4H, m); 1.7–1.8 (1H, m); 1.9–2.0 (1H, m); 2.1–2.3 (4H, m); 2.35–2.5 (1H, m); 2.55–2.8 (5H, m); 2.8–2.95 (2H, m); 3.43 (1H, t, J=8.5 Hz); 3.66 (3H, s); 3.85–3.95 (1H, m); 4.0–4.2 (1H, m); 5.05–5.15 (1H, m); 5.5–5.75 (2H, m); 6.7–6.8 (1H, m); 6.9–7.0 (2H, m)

MASS (EI, m/e): 440 (M+).

HR MASS: Calcd. ($C_{27}H_{36}O_5$, M+); 440.2563. Found (M+); 440.2565.

16-Methyl-15-epi-20a,20b,20c-trihomo-2,5,6,7-tetranor-18,18,19,19-tetradehydro-4,8-inter-m-phenylene $PGI_2$ methyl ester Melting Point: 72.3°–96.0° C., recrystallized from ethyl acetate/n-hexane (2/1).

IR (Liquid Film): 3375, 2960, 2930, 2875, 1730, 1595, 1450, 1370, 1340, 1300, 1250, 1190, 1150, 1065, 1030, 1000, 965, 885, 860, 835, 745 cm$^{-1}$.

NMR (400 MHz, CDCl$_3$, δ): 0.91 (3H, t, J=7.3 Hz); 1.02 (3H, d, J=6.8 Hz); 1.35–1.55 (4H, m); 1.75–1.9 (2H, m); 2.0–2.1 (2H, m); 2.15–2.35 (4H, m); 2.45–2.55 (1H, m); 2.55–2.7 (3H, m); 2.85–2.95 (2H, m); 3.45–3.55 (1H, m); 3.66 (3H, s); 3.9–4.0 (1H, m); 4.1–4.3 (1H, m); 5.1–5.2 (1H, m); 5.6–5.8 (2H, m); 6.77 (1H, t, J=7.5 Hz); 6.98 (1H, d, J=7.5 Hz); 7.02 (1H, d, J=7.5 Hz).

MASS (EI, m/e): 440 (M+).

Elementary Analysis ($C_{27}H_{36}O_5$): Calcd. (%): C 73.6; H 8.24, Found (%): C 73.3; H 8.21.

EXAMPLE 10:

16-Methyl-20a,20b,20c-trihomo-2,5,6,7-tetranor-18,18,19,19-tetradehydro-4,8-inter-m-phenylene $PGI_2$ (50)

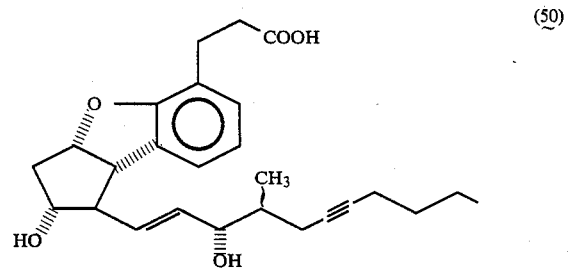
(50)

An aqueous sodium hydroxide solution (0.986N, 6.3 ml, 6.18 mmol) was added to a solution of 16-methyl-20a,20b,20c-trihomo-2,5,6,7-tetranor-18,18,19,19-tetradehydro-4,8-inter-m-phenylene $PGI_2$ methyl ester (340 mg, 0.773 mmol) in methanol (25 ml) while stirring and ice-cooling. The resulting mixture was further stirred at room temperature for 5 hours. Hydrochloric acid (1N, 6.2 ml, 6.2 mmol) was added to the reaction mixture followed by concentration. Water (20 ml) was added to the residdue and the mixture was extracted with ethyl acetate (50 ml×2). Ethyl acetate layers were combined, washed with water (10 ml) and with brine (10 ml), and dried over anhydrous sodium sulfate to concentrate. The residue was recrystallized from a mixture of ethyl acetate (1 ml) and n-hexane (0.4 ml), yielding a white crystal, 16-methyl-20a,20b,20c-trihomo-2,5,6,7-tetranor-18,18,19,19-tetradehydro-4,8-inter-m-phenylene PGI$_2$ (240 mg, 0.563 mmol, 72.9% yield). This product was assigned the above described structure based on the following data.

Melting Point: 70.8°–99.2° C., recrystallized from ethyl acetate/n-hexane (5/2).

IR (KBr): 3400, 2950, 2920, 2860, 1690, 1590, 1450, 1420, 1370, 1290, 1260, 1240, 1200, 1140, 1065, 1015, 990, 960, 920, 850, 820, 800, 780, 760, 740 cm$^{-1}$.

NMR (400 MHz, CDCl$_3$, δ): 0.909, 0.915 (3H, t, J=7.3 Hz); 0.99, 1.03 (3H, d, J=7.0 Hz); 1.35–1.55 (4H, m); 1.75–1.85 (1H, m); 1.95–2.05 (1H, m); 2.1–2.3 (4H, m); 2.4–2.5 (1H, m); 2.6–2.8 (3H, m); 2.8–3.0 (2H, m); 3.44 (1H, t, J=8.5 Hz); 3.85–3.95 (1H, m); 4.0–4.2 (1H, m); 5.05–5.15 (1H, m); 5.55–5.75 (2H, m); 6.762, 6.766 (1H, t, J=7.3 Hz); 6.9–7.0 (2H, m).

MASS (EI, m/e): 426 (M+).

Elementary Analysis (C$_{26}$H$_{34}$O$_5$): Calcd. (%): C 73.21; H 8.04, found (%): C 72.9; H 8.05.

EXAMPLE 11:
16-Methyl-15-epi-20a,20b,20c-trihomo-2,5,6,7-tetranor-18,18,19,19-tetradehydro-4,8-inter-m-phenylene PGI$_2$(51)

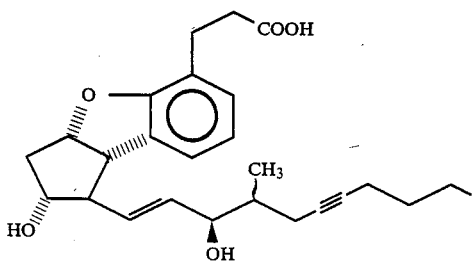

An aqueous sodium hydroxide solution (0.986N, 6.4 ml, 6.31 mmol) was added to a solution of 16-methyl-15-epi-20a,20b,20c-trihomo-2,5,6,7-tetranor-18,18,19,19-tetradehydro-4,8-inter-m-phenylene PGI$_2$ methyl ester (347 mg, 0.79 mmol) in methanol (25 ml) while stirring and ice-cooling. The resulting mixture was stirred at room temperature for 5 hours. Hydrochloric acid (1N, 6.4 ml, 6.4 mmol) was added to the reaction mixture while ice-cooling, followed by concentration. Water (20 ml) was added to the residue and the mixture was extracted with ethyl acetate (50 ml×2). The ethyl acetate layers were combined, washed with water (20 ml) and with brine (20 ml), and dried over anhydrous sodium sulfate to concentrate. The resulting residue was recrystallized from a mixture of ethyl acetate (1.0 ml) and n-hexane (0.5 ml), yielding a white crystal, 16-methyl-15-epi-20a,20b,20c-trihomo-2,5,6,7-tetranor-18,18,19,19-tetradehydro-4,8-inter-m-phenylene PGI$_2$ (291 mg, 0.683 mmol, 86.5% yield). This product was assigned the above described structure based on the following data.

Melting Point: 99.5°–114.5° C., recrystallized from ethyl acetate/n-hexane (2/1).

IR (KBr): 3320, 2960, 2920, 1725, 1700, 1650, 1590, 1450, 1370, 1340, 1320, 1300, 1260, 1220, 1185, 1140, 1090, 1080, 1000, 970, 890, 860, 740 cm$^{-1}$.

NMR (400 MHz, CDCl$_3$, δ): 0.91 (3H, t, J=7.3 Hz); 1.01, 1.02 (3H, d, J=6.8 Hz); 1.35–1.55 (4H, m); 1.75–1.9 (1H, m); 2.0–2.1 (1H, m); 2.1–2.35 (4H, m); 2.45–2.75 (4H, m); 2.8–3.0 (2H, m); 3.45–3.55 (1H, m); 3.9–4.0 (1H, m); 5.6–5.8 (2H, m); 6.78 (1H, t, J=7.5 Hz); 6.99 (1H, d, J=7.5 Hz); 7.02 (1H, d, J=7.5 Hz).

MASS (EI, m/e): 426 (M+).

Elementary Analysis (C$_{26}$H$_{34}$O$_5$): Calcd. (%): C 73.21; H 8.04, Found (%): C 72.79; H 7.95.

EXAMPLE 12:
16,16-Dimethyl-2,5,6,7-tetranor-18,18,19,19-tetradehydro-4,8-inter-m-phenylene PGI$_2$ methyl ester (52) and its 15-epimer (53)

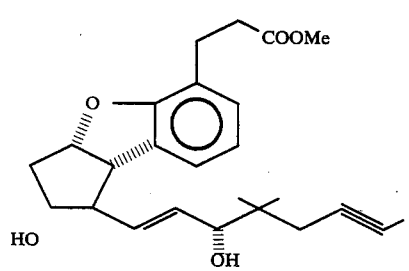

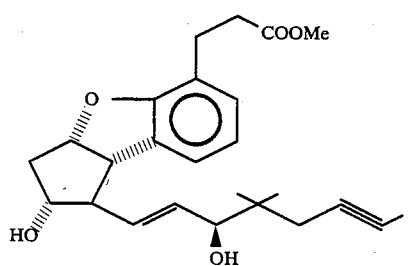

Sodium borohydride (72.5 mg, 1.73 mmol) was added to a solution of 16,16-dimethyl-15-oxo-2,5,6,7-tetranor-18,18,19,19-tetradehydro-4,8-inter-m-phenylene PGI$_2$ methyl ester, 11-acetate (780 mg, 1.73 mmol) and cerium trichloride heptahydrate (771.5 mg, 2.07 mmol) in methanol (10 ml) while stirring and ice-cooling, and the resulting mixture was further stirred for 10 minutes. Water (20 ml) was added to the reaction mixture followed by stirring for 10 minutes. The mixture was extracted with ethyl acetate (15 ml×3). The organic layers were combined, washed with water (50 ml) and with brine (50 ml), and dried over anhydrous sodium sulfate (20 g) to concentrate, yielding an oily material (760.5 mg).

This oily material was azeotropically distilled with benzene (10 ml×2). To a solution of the resulting residue in absolute methanol (10 ml), there was added sodium methoxide (4.89N, 0.01 ml, 0.07 mmol), and the whole mixture was stirred under argon atmosphere at room temperature for 2 hours. Acetic acid (0.1 ml) was added to the reaction mixture followed by concentration. Water (10 ml) was added to the residue and the mixture was extracted with ethyl acetate (10 ml×3). The organic layers were combined, washed with water (30 ml) and with brine (30 ml), and dried over anhydrous sodium sulfate (15 g) to concentrate, yielding an oily product (762.5 mg).

The oily product was subjected to silica gel column chromatography using ethyl acetate/cyclohexane (6/1) to resolve into each isomer. First, there was eluted a less polar fraction, 16,16-dimethyl-15-epi-2,5,6,7-tetranor-18,18,19,19-tetradehydro-4,8-inter-m-phenylene PGI$_2$ methyl ester (294.1 mg, 0.71 mmol, 42% yield), which was then recrystallized from ethyl acetate/cyclohexane (2/3) to afford a colorless needle-like crystal. Subsequently, there was eluted a more polar fraction, 16,16-dimethyl-2,5,6,7-tetranor-18,18,19,19-tetradehydro-4,8-inter-m-phenylene PGI$_2$ methyl ester (280.6 mg, 0.68 mmol, 40% yield). These products were assigned the corresponding structures described above based on the following data.

16,16-Dimethyl-2,5,6,7-tetranor-18,18,19,19-tetradehydro-4,8-inter-m-phenylene PGI$_2$ methyl ester IR (Liquid Film): 3400, 2951, 1735, 1598, 1443, 1362, 1301, 1253, 1190, 1090, 1063, 1031, 1001, 970, 887, 861, 835, 744 cm$^{-1}$.

NMR (400 MHz, CDCl$_3$, δ): 0.97 (3H, s); 0.98 (3H, s); 1.81 (3H, t, J=2.44 Hz); 1.90–2.27 (5H, m); 2.43–2.51 (1H, m); 2.61–2.72 (3H, m); 2.85–2.96 (2H, m); 3.46 (1H, t, J=8.55 Hz); 3.66 (3H, s); 3.92–3.97 (1H, m); 4.02–4.05 (1H, m); 5.10–5.17 (1H, m); 5.67–5.77 (2H, m); 6.77 (1H, t, J=7.33 Hz); 6.94–7.02 (2H, m).

MASS (EI, m/e): 412 (M+).

HR MASS: Calcd. (C$_{25}$H$_{32}$O$_5$, M+); 412.2250. Found (M+); 412.2216.

16,16-Dimethyl-15-epi-2,5,6,7-tetranor-18,18,19,19-tetradehydro-4,8-inter-m-phenylene PGI$_2$ methyl ester Melting Point: 100° C.

IR (KBr): 3350, 2952, 1730, 1596, 1435, 1410, 1360, 1304, 1275, 1245, 1224, 1185, 1163, 1111, 1060, 1020, 1000, 978, 950, 905, 865, 837, 810, 764, 743, 655, 615 cm$^{-1}$.

NMR (400 MHz, CDCl$_3$, δ): 0.98 (6H, s); 1.57–1.87 (2H, broad s); 1.81 (3H, t, J=2.45 Hz); 2.01–2.11 (2H, m); 2.19–2.27 (1H, m); 2.52–2.57 (1H, m); 2.62–2.66 (3H, m); 2.87–2.95 (2H, m); 3.52 (1H, t, J=8.06 Hz); 3.66 (3H, s); 3.94–4.01 (1H, m); 4.05–4.06 (1H, m); 5.13–5.18 (1H, m); 5.72–5.78 (2H, m); 6.77 (1H, t, J=7.33 Hz); 6.98 (1H, d, J=7.33 Hz); 7.02 (1H, d, J=7.33 Hz).

MASS (EI, m/e): 412 (M+).

Elementary Analysis (C$_{25}$H$_{32}$O$_5$): Calcd. (%): C 72.79; H 7.82, Found (%): C 72.77; H 7.81.

EXAMPLE 13:
16,16-Dimethyl-2,5,6,7-tetranor-18,18,19,19-tetradehydro-4,8-inter-m-phenylene PGI$_2$ (54)

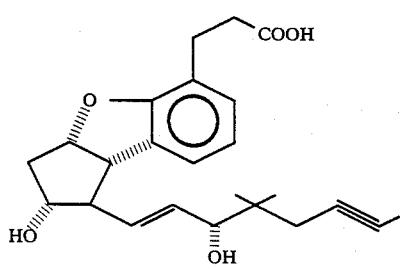

(54)

An aqueous sodium hydroxide solution (1N, 2.8 ml, 2.8 mmol) was added to a solution of 16,16-dimethyl-2,5,6,7-tetranor-18,18,19,19-tetradehydro-4,8-inter-m-phenylene PGI$_2$ methyl ester (232.3 mg, 0.56 mmol) in methanol (6 ml) and the resulting mixture was stirred under argon atmosphere at room temperature for 2 hours. To the reaction mixture there were added hydrochloric acid (1N, 3 ml) and water (15 ml), followed by extraction with ethyl acetate (15 ml×3). The organic layers were combined, washed with water (50 ml) and with brine (50 ml), and dried over anhydrous sodium sulfate (25 g) to concentrate, yielding quantitatively 16,16-dimethyl-2,5,6,7-tetranor-18,18,19,19-tetradehydro-4,8-inter-m-phenylene PGI$_2$ (222.4 mg, 0.56 mmol) as a single product. This product was recrystallized from ethyl acetate/cyclohexane (2/1) to afford a colorless needle-like crystal. This product was assigned the above described structure based on the following data.

Melting Point: 120.5°–121° C.

IR (KBr): 3340, 2963, 2926, 1701, 1598, 1449, 1418, 1296, 1264, 1244, 1203, 1070, 1021, 995, 963, 912, 898, 858, 829, 805, 787, 768, 743 cm$^{-1}$.

NMR (400 MHz, CDCl$_3$, δ): 0.96 (3H, s); 0.97 (3H, s); 1.81 (3H, t, J=2.44 Hz); 1.96–2.12 (2H, m); 2.18–2.25 (1H, m); 2.42–2.52 (1H, m); 2.60–2.76 (3H, m); 2.82–3.00 (2H, m); 2.60–3.88 (3H, broad s); 3.45 (1H, t, J=8.57 Hz); 3.90–3.96 (1H, m); 4.02–4.05 (1H, m); 5.10–5.15 (1H, m); 5.62–5.72 (2H, m); 6.77 (1H, t, J=7.33 Hz); 6.96 (1H, d, J=7.33 Hz); 6.98 (1H, d, J=7.33 Hz).

MASS (EI, m/e): 398 (M+)

HR MASS: Calcd. (C$_{24}$H$_{30}$O$_5$, M+); 398.2096, Found (M+); 398.2113.

EXAMPLE 14:
16,16-Dimethyl-20a-homo-2,5,6,7-tetranor-18,18,19,19-tetradehydro-4,8-inter-m-phenylene PGI$_2$ methyl ester (55) and its 15-epimer (56)

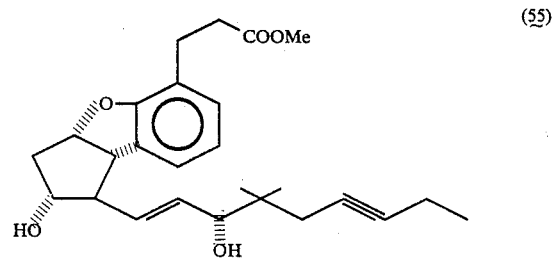

(55)

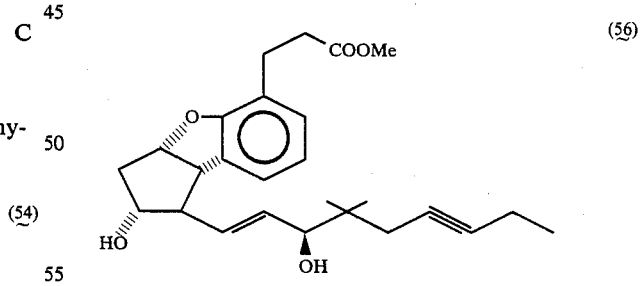

(56)

Sodium borohydride (99.6 mg, 2.37 mmol) was added to a solution of 16,16-dimethyl-15-oxo-20a-homo-2,5,6,7-tetranor-18,18,19,19-tetradehydro-4,8-inter-m-phenylene PGI$_2$ methyl ester, 11-acetate (1.107 g, 2.37 mmol) and cerium trichloride heptahydrate (1.06 g, 2.84 mmol) in methanol (10 ml) while stirring and ice-cooling, and the resulting mixture was further stirred for 10 minutes. Water (20 ml) was added to the reaction mixture followed by stirring for 10 minutes. The mixture was extracted with ethyl acetate (15 ml×3). The organic layers were combined, washed with water (50 ml) and with brine (50 ml), and dried over anhydrous sodium sulfate (20 g) to concentrate, yielding an oily material (1.171 g).

This oily material was azeotropically distilled with benzene (10 ml×2). To a solution of the resulting residue in absolute methanol (10 ml), there was added sodium methoxide (5.22N, 0.02 ml, 0.09 mmol), and the mixture was stirred under argon atmosphere at room temperature for one hour. Acetic acid (0.1 ml) was added to the reaction mixture followed by concentration. Water (20 ml) was added to the residue and the mixture was extracted with ethyl acetate (15 ml×3). The organic layers were combined, washed with water (50 ml) and with brine (50 ml), and dried over anhydrous sodium sulfate (25 g) to concentrate, yielding an oily product (1.0357 g).

This oily product was resolved into each isomer by column chromatography using silica gel and ethyl acetate/cyclohexane (3/1): First, there was eluted, as a less polar fraction, 16,16-dimethyl-15-epi-20a-homo-2,5,6,7-tetranor-18,18,19,19-tetradehydro-4,8-inter-m-phenylene PGI$_2$ methyl ester (434.3 mg, 1.02 mmol, 43% yield), which was then recrystallized from ethyl acetate/cyclohexane (1/2) to afford a colorless needle-like crystal. Subsequently, there was eluted, as a more polar fraction, 16,16-dimethyl-20a-homo-2,5,6,7-tetranor-18,18,19,19-tetradehydro-4,8-inter-m-phenylene PGI$_2$ methyl ester (425.5 mg, 1.00 mmol, 42% yield). These products were assigned the corresponding structures described above based on the following data.

16,16-Dimethyl-20a-homo-2,5,6,7-tetranor-18,18,19,19-tetradehydro-4,8-inter-m-phenylene PGI$_2$ methyl ester IR (Liquid Film): 3400, 2960, 1730, 1600, 1450, 1365, 1320, 1300, 1260, 1195, 1095, 1068, 1034, 1002, 964, 888, 860, 840, 744 cm$^{-1}$.

NMR (400 MHz, CDCl$_3$, δ): 0.97 (3H, s); 0.98 (3H, s); 1.13 (3H, t, J=7.57 Hz); 1.90-1.98 (1H, m); 2.06-2.25 (5H, m); 2.35-2.42 (1H, m); 2.63-2.72 (3H, m); 2.86-2.92 (2H, m); 3.22-3.42 (1H, m); 3.40 (1H, t, J=8.79 Hz); 3.66 (3H, s); 3.84-3.91 (1H, m); 3.98-4.02 (1H, m); 5.06-5.13 (1H, m); 5.61-5.70 (2H, m); 6.76 (1H, t, J=7.33 Hz); 6.92-7.03 (2H, m)

MASS (EI, m/e): 426 (M+).

HR MASS: Calcd. (C$_{26}$H$_{34}$O$_6$, M+); 426.2405, Found (M+); 426.2393.

16,16-Dimethyl-15-epi-20a-homo-2,5,6,7-tetranor-18,18,19,19-tetradehydro-4,8-inter-m-phenylene PGI$_2$ methyl ester Melting Point: 76°-77° C.

IR (KBr): 3300, 2960, 1730, 1600, 1445, 1368, 1303, 1267, 1247, 1190, 1172, 1100, 1090, 1066, 1050, 1010, 975, 958, 948, 882, 858, 847, 767, 741, 599 cm$^{-1}$.

NMR (400 MHz, CDCl$_3$, δ): 0.98 (6H, s); 1.14 (3H, t, J=7.57 Hz); 1.72-1.78 (1H, m); 1.98-2.29 (6H, m); 2.51-2.58 (1H, m); 2.61-2.69 (3H, m); 2.84-2.95 (2H, m); 3.52 (1H, t, J=8.30 Hz); 3.66 (3H, s); 3.94-4.03 (1H, m); 4.05-4.08 (1H, m); 5.12-5.19 (1H, m); 5.70-5.78 (2H, m); 6.78 (1H, t, J=7.33 Hz); 6.98 (1H, d, J=7.33 Hz); 7.02 (1H, d, J=7.33 Hz).

MASS (EI, m/e): 426 (M+).

HR MASS: Calcd. (C$_{26}$H$_{34}$O$_5$, M+); 426.2405, Found (M+); 426.2375.

EXAMPLE 15:
16,16-Dimethyl-20a-homo-2,5,6,7-tetranor-18,18,19,19-tetradehydro-4,8-inter-m-phenylene PGI$_2$ (57)

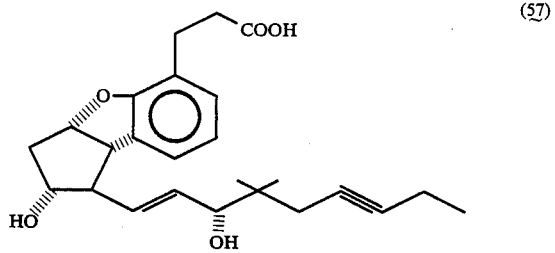

(57)

An aqueous sodium hydroxide solution (1N, 3.1 ml, 3.1 mmol) was added to a solution of 16,16-dimethyl-20a-homo-2,5,6,7-tetranor-18,18,19,19-tetradehydro-4,8-inter-m-phenylene PGI$_2$ methyl ester (260.1 mg, 0.61 mmol) in methanol (8 ml), and the resulting mixture was stirred under argon atmosphere at room temperature for 2 hours. Hydrochloric acid (1N, 3.2 ml) was added to the reaction mixture to neutralize. Water (15 ml) was added to the mixture followed by extraction with ethyl acetate (15 ml×3). The organic layers were combined, washed with water (50 ml) and with brine (50 ml), and dried over anhydrous magnesium sulfate (25 g) to concentrate, yielding quantitatively 16,16-dimethyl-20a-homo-2,5,6,7-tetranor-18,18,19,19-tetradehydro-4,8-inter-m-phenylene PGI$_2$ (250.6 mg, 0.61 mmol) as a single product. This was recrystallized from ethyl acetate/cyclohexane (2/1) to afford a colorless needle-like crystal. This product was assigned the above described structure based on the following data.

Melting Point: 134.5°-135.5° C.

IR (KBr): 3400 (3650-2250), 2962, 2927, 1705, 1601, 1456, 1321, 1295, 1264, 1246, 1205, 1070, 1022, 993, 960, 924, 849, 828, 807, 781, 767, 740 cm$^{-1}$.

NMR (400 MHz, CDCl$_3$, δ): 0.98 (6H, s); 1.14 (3H, t, J=7.32 Hz); 1.96-2.08 (1H, m); 2.08-2.25 (5H, m); 2.43-2.52 (1H, m); 2.62-2.78 (4H, m); 2.84-2.98 (2H, m); 3.47 (1H, t, J=8.55 Hz); 3.92-3.99 (1H, m); 4.03-4.06 (1H, m); 5.11-5.18 (1H, m); 5.64-5.73 (2H, m); 6.77 (1H, t, J=7.33 Hz); 6.97-7.03 (2H, m).

MASS (EI, m/e): 412 (M+).

Elementary Analysis (C$_{25}$H$_{32}$O$_5$): Calcd. (%): C 72.80; H 7.82, Found (%): C 72.71; H 7.77.

EXAMPLE 16:
16,16-Dimethyl-20a,20b,20c-trihomo-2,5,6,7-tetranor-18,18,19,19-tetradehydro-4,8-inter-m-phenylene PGI$_2$ methyl ester (58) and its 15-epimer (59)

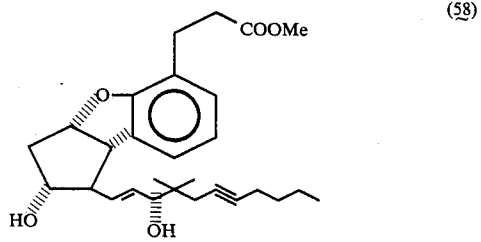

(58)

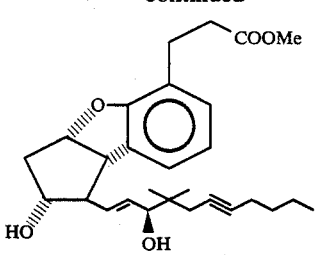

(59)

While stirring an ice-cooling, sodium borohydride (108.9 mg, 2.59 mmol) was added to a solution of 16,16-dimethyl-15-oxo-20a,20b,20c-trihomo-2,5,6,7-tetranor-18,18,19,19-tetradehydro-4,8-inter-m-phenylene PGI₂ methyl ester, 11-acetate (1.2811 g, 2.59 mmol) and cerium trichloride heptahydrate (1.16 g, 3.11 mmol) in methanol (12 ml), and the resulting mixture was further stirred for 10 minutes. After water (20 ml) was added, the reaction mixture was stirred for 10 minutes followed by concentration. The residue was extracted with ethyl acetate (20 ml×3). The organic layers were combined, washed with water (50 ml) and with brine (50 ml), and dried over anhydrous sodium sulfate (20 g) to concentrate, yielding an oily material (1.5114 g).

This oily material was azeotropically distilled with benzene (10 ml×2). To a solution of the resulting residue in absolute methanol (12 ml) there was added sodium methoxide (5.22N, 0.02 ml, 0.10 mmol), and the mixture was stirred under argon atmosphere at room temperature for 3 hours. Acetic acid (0.05 ml) was added to the reaction mixture followed by concentration. Water (15 ml) was added to the residue and the resulting mixture was extracted with ethyl acetate (15 ml×3). The organic layers were combined, washed with water (50 ml) and with brine (50 ml), and dried over anhydrous sodium sulfate (20 g) to concentrate, yielding an oily product (1.3813 g).

This oily product was subjected to silica gel column chromatography using ethyl acetate/cyclohexane (1/1) to resolve into each isomer. There were eluted first, as a less polar fracton, 16,16-dimethyl-15-epi-20a,20b,20c-trihomo-2,5,6,7-tetranor-18,18,19,19-tetradehydro-4,8-inter-m-phenylene PGI₂ methyl ester (539.5 mg, 1.19 mmol, 46% yield); and subsequently, as a more polar fraction, 16,16-dimethyl-20a,20b,20c-trihomo-2,5,6,7-tetranor-18,18,19,19-tetradehydro-4,8-inter-m-phenylene PGI₂ methyl ester (517.0 mg, 1.14 mmol, 44% yield), which was then recrystallized from ethyl acetate/n-hexane (1/1) to afford a colorless needle-like crystal. These compounds were assigned the corresponding structures described above based on the following data.

16,16-Dimethyl-20a,20b,20c-trihomo-2,5,6,7-tetranor-18,18,19,19-tetradehydro-4,8-inter-m-phenylene PGI₂ methyl ester Melting Point: 52°–53° C.

IR (KBr): 3310, 2951, 2910, 1731, 1660, 1615, 1599, 1444, 1419, 1360, 1343, 1320, 1251, 1220, 1205, 1181, 1161, 1094, 1063, 1050, 1039, 1005, 999, 983, 950, 890, 874, 863, 843, 810, 780, 744, 664, 616 cm⁻¹.

NMR (400 MHz, CDCl₃, δ): 0.91 (3H, t, J=7.32 Hz); 0.98 (6H, s); 1.37–1.51 (4H, m); 1.58 (1H, broad s); 1.75∝1.76 (1H, broad s); 1.98–2.28 (5H, m); 2.50–2.56 (1H, m); 2.59–2.71 (3H, m); 2.84–2.96 (2H, m); 3.52 (1H, t, J=8.30 Hz); 3.93–4.01 (1H, m); 4.03–4.08 (1H, m); 5.13–5.29 (1H, m); 5.67–5.78 (2H, m); 6.78 (1H, t, J=7.33 Hz); 6.98 (1H, d, J=7.33 Hz); 7.02 (1H, d, J=7.33 Hz).

MASS (EI, m/e): 454 (M⁺).

Elementary Analysis (C₂₈H₃₈O₅): Calcd. (%): C 73.90; H 8.50, Found (%): C 73.98; H 8.42.

16,16-Dimethyl-15-epi-20a,20b,20c-trihomo-2,5,6,7-tetranor-18,18,19,19-tetradehydro-4,8-inter-m-phenylene PGI₂ methyl ester IR (Liquid Film): 3400, 2950, 2940, 2870, 1735, 1595, 1446, 1362, 1299, 1252, 1190, 1170, 1150, 1090, 1063, 1030, 1000, 967, 886, 859, 838 cm⁻¹.

NMR (400 MHz, CDCl₃, δ): 0.91 (3H, t, J=7.33 Hz); 0.96 (3H, s); 0.98 (3H, s); 1.35–1.52 (4H, m); 1.87–1.96 (1H, broad s); 2.05–2.24 (4H, m); 2.30–2.40 (1H, broad s); 2.59–2.72 (3H, m); 2.84–2.92 (2H, m); 3.02–3.13 (1H, m); 3.36–3.41 (1H, m); 3.55–3.68 (1H, m); 3.66 (3H, s); 3.81–3.99 (1H, m); 3.93–4.03 (1H, m); 5.04–5.12 (1H, m); 5.58–4.69 (2H, m); 6.75 (1H, t, J=7.33 Hz); 6.93 (1H, d, J=7.33 Hz); 6.96 (1H, d, J=7.33 Hz).

MASS (EI, m/e): 454 (M⁺).

HR MASS: Calcd. (C₂₈H₃₈O₅, M⁺); 454.2719, Found (M⁺); 454.2713.

EXAMPLE 17:
16,16-Dimethyl-20a,20b,20c-trihomo-2,5,6,7-tetranor-18,18,19,19-tetradehydro-4,8-inter-m-phenylene PGI₂
(60)

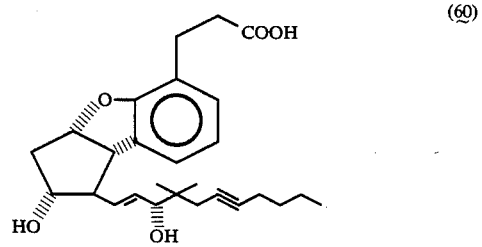

(60)

An aqueous sodium hydroxide solution (1N, 2.7 ml, 2.7 mmol) was added to a solution of 16,16-dimethyl-20a,20b,20c-trihomo-2,5,6,7-tetranor-18,18,19,19-tetradehydro-4,8-inter-m-phenylene PGI₂ methyl ester (245.9 mg, 0.54 mmol) in methanol (10 ml) and the mixture was stirred under argon atmosphere at room temperature for 4 hours. Hyrdrochloric acid (1N, 4 ml) was added to the reaction mixture. Water (20 ml) was further added to the mixture followed by extraction with ethyl acetate (20 ml×3). The organic layers were combined, washed with water (50 ml) and with brine (50 ml), and dried over anhydrous magnesium sulfate (20 g) to concentrate, yielding 16,16-dimethyl-20a,20b,20c-trihomo-2,5,6,7-tetranor-18,18,19,19-tetradehydro-4,8-inter-m-phenylene PGI₂ (232.1 mg, 0.53 mmol, 98% yield) as a single product. This product was recrystallized from ethyl acetate/cyclohexane (2/3) to afford a colorless needle-like crystal. This product was assigned the above described structure based on the following data.

Melting Point: 84°–84.5° C.

IR (KBr): 3350 (2200–3700), 2950, 2920, 1703, 1599, 1445, 1379, 1362, 1253, 1182, 1150, 1082, 1059, 1020, 999, 962, 943, 893, 862, 839, 743 cm⁻¹.

NMR (400 MHz, CDCl₃, δ): 0.91 (1H, t, J=7.33 Hz); 0.98 (6H, s); 1.37–1.52 (4H, m); 1.98–2.27 (5H, m); 2.50–2.56 (1H, m); 2.57–2.76 (5H, m); 2.84–2.97 (3H, m); 3.51 (1H, t, J=8.3 Hz); 3.93–4.00 (1H, m); 4.04–4.07

(1H, m); 5.13–5.20 (1H, m); 5.68–5.77 (2H, m); 6.78 (1H, t, J=7.33 Hz); 6.99 (1H, d, J=7.33 Hz); 7.02 (1H, d, J=7.33 Hz).

MASS (EI, m/e): 440 (M+).

Elementary Analysis ($C_{27}H_{36}O_5$): Calcd. (%): C 73.61; H 8.24, Found (%): C 73.33; H 8.28.

EXAMPLE 18:
16,16-Dimethyl-15-epi-20a,20b,20c-trihomo-2,5,6,7-tetranor-18,18,19,19-tetradehydro-4,8-inter-m-phenylene $PGI_2$ (61)

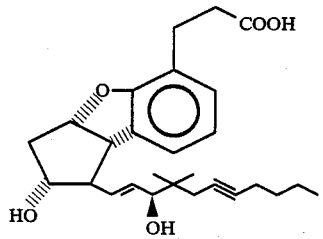

(61)

An aqueous sodium hydroxide solution (1N, 3 ml, 3 mmol) was added to a solution of 16,16-dimethyl-15-epi-20a,20b,20c-trihomo-2,5,6,7-tetranor-18,18,19,19-tetradehydro-4,8-inter-m-phenylene $PGI_2$ methyl ester (265.5 mg, 0.59 mmol) in methanol (10 ml), and the resulting mixture was stirred under argon atmosphere at room temperature for 3 hours. Hydrochloric acid (1N, 4 ml) was added to the reaction mixture to neutralize. After water (20 ml) was added, the mixture was extracted with ethyl acetate (15 ml×3). The organic layers were combined, washed with water (50 ml) and with brine (50 ml), and dried over anhydrous magnesium sulfate (20 g) to concentrate, yielding quantitatively 16,16-dimethyl-15-epi-20a,20b,20c-trihomo-2,5,6,7-tetranor-18,18,19,19-tetradehydro-4,8-inter-m-phenylene $PGI_2$ (255.1 mg, 0.59 mmol) as a single product. This was recrystallized from ethyl acetate/cyclohexane (3/2) to afford a colorless needle-like crystal. This product was assigned the above described structure by the following data.

Melting Point: 111°–112° C.

IR (KBr): 3410 (3675–2290), 2955, 2930, 2870, 1702, 1598, 1457, 1422, 1377, 1360, 1341, 1299, 1243, 1202, 1140, 1070, 1008, 990, 965, 924, 903, 860, 830, 788, 771, 745, 728 cm$^{-1}$.

NMR (400 MHz, CDCl$_3$, δ): 0.91 (3H, t, J=7.33 Hz); 0.98 (6H, s); 1.37–1.53 (4H, m); 1.94–2.03 (1H, m); 2.06–2.27 (5H, m); 2.42–2.48 (1H, m); 2.59–2.75 (3H, m); 2.83–2.97 (3H, m); 3.43–3.48 (1H, m); 3.90–3.96 (1H, m); 4.02–4.04 (1H, m); 5.10–5.16 (1H, m); 5.62–5.72 (2H, m); 6.77 (1H, t, J=7.32 Hz); 6.96 ∝ 7.00 (2H, m).

MASS (EI, m/e): 440 (M+).

Elementary Analysis ($C_{27}H_{36}O_5$): Calcd. (%): C 73.61; H 8.24, Found (%): C 73.45; H 8.28.

EXAMPLE 19:
16,16-Dimethyl-20a,20b,20c,20d-tetrahomo-2,5,6,7-tetranor-18,18,19,19-tetradehydro-4,8-inter-m-phenylene $PGI_2$ methyl ester (62) and its 15-epimer (63)

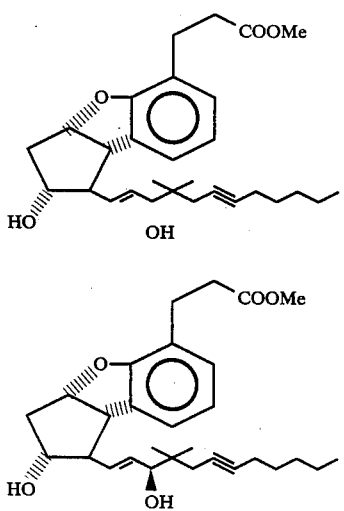

Sodium borohydride (123.6 mg, 2.94 mmol) was added to a solution of 16,16-dimethyl-15-oxo-20a,20b,20c,20d-tetrahomo-2,5,6,7-tetranor-18,18,19,19-tetradehydro-4,8-inter-m-phenylene $PGI_2$ methyl ester, 11-acetate (1.4915 g, 2.94 mmol) and cerium trichloride heptahydrate (1.31 g, 3.52 mmol) in methanol (10 ml) while stirring and ice-cooling, and the resulting mixture was further stirred for 10 minutes. Water (15 ml) was added to the reaction mixture. The mixtue was stirred for 10 minutes and then extracted with ethyl acetate (15 ml×3). The organic layers were combined, washed with water (50 ml) and with brine (50 ml), and dried over anhydrous magnesium sulfate (20 g) to concentrate, yielding an oily material (1.5279 g).

This oily material was azeotropically distilled with benzene (10 ml×2). To a solution of the resulting residue in absolute methanol (10 ml) there was added sodium methoxide (5.22N, 0.023 ml, 0.12 mmol), and the whole mixture was stirred under argon atmosphere at room temperature for 3 hours. Acetic acid (0.1 ml) was added to the reaction mixture followed by concentration. Water (15 ml) was added to the residue and the resulting mixture was extracted with ethyl acetate (15 ml×3). The organic layers were combined, washed with water (50 ml) and with brine (50 ml), and dried over anhydrous magnesium sulfate (20 g) to concentrate, yielding an oily product (1.3384 g).

This oily product was subjected to silica gel column chromatography using ethyl acetate/cyclohexane (1/1) to resolve into each isomer. First, there was eluted a less polar fraction, 16,16-dimethyl-15-epi-20a,20b,20c,20d-tetrahomo-2,5,6,7-tetranor-18,18,19,19-tetradehydro-4,8-inter-m-phenylene $PGI_2$ methyl ester (599.0 mg, 1.28 mmol, 44% yield), which was then recrystallized from ethyl acetate/n-hexane (1/8) to afford a colorless needle-like crystal. Subsequently, there was eluted, as a more polar fraction, 16,16-dimethyl-20a,20b,20c,20d-tetrahomo-2,5,6,7-tetranor-18,18,19,19-tetradehydro-4,8-inter-m-phenylene $PGI_2$ methyl ester (590.0 mg, 1.26 mmol, 43% yield). These products were assigned the corresponding structures described above on the following data.

16,16-Dimethyl-20a,20b,20c,20d-tetrahomo-2,5,6,7-tetranor-18,18,19,19-tetradehydro-4,8-inter-m-phenylene PGI$_2$ methyl ester IR (Liquid Film): 3402, 2950, 2912, 2860, 1730, 1598, 1443, 1365, 1295, 1242, 1194, 1175, 1093, 1068, 1043, 1000, 963, 885, 859, 834, 764, 742 cm$^{-1}$.

NMR (400 MHz, CDCl$_3$, δ): 0.90 (3H, t, J=7.00 Hz); 0.96 (3H, s); 0.97 (3H, s); 1.24–1.42 (4H, m); 1.46–1.57 (2H, m); 1.88–1.98 (1H, m); 2.03–2.28 (4H, m); 2.32–2.43 (1H, m); 2.59–2.72 (3H, m); 2.85–2.93 (2H, m); 3.03–3.16 (1H, m); 3.38 (1H, t, J=8.79 Hz); 3.53–3.63 (1H, m); 3.66 (3H, s); 3.81–3.90 (1H, m); 3.96–4.04 (1H, m); 5.04–5.14 (1H, m); 5.59–5.68 (2H, m); 6.75 (1H, t, J=7.33 Hz); 6.93 (1H, d, J=7.33 Hz); 6.96 (1H, d, J=7.33 Hz).

MASS (EI, m/e): 468 (M$^+$).

HR MASS: Calcd. (C$_{29}$H$_{40}$O$_5$, M$^+$); 468.2875, Found (M$^+$); 468.2866.

16,16-Dimethyl-15-epi-20a,20b,20c,20d-tetrahomo-2,5,6,7-tetranor-18,18,19,19-tetradehydro-4,8-inter-m-phenylene PGI$_2$ methyl ester Melting Point: 45.5°–47° C.

IR (KBr): 3420, 2960, 2930, 2860, 1760, 1590, 1442, 1358, 1322, 1294, 1250, 1185, 1087, 1065, 1027, 1000, 975, 888, 862, 836, 743 cm$^{-1}$.

NMR (400 MHz, CDCl$_3$, δ): 0.90 (3H, t, J=7.08 Hz); 0.97 (3H, s); 0.98 (3H, s); 1.24–1.43 (4H, m); 1.46–1.56 (2H, m); 1.96–2.04 (1H, m); 2.07–2.28 (4H, m); 2.35–2.42 (2H, m); 2.46–2.53 (1H, m); 2.60–2.81 (3H, m); 2.86–2.94 (2H, m); 3.47 (1H, t, J=8.30 Hz); 3.65 (3H, s); 3.91–3.98 (1H, m); 4.02–4.08 (1H, m); 5.10–5.18 (1H, m); 5.69–5.79 (2H, m); 6.76 (1H, t, J=7.33 Hz); 6.96 (1H, d, J=7.33 Hz); 7.00 (1H, d, J=7.33 Hz).

MASS (EI, m/e): 468 (M$^+$).

HR MASS: Calcd. (C$_{29}$H$_{40}$O$_5$, M$^+$); 468.2875, Found (M$^+$); 468.2874.

EXAMPLE 20:
16,16-dimethyl-20a,20b,20c,20d-tetrahomo-2,5,6,7-tetranor-18,18,19,19-tetradehydro-4,8-inter-m-phenylene PGI$_2$ (64)

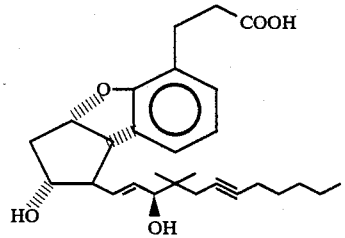

(64)

An aqueous sodium hydroxide solution (1N, 2.9 ml, 2.9 mmol) was added to a solution of 16,16-dimethyl-20a,20b,20c,20d-tetrahomo-2,5,6,7-tetranor-18,18,19,19-tetradehydro-4,8-inter-m-phenylene PGI$_2$ methyl ester (271.4 mg, 0.58 mmol) in methanol (10 ml) and the resulting mixture was stirred under argon atmosphere at room temperature for 2 hours. Hydrochloric acid (1N, 3.5 ml) was added to the reaction mixture. Water (15 ml) was then added and the mixture was extracted with ethyl acetate (15 ml×3). The organic layers were combined, washed with water (50 ml) and with brine (50 ml), and dried over anhydrous magnesium sulfate (20 g) to concentrate, yielding 16,16-dimethyl-20a,20b,20c,20d-tetrahomo-2,5,6,7-tetranor-18,18,19,19-tetradehydro-4,8-inter-m-phenylene PGI$_2$ (243,4 mg, 0.54 mmol, 92% yield) as a single product. This product was recrystallized from ethyl acetate/cyclohexane (2/3) to afford a colorless needle-like crystal. This product was assigned the above described structure based on the following data.

Melting Point: 103°–105° C.

IR (KBr): 3400 (3650–2250), 2950, 2915, 2850, 1700, 1599, 1450, 1290, 1260, 1245, 1200, 1070, 1020, 999, 960, 920, 855, 783, 760, 740, 612 cm$^{-1}$.

NMR (400 MHz, CDCl$_3$, δ): 0.92 (3H, t, J=7.08 Hz); 0.98 (3H, s); 1.24–1.42 (5H, m); 1.45–1.55 (2H, m); 1.94–2.03 (1H, m); 2.06–2.30 (5H, m); 2.38–2.47 (1H, m); 2.58–2.77 (3H, m); 2.82–2.97 (2H, m), 3.44 (1H, t, J=8.55 Hz); 3.89–3.96 (1H, m); 4.02–4.04 (1H, m); 5.08–5.19 (1H, m); 5.61–5.73 (2H, m); 6.77(1H, t, J=7.33 Hz); 6.93–7.03 (2H, m).

MASS (EI, m/e): 454 (M$^+$).

HR MASS: Calcd. (C$_{28}$H$_{38}$O$_5$, M$^+$); 454.2719, Found (M$^+$); 454.2710.

EXAMPLE 21:
16,16-Dimethyl-15-epi-20a,20b,20c,20d-tetrahomo-2,5,6,7-tetranor-18,18,19,19-tetradehydro-4,8-inter-m-phenylene PGI$_2$ (65)

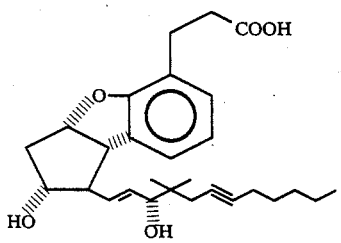

(65)

An aqueous sodium hydroxide solution (1N, 2.7 ml, 2.7 mmol) was added to a solution of 16,16-dimethyl-15-epi-20a,20b,20c,20d-tetrahomo-2,5,6,7-tetranor-18,18,19,19-tetradehydro-4,8-inter-m-phenylene PGI$_2$ methyl ester (251.8 mg, 0.54 mmol) in methanol (10 ml) and the resulting mixture was stirred under argon atmosphere at room temperature for 2 hours. Acetic acid (1N, 3ml) was added to the reaction mixture. Water (15 ml) was then added and the mixture was extracted with ethyl acetate (15 ml×3). The organic layers were combined, washed with water (50 ml) and with brine (50 ml), and dried over anhydrous magnesium sulfate (20 g) to concentrate, yielding quantitatively 16,16-dimethyl-15-epi-20a,20b,20c,20d-tetrahomo-2,5,6,7-tetranor-18,18,19,19-tetradehydro-4,8-inter-m-phenylene PGI$_2$ (244.2 mg, 0.54 mmol) as a single product. This was recrystallized from ethyl acetate/cyclohexane (1/3) to afford a colorless needle-like crystal. This product was assigned the above described structure by the following data.

Melting Point: 113°–114° C.

IR (KBr): 3360 (3700–2240), 2955, 1703, 1599, 1440, 1360, 1340, 1293, 1260, 1190, 1147, 1090, 1060, 1024, 1002, 960, 940, 888, 854, 833, 738, 600 cm$^{-1}$.

NMR (400 MHz, CDCl$_3$, δ): 0.90 (3H, t, J=7.08 Hz); 0.98 (6H, s); 1.25–1.43 (4H, m); 1.47–1.56 (2H, m); 2.00–2.08 (1H, m); 2.08–2.28 (4H, m); 2.51–2.58 (1H, m); 2.56–2.76 (4H, m); 2.83–2.97 (3H, m); 3.51 (1H, t, J=8.06 Hz); 3.94–3.99 (1H, m); 4.03–4.07 (1H, m);

5.11–5.19 (1H, m); 5.68–5.77 (2H, m); 6.78 (1H, t, J=7.33 Hz); 6.99 (1H, d, J=7.33 Hz); 7.02 (1H, d, J=7.33 Hz).

MASS (EI, m/e): 454 (M+).

HR MASS: Calcd. ($C_{28}H_{38}O_5$, M+); 454.2719. Found (M+); 454.2744.

EXAMPLE 22:
3-Decarboxy-3-hydroxymethyl-16-methyl-20a-homo-2,5,6,7-tetranor-18,18,19,19-tetradehydro-4,8-inter-m-phenylene $PGI_2$ (66)

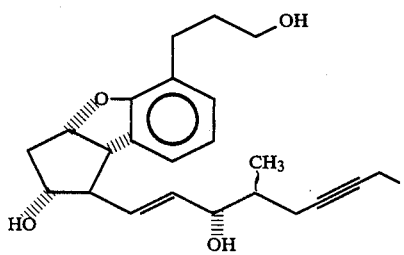

At −78° C., diisobutyl aluminum hydride (0.93 ml, 1.39 mmol) was added to a solution of 16-methyl-20a-homo-2,5,6,7-tetranor-18,18,19,19-tetradehydro-4,8-inter-m-phenylene $PGI_2$ methyl ester (114.6 mg, 0.28 mmol) in anhydrous toluene (10 ml) and the mixture was stirred for 20 minutes. The mixture was further stirred at 0° C. for 15 minutes. A saturated aqueous ammonium chloride solution (5 ml) was added to the reaction mixture. Further, hydrochloric acid (1N, 6 ml) was added to the reaction mixture followed by extraction with ethyl acetate (10 ml×3). The organic layers were combined, washed with water (30 ml) and with brine (30 ml), and dried over anhydrous sodium sulfate (20 g) to concentrate, yielding an oily material (132.3 mg). This oily material was purified by silica gel column chromatography using ethyl acetate as an eluent to afford a colorless oily product, 3-decarboxy-3-hydroxymethyl-16-methyl-20a-homo-2,5,6,7-tetranor-18,18,19,19-tetradehydro-4,8-inter-m-phenylene $PGI_2$ (88.4 mg, 0.23 mmol, 83% yield). This product was assigned the above described structure based on the following data.

IR (Liquid Film): 3350, 2970, 2928, 1598, 1448, 1320, 1257, 1193, 1061, 1022, 970, 861, 740 cm$^{-1}$.

NMR (400 MHz, $CDCl_3$, δ): 0.98 (1.5 H, d, J=6.83 Hz); 1.03 (1.5 H, d, J=6.83 Hz); 1.09–1.18 (3H, m); 1.71–2.00 (4H, m); 2.08–2.25 (3H, m); 2.20–2.35 (1H, m); 2.36–2.45 (1H, m); 2.57–2.76 (3H, m); 2.76 (3H, broad s); 3.39–3.47 (1H, m); 3.51–3.63 (2H, m); 3.85–3.93 (1H, m); 3.98–4.05 (0.5H, m); 4.11–4.17 (0.5H, m); 5.05–5.14 (1H, m); 5.50–5.70 (2H, m); 6.71–6.82 (1H, m); 6.92–6.99 (2H, m).

MASS (EI, m/e): 384 (M+).

HR MASS: Calcd. ($C_{24}H_{32}O_4$, M+); 384.2300, Found (M+); 384.2293.

EXAMPLE 23:
16,16-Dimethyl-2,5,6,7-tetranor-18,18,19,19-tetradehydro-4,8-inter-m-phenylene $PGI_2$ methyl ester, 11,15-bis(t-butyl-dimethylsilyl) ether (67)

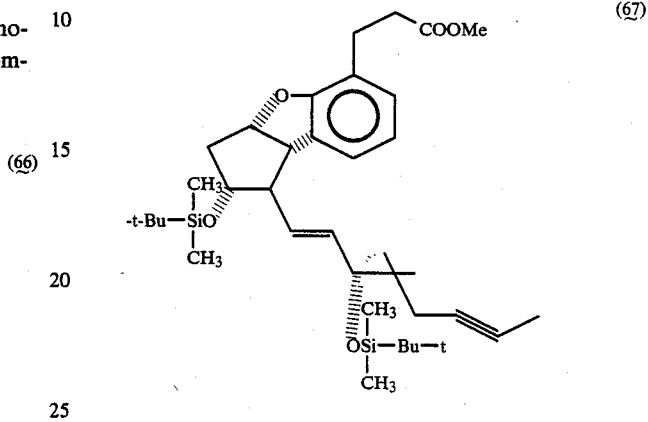

Imidazole (51.7 mg, 0.76 mmol) and t-butyl-dimethylsilyl chloride (57.6 mg, 0.38 mmol) were added to a solution of 16,16-dimethyl-2,5,6,7-tetranor-18,18,19,19-tetradehydro-4,8-inter-m-phenylene $PGI_2$ methyl ester (51.7 mg, 0.13 mmol) in anhydrous DMF (1 ml) and the resulting mixture was stirred at room temperature for 41 hours. A saturated aqueous sodium hydrogencarbonate solution (10 ml) was added to the reaction mixture followed by extraction with ethyl acetate (10 ml×3). The organic layers were combined, washed with water (30 ml) and with brine (30 ml), and dried over anhydrous sodium sulfate (15 g) to concentrate, yielding an oily material (151.4 mg). The oily material was purified by silica gel column chromatography using ethyl acetate/cyclohexane (1/10) to afford a colorless oily product, 16,16-dimethyl-2,5,6,7-tetranor-18,18,19,19-tetradehydro-4,8-inter-m-phenylene $PGI_2$ methyl ester, 11,15-bis-(t-butyl-dimethylsilyl) ether (78.2 mg, 0.125 mmol, 99% yield). This product was assigned the above described structure based on the following data.

IR (Liquid Film): 2949, 2880, 2851, 1739, 1593, 1450, 1381, 1359, 1300, 1246, 1188, 1063, 1003, 976, 940, 885, 860, 830, 770, 743, 670 cm$^{-1}$.

NMR (100 MHz, $CDCl_3$, δ): −0.06 (3H, s); 0.00 (3H, s); 0.02 (3H, s); 0.08 (3H, s); 0.75 (9H, s); 0.87 (6H, s); 0.92 (9H, s); 1.81 (3H, t, J=2.2 Hz); 2.01–2.20 (2H, m); 2.25–3.00 (7H, m); 3.38–3.66 (1H, m); 3.68 (3H, s); 3.82–4.10 (2H, m); 5.02–5.28 (1H, m); 5.49–5.62 (2H, m); 6.61–7.09 (3H, m).

MASS (EI, m/e): 640 (M+).

EXAMPLE 24:
3-Decarboxy-3-hydroxymethyl-16,16-dimethyl-2,5,6,7-tetranor-18,18,19,19-tetradehydro-4,8-inter-m-phenylene PGI₂, 11,15-bis(t-butyl-dimethylsilyl) ether (68)

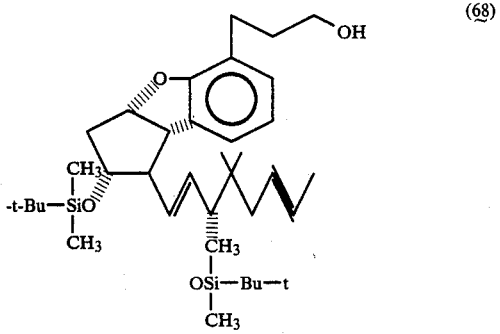

Under argon atmosphere at −20° C., diisobutyl aluminum hydride (0.15 ml, 0.23 mmol) was added to a solution of 16,16-dimethyl-2,5,6,7-tetranor-18,18,19,19-tetradehydro-4,8-inter-m-phenylene PGI₂ methyl ester 11,15-bis(t-butyldimethylsilyl) ether (47 mg, 0.075 mmol) in toluene (2 ml) and the resulting mixture was stirred for 20 minutes. A saturated aqueous ammonium chloride solution (3 ml) was added to the reaction mixture. Further, hydrochloric acid (0.1N, 3 ml) was added to the mixture followed by extraction with ethyl acetate (6 ml×3). The organic layers were combined, washed with water (20 ml) and with brine (20 ml), and dried over anhydrous sodium sulfate (10 g) to concentrate, yielding quantitatively a single, colorless oily product, 3-decarboxy-3-hydroxymethyl-16,16-dimethyl-2,5,6,7-tetranor-18,18,19,19-tetradehydro-4,8-inter-m-phenylene PGI₂, 11,15-bis(t-butyl-dimethylsilyl)ether (44.8 mg, 0.075 mmol). This product was assigned the above described structure based on the following data.

IR (Liquid Film): 3370, 2951, 2925, 2877, 2852, 1598, 1446, 1380, 1357, 1248, 1185, 1090, 1055, 1028, 1003, 968, 902, 841, 830, 768, 741, 669 cm⁻¹.

NMR (100 MHz, CDCl₃, δ): −0.06 (3H, s); 0.002 (3H, s); 0.03 (3H, s); 0.08 (3H, s); 0.75 (9H, s); 0.92 (12H, s); 1.78 (3H, t, J=2.42 Hz); 1.80–2.18 (4H, m); 2.23–2.46 (1H, m); 2.50–2.77 (4H, m); 3.42–3.70 (3H, m); 3.82–4.10 (2H, m); 5.02–5.30 (1H, m); 5.50–5.63 (2H, m); 6.63–7.08 (3H, m)

MASS (EI, m/e): 612 (M+).

EXAMPLE 25:
3-Decarboxy-3-hydroxymethyl-16,16-dimethyl-2,5,6,7-tetranor-18,18,19,19-tetradehydro-4,8-inter-m-phenylene PGI₂ (69)

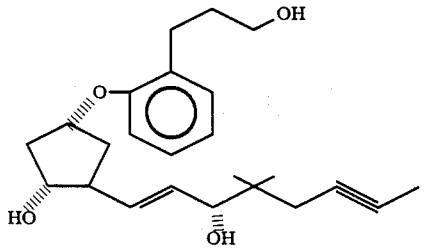

Tetra-n-butylammonium fluoride (148.8 mg, 0.57 mmol) was added to a solution of 3-decarboxy-3-hydroxymethyl-16,16-dimethyl-2,5,6,7-tetranor-18,18,19,19-tetradehydro-4,8-inter-m-phenylene PGI₂, 11,15-bis(t-butyl-dimethylsilyl)ether (68 mg, 0.114 mmol) in anhydrous THF (1 ml), and the resulting mixture was stirred at room temperature for 29 hours. Water (2 ml) and hydrochloric acid (0.1N, 2 ml) were added to the reaction mixture followed by extraction with ethyl acetate (5 ml×3). The organic layers were combined, washed with brine (20 ml), and dried over anhydrous sodium sulfate (5 g) to concentrate, yielding an oily material (67.1 mg). This oily material was purified by silica gel column chromatography using ethyl acetate/cyclohexane (6/1) to afford a colorless oily product, 3-decarboxy-3-hydroxymethyl-16,16-dimethyl-2,5,6,7-tetranor-18,18,19,19-tetradehydro-4,8-inter-m-phenylene PGI₂ (37.5 mg, 0.098 mmol, 86% yield). This product was assigned the above described structure based on the following data.

IR (Liquid Film): 3350, 2950, 2905, 2855, 1586, 1441, 1250, 1183, 1063, 1016, 964, 863, 740 cm⁻¹.

NMR (100 MHz, CDCl₃, δ): 0.97 (3H, s); 0.98 (3H, s); 1.81 (3H, d, J=2.44 Hz): 1.55–1.74 (3H, broad s); 1.77–1.94 (1H, m); 1.97–2.15 (2H, m); 2.16–2.32 (2H, m); 2.47–2.52 (1H, m); 2.61–2.75 (3H, m); 3.51 (1H, t, J=8.3 Hz); 3.54–3.63 (2H, m); 3.92–4.01 (1H, m); 4.02–4.06 (1H, m); 5.13–5.19 (1H, m); 5.64–5.76 (2H, m); 6.82 (1H, t, J=7.33 Hz); 6.97 (2H, d, J=7.33 Hz).

MASS (EI, m/e): 384 (M+).

HR MASS: Calcd. (C₂₄H₃₂O₄, M+); 384.2300, Found (M+); 384.2295.

EXAMPLE 26:
16,16-Dimethyl-2,5,6,7-tetranor-18,18,19,19-tetradehydro-4,8-inter-m-phenylene PGI₂ methyl ester (52)

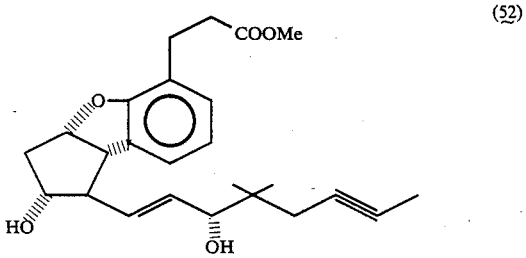

Triethylamine (0.029 ml, 0.208 mmol) and ethyl chloroformate (0.017 ml, 0.176 mmol) were added to a solution of 16,16-dimethyl-2,5,6,7-tetranor-18,18,19,19-tetrahydro-4,8-inter-m-phenylene PGI₂ (63.8 mg, 0.160 mmol) in anhydrous THF (7 ml) while ice-cooling. After the mixture was stirred under argon atmosphere at room temperature for 4 hours, absolute methanol (0.065 ml, 1.60 mmol) was added. The mixture was stirred overnight at 60° C. Ethyl acetate (10 ml) was added to the reaction mixture, and the resulting mixture was washed with saturated aqueous sodium bicarbonate solution and with brine, and dried over anhydrous sodium sulfate to concentrate, yielding an oily material. This oily material was purified by silica gel column chromatography using cyclohexane/ethyl acetate (1/4) to afford 16,16-dimethyl-2,5,6,7-tetranor-18,18,19,19-tetradehydro-4,8-inter-m-phenylene PGI₂ methyl ester (46.97 mg, 0.114 mmol, 71.3% yield). The above described structure of this product was confirmed by the accordance of the TLC, IR, MASS and NMR data with those of the product synthesized in Example 12.

In a similar manner, methanol used as an alcohol can be replaced by ethanol, cyclohexyl alcohol, furfuryl alcohol, methyl lactate, benzyl alcohol, p-bromobenzyl alcohol, phenethyl alcohol, 2-butyne-1-ol, phenol or p-methylphenol to give desired esters, respectively.

EXAMPLE 27: Gastric Cytoprotection Activity

Gastric cytoprotection activity of the compounds of the present invention was investigated according to the method described by A. Robert in Gastroenterology, 77(3), 443 (1979).

A compound to be tested is orally administered to a group of animals and, 30 minutes later, 0.2N NaOH is orally applied to the animals. One hour later, the animals are sacrificed under anesthesia by chloroform and their stomachs are removed and fixed in 5% formalin solution. The stomach is then incised along the greater curvature. Lengths of lesions appearing on the stomach corpus are measured and summed. The total length is served as an ulcer index. A dose amount of a compound to be tested, by which the ulcer index is reduced to 50% of the index of a control group (100%), is designated as $ED_{50}$.

The results, i.e., the obtained values of $ED_{50}$, are shown in Table 1.

TABLE 1

| Gastric cytoprotection activity | |
|---|---|
| Compound | $ED_{50}$ (μg/kg) |
| 38 | 24.1 |
| 39 | 0.38 |
| 42 | 0.093 |
| 46 | 2.33 |
| 50 | 3.74 |
| 54 | 2.80 |
| 57 | 1.14 |
| 60 | — |
| 64 | 27.7 |
| 69 | 0.82 |

EXAMPLE 28: Gastric Acid Secretion Inhibiting Activity

Gastric acid secretion-inhibiting activity of the compounds of the present invention was investigated according to the pylorus ligation method described by Shay in Gastroenterology, 5, 43 (1945).

Under anesthesia by ether, the abdomen of a group of rats is incised at its median and the pylorus is ligated with a silk thread. Simultaneously, a compound to be tested is injected into the duodenum of the same rat. The abdomen is then closed. Five hours later, the abdomen is again incised and the esophagus is ligated. The whole stomach is then removed. The stomach is cut along the greater curvature and the contents of the stomach are transferred to a graduated centrifugal tube. After centrifugation at 3,000 rpm for 10 minutes, the volume of the gastric juice is measured. A portion of the supernatant is taken and titrated to pH 7 with 0.1N NaOH in a pH stat, Radio Meter Inc. An average dose amount of a compound to be tested in a group of five animals, by which either the volume of gastric juice (in ml) or the acidity (in mEq/ml) is reduced to 50% of the corresponding value of a control group, is designated as $ED_{50}$.

The results, i.e., the obtained values of $ED_{50}$, are shown in Table 2.

TABLE 2

| Gastric acid secretion-inhibiting activity | | |
|---|---|---|
| | $ED_{50}$ (mg/kg) | |
| Compound | Acidity | Gastric juice volume |
| 38 | 0.49 | >1 |
| 39 | 0.0095 | 0.025 |
| 42 | 0.023 | 0.018 |
| 46 | 0.14 | 0.12 |
| 50 | 0.74 | 0.51 |
| 54 | 0.23 | >0.3 |
| 57 | 0.087 | 0.21 |
| 60 | >3 | >3 |
| 64 | >10 | 5.6 |
| 69 | 0.27 | >3 |

EXAMPLE 29: Gastric Acid Secretion Inhibiting Activity

The gastric acid secretion-inhibiting activity of the compounds of the present invention was also investigated according to the method described by M. Ghosh and H. Schild, Br. J. Pharmacol., 13, 54 (1958).

A group of male SD rats is incised in the abdomen under anesthesia by urethane. The lumen of the stomach is perfused with saline through a double tube cannula which has been inserted into the stomach through a lumen formed in the cardia. The pH of draining gastric acid is monitored by a pH meter. The secretion of gatric acid is stimulated by continuous infusion of pentagastrin at a rate of 0.05 μg/kg per minute. When the pH of the gastric acid becomes stable at about 4.0, a compound to be tested is injected through the femoral vein. An index for the gastric acid secretion-inhibiting activity of a compound to be tested is calculated from the area surrounded by a curve drawn by the time course of the pH of the gastric acid, from the time point when an initial increase of the pH is observed due to the gastric acid secretion-inhibition by the compound injected to the time point when the pH comes back to the baseline. The index thus obtained is compared to that of $PGE_2$ and the ratio of the index to that of $PGE_2$ is calculated.

The results, i.e., the obtained values of such ratios, are shown in Table 3.

TABLE 3

| Gastric acid secretion-inhibiting activity | |
|---|---|
| Compound | Relative activity ($PGE_2$ = 1) |
| $PGE_2$ | 1 |
| 38 | — |
| 39 | — |
| 42 | 26 |
| 46 | — |
| 50 | — |
| 54 | 16 |
| 57 | 5.3 |
| 60 | 0.5 |
| 64 | 0.25 |
| 69 | 2.7 |

EXAMPLE 30: Platelet Aggregation Inhibiting Activity

Platelet aggregation-inhibiting activity of the compounds of the present invention was investigated by the method described below.

The blood taken from the cubital median vein of a person is centrifuged at 800 rpm for 10 minutes and the supernatant is used as platelet-rich plasma (PRP). The PRP is distributed into small test tubes, and adenosine diphosphate (ADP) is added at a final concentration of 10 μM thereinto to induce platelet aggregation. The size of the aggregation is determined in a platelet aggregation measuring apparatus (RiKa-Denki, Tokyo, Japan) by measuring the change in turbidity of a sample in the small test tube. A compound to be tested is added to the sample one minute before the addition of ADP. The concentration of the compound to be tested, by which the platelet aggregation is reduced to 50% of that observed in a control group, is designated as $IC_{50}$.

The results, i.e., the obtained values of $IC_{50}$, are shown in Table 4.

TABLE 4

| Platelet aggregation-inhibiting activity | |
| --- | --- |
| Compound | $IC_{50}$ (ng/ml) |
| 38 | 6.5 |
| 39 | 0.42 |
| 42 | 0.34 |
| 46 | 0.96 |
| 50 | 0.63 |
| 54 | 7.3 |
| 57 | 3.2 |
| 60 | 3.0 |
| 64 | 5.5 |
| 69 | — |

EXAMPLE 31: Hypotensive Activity

Hypotensive activity of the compounds of the present invention was investigated in such a manner as described below.

A catheter is inserted into and held in the carotid of a group of Wistar male rats under anesthesia by chloralose. Another end of the catheter is connected to a polygraph with a pressure transducer to measure the blood pressure in the carotid. A compound to be tested is injected via a catheter connected to the femoral artery. A dose amount of a compound to be tested, by which the blood pressure is reduced by 25 mmHg in the dose-response curve of the hypotensive compound, is designated as $ED_{25}$.

The results, i.e., the obtained values of $ED_{25}$, are shown in Table 5.

TABLE 5

| Hypotensive activity | |
| --- | --- |
| Compound | $ED_{25}$ (μg/kg) |
| 38 | 0.57 |
| 39 | 0.07 |

TABLE 5-continued

| Hypotensive activity | |
| --- | --- |
| Compound | $ED_{25}$ (μg/kg) |
| 42 | — |
| 46 | 0.22 |
| 50 | — |
| 54 | 0.64 |
| 57 | 0.14 |
| 60 | — |
| 64 | 15.5 |
| 69 | >100 |

What is claimed is:
1. A 2,5,6,7-tetranor-18,18,19,19-tetradehydro-4,8-inter-m-phenylene $PGI_2$ derivative represented by the formula:

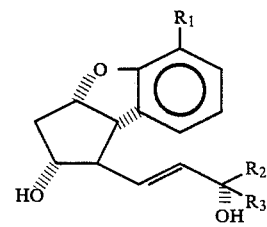

wherein:
$R_1$ is
(i) —$CH_2CH_2COOR_4$,
(ii) —$CH_2CH_2CH_2OH$, or
(iii)

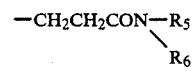

in which $R_4$ is hydrogen, or a pharmacologically acceptable cation or ester residue, and $R_5$ and $R_6$ may be same or different and are independently selected from the class consisting of hydrogen, normal alkyl groups having 1 to 12 carbon atoms, branched alkyl groups having 3 to 12 carbon atoms, cycloalkyl groups having 3 to 12 carbon atoms, cycloalkylalkylene groups having 4 to 13 carbon atoms, and phenyl;
$R_2$ is hydrogen, methyl, ethyl or propyl; and
$R_3$ is —$C_tH_{2t}$—C≡C—$R_7$
in which $C_tH_{2t}$ represents a normal or branched alkylene group, t is an integer having a value of 1 to 6, and $R_7$ is a normal alkyl group having 1 to 6 carbon atoms.

* * * * *

UNITED STATES PATENT AND TRADEMARK OFFICE
CERTIFICATE OF CORRECTION

PATENT NO. : 4,880,939

DATED : 11/14/89

INVENTOR(S) : Ohno et al

It is certified that error appears in the above-identified patent and that said Letters Patent is hereby corrected as shown below:

In first page, block 73 delete "Toray Industries" and insert --Toray Industries, Inc.--.

Signed and Sealed this

Fifth Day of March, 1991

Attest:

HARRY F. MANBECK, JR.

*Attesting Officer*  *Commissioner of Patents and Trademarks*